(12) United States Patent
Dallwig et al.

(10) Patent No.: US 7,655,409 B2
(45) Date of Patent: Feb. 2, 2010

(54) CYANINE DYE COMPOUNDS

(75) Inventors: Jason Dallwig, Eugene, OR (US); David Hagen, Eugene, OR (US); Shih-Jung Huang, Eugene, OR (US); Gerald Thomas, Springfield, OR (US); Stephen Yue, Eugene, OR (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 12/240,218

(22) Filed: Sep. 29, 2008

(65) Prior Publication Data

US 2009/0047683 A1  Feb. 19, 2009

Related U.S. Application Data

(62) Division of application No. 11/005,860, filed on Dec. 6, 2004, now Pat. No. 7,446,202.

(60) Provisional application No. 60/554,472, filed on Mar. 18, 2004, provisional application No. 60/527,234, filed on Dec. 5, 2003.

(51) Int. Cl.
*C12Q 1/68* (2006.01)
*C07H 21/04* (2006.01)
*C07H 19/04* (2006.01)

(52) U.S. Cl. .................. 435/6; 536/23.1; 536/24.3; 536/24.33; 536/26.6

(58) Field of Classification Search .............. 435/6; 536/23.1, 24.3, 24.33, 26.6
See application file for complete search history.

(56) References Cited

U.S. PATENT DOCUMENTS

| 3,840,377 A | 10/1974 | Sato et al. |
| 4,003,750 A | 1/1977 | Heseltine et al. |
| 4,343,782 A | 8/1982 | Shapiro |
| 4,386,146 A | 5/1983 | Kishino et al. |
| 4,510,235 A | 4/1985 | Ukai et al. |
| 4,520,110 A | 5/1985 | Stryer et al. |
| 4,542,104 A | 9/1985 | Stryer et al. |

(Continued)

FOREIGN PATENT DOCUMENTS

DE  917330  6/1954

(Continued)

OTHER PUBLICATIONS

U.S. Appl. No. 11/005,860, "Notice of Allowance mailed Jun. 30, 2008".

(Continued)

*Primary Examiner*—Jezia Riley
(74) *Attorney, Agent, or Firm*—Life Technologies Corporation; James K. Blodgett

(57) ABSTRACT

Cyanine dye compounds having a negatively charged substituent that are nucleic acid stains, particularly for fluorescent staining of DNA, including compounds having the formula

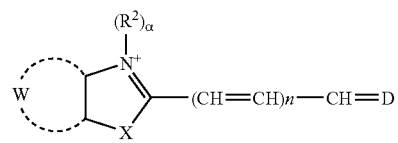

wherein W forms one or two fused 5- or 6-membered aromatic rings, α has a value of 0 or 1, n has a value of 0, or 1, X is O, S, or Se, and D is a pyridinium, or quinolinium moiety, provided that the compound has at least one negatively charged substituent.

5 Claims, 7 Drawing Sheets

U.S. PATENT DOCUMENTS

| | | | |
|---|---|---|---|
| 4,603,209 A | 7/1986 | Tsien et al. |
| 4,665,024 A | 5/1987 | Mansour et al. |
| 4,711,955 A | 12/1987 | Ward et al. |
| 4,774,339 A | 9/1988 | Haugland et al. |
| 4,810,636 A | 3/1989 | Corey et al. |
| 4,812,409 A | 3/1989 | Babb et al. |
| 4,837,141 A | 6/1989 | Kohno et al. |
| 4,849,362 A | 7/1989 | DeMarinis et al. |
| 4,859,582 A | 8/1989 | Stryer et al. |
| 4,883,867 A | 11/1989 | Lee et al. |
| 4,945,171 A | 7/1990 | Haugland et al. |
| 4,957,870 A | 9/1990 | Lee et al. |
| 4,997,928 A | 3/1991 | Hobbs |
| 5,047,519 A | 9/1991 | Hobbs et al. |
| 5,049,673 A | 9/1991 | Tsien et al. |
| 5,055,556 A | 10/1991 | Stryer et al. |
| 5,132,432 A | 7/1992 | Haugland et al. |
| 5,169,788 A | 12/1992 | Chen et al. |
| 5,171,534 A | 12/1992 | Smith et al. |
| 5,187,288 A | 2/1993 | Kang et al. |
| 5,208,148 A | 5/1993 | Haugland et al. |
| 5,221,518 A | 6/1993 | Mills |
| 5,227,487 A | 7/1993 | Haugland et al. |
| 5,242,805 A | 9/1993 | Naleway et al. |
| 5,248,782 A | 9/1993 | Haugland et al. |
| 5,268,486 A | 12/1993 | Waggoner et al. |
| 5,274,113 A | 12/1993 | Kang et al. |
| 5,314,805 A | 5/1994 | Haugland et al. |
| 5,321,130 A | 6/1994 | Yue et al. |
| 5,332,666 A | 7/1994 | Prober et al. |
| 5,352,803 A | 10/1994 | Mattingly |
| 5,362,628 A | 11/1994 | Haugland et al. |
| 5,401,847 A | 3/1995 | Glazer |
| 5,405,975 A | 4/1995 | Kuhn et al. |
| 5,410,030 A | 4/1995 | Yue et al. |
| 5,433,896 A | 7/1995 | Kang et al. |
| 5,436,134 A | 7/1995 | Haugland et al. |
| 5,442,045 A | 8/1995 | Haugland et al. |
| 5,445,946 A | 8/1995 | Roth et al. |
| 5,451,343 A | 9/1995 | Neckers et al. |
| 5,453,517 A | 9/1995 | Kuhn et al. |
| 5,459,268 A | 10/1995 | Haugland et al. |
| 5,459,276 A | 10/1995 | Kuhn et al. |
| 5,486,616 A | 1/1996 | Waggoner et al. |
| 5,501,980 A | 3/1996 | Katerinopoulos et al. |
| 5,534,416 A | 7/1996 | Millard et al. |
| 5,545,535 A | 8/1996 | Roth et al. |
| 5,565,554 A | 10/1996 | Glazer et al. |
| 5,569,587 A | 10/1996 | Waggoner |
| 5,569,766 A | 10/1996 | Waggoner et al. |
| 5,573,904 A | 11/1996 | Mattingly |
| 5,573,909 A | 11/1996 | Singer et al. |
| 5,578,439 A | 11/1996 | Inagaki |
| 5,582,977 A | 12/1996 | Yue et al. |
| 5,616,502 A | 4/1997 | Haugland et al. |
| 5,627,027 A | 5/1997 | Waggoner |
| 5,648,270 A | 7/1997 | Kuhn et al. |
| 5,656,449 A | 8/1997 | Yue |
| 5,656,554 A | 8/1997 | Desai et al. |
| 5,658,735 A | 8/1997 | Lee |
| 5,658,751 A | 8/1997 | Yue et al. |
| 5,691,145 A | 11/1997 | Pitner et al. |
| 5,696,157 A | 12/1997 | Wang et al. |
| 5,714,327 A | 2/1998 | Houthoff et al. |
| 5,760,201 A | 6/1998 | Glazer |
| 5,798,276 A | 8/1998 | Haugland et al. |
| 5,800,996 A | 9/1998 | Lee et al. |
| 5,830,912 A | 11/1998 | Gee et al. |
| 5,846,737 A | 12/1998 | Kang |
| 5,847,162 A | 12/1998 | Lee et al. |
| 5,853,969 A | 12/1998 | Harada et al. |
| 5,863,727 A | 1/1999 | Lee et al. |
| 5,863,753 A | 1/1999 | Haugland et al. |
| 5,869,689 A | 2/1999 | Zhang et al. |
| 5,925,517 A | 7/1999 | Tyagi et al. |
| 5,929,227 A | 7/1999 | Glazer et al. |
| 5,945,526 A | 8/1999 | Lee et al. |
| 5,963,753 A | 10/1999 | Ohtani et al. |
| 6,004,536 A | 12/1999 | Leung et al. |
| 6,008,373 A | 12/1999 | Waggoner et al. |
| 6,008,379 A | 12/1999 | Benson et al. |
| 6,017,712 A | 1/2000 | Lee et al. |
| 6,025,505 A | 2/2000 | Lee et al. |
| 6,027,709 A | 2/2000 | Little et al. |
| 6,048,982 A | 4/2000 | Waggoner et al. |
| 6,080,852 A | 6/2000 | Lee et al. |
| 6,083,699 A | 7/2000 | Leushner et al. |
| 6,103,476 A | 8/2000 | Tyagi et al. |
| 6,114,350 A | 9/2000 | Randall et al. |
| 6,130,101 A | 10/2000 | Mao et al. |
| 6,140,494 A | 10/2000 | Hamilton et al. |
| 6,153,370 A | 11/2000 | Maruyama et al. |
| 6,162,931 A | 12/2000 | Gee et al. |
| 6,184,379 B1 | 2/2001 | Josel et al. |
| 6,197,956 B1 | 3/2001 | Randall et al. |
| 6,200,752 B1 | 3/2001 | Lakowicz |
| 6,204,389 B1 | 3/2001 | Randall et al. |
| 6,221,606 B1 | 4/2001 | Benson et al. |
| 6,225,050 B1 | 5/2001 | Waggoner |
| 6,229,055 B1 | 5/2001 | Klaubert et al. |
| 6,291,203 B1 | 9/2001 | Poot et al. |
| 6,316,276 B1 | 11/2001 | Gregory et al. |
| 6,323,337 B1 | 11/2001 | Singer et al. |
| 6,329,205 B1 | 12/2001 | Diwu et al. |
| 6,348,596 B1 | 2/2002 | Lee et al. |
| 6,348,599 B1 | 2/2002 | Cummins et al. |
| 6,358,684 B1 | 3/2002 | Lee |
| 6,365,341 B1 | 4/2002 | Wu et al. |
| 6,368,801 B1 | 4/2002 | Faruqi |
| 6,372,445 B1 | 4/2002 | Davis et al. |
| 6,399,392 B1 | 6/2002 | Haugland et al. |
| 6,403,807 B1 | 6/2002 | Singh et al. |
| 6,428,667 B1 | 8/2002 | Glazer et al. |
| 6,541,205 B1 | 4/2003 | Yokoyama et al. |
| 6,562,632 B1 | 5/2003 | Szalecki et al. |
| 6,579,718 B1 | 6/2003 | Yue et al. |
| 6,664,047 B1 | 12/2003 | Haugland et al. |
| 6,716,979 B2 | 4/2004 | Diwu et al. |
| 6,967,251 B2 | 11/2005 | Haugland et al. |
| 6,972,326 B2 | 12/2005 | Haugland et al. |
| 6,977,305 B2 | 12/2005 | Leung et al. |
| 7,226,740 B2 | 6/2007 | Haugland et al. |
| 7,271,265 B2 | 9/2007 | Haugland et al. |
| 7,446,202 B2 | 11/2008 | Dallwig et al. |
| 7,566,790 B2 | 7/2009 | Leung et al. |
| 2005/0208534 A1 | 9/2005 | Dallwig et al. |
| 2005/0244976 A1 | 11/2005 | Gee et al. |
| 2006/0099638 A1 | 5/2006 | Leung et al. |
| 2007/0178511 A1 | 8/2007 | Leung et al. |
| 2007/0232805 A1 | 10/2007 | Leung |
| 2008/0039630 A1 | 2/2008 | Haugland et al. |
| 2008/0044811 A1 | 2/2008 | Haugland et al. |

FOREIGN PATENT DOCUMENTS

| | | |
|---|---|---|
| EP | 0745690 A2 | 12/1996 |
| EP | 0805376 A2 | 11/1997 |
| EP | 0472812 | 3/1998 |
| EP | 870753 | 10/1998 |
| EP | 0985964 A1 | 3/2000 |
| JP | 63-132688 | 6/1988 |
| JP | 28-04383 | 3/1990 |
| JP | 2005-287209 | 11/1993 |
| JP | 2000-319260 | 11/2000 |

| JP | 2009-218495 | 11/2001 |
| WO | WO-93/00633 | 1/1993 |
| WO | WO-93/06482 | 4/1993 |
| WO | WO-96/36882 | 11/1996 |
| WO | WO-97/12508 | 4/1997 |
| WO | WO-97/39064 | 10/1997 |
| WO | WO-97/45539 | 12/1997 |
| WO | WO-98/017826 | 4/1998 |
| WO | WO-99/037717 | 7/1999 |
| WO | WO-99/064519 | 12/1999 |
| WO | WO-00/066664 | 11/2000 |
| WO | WO-01/086264 | 11/2001 |
| WO | WO-05056687 A2 | 6/2005 |

OTHER PUBLICATIONS

U.S. Appl. No. 11/005,860, "Office Action mailed Dec. 28, 2007".
U.S. Appl. No. 11/005,860, "Response to Dec. 28, 2007 Office Action", Filed Mar. 28, 2008.
U.S. Appl. No. 11/005,860, "Response to Rest. Req.", Filed Oct. 12, 2007.
U.S. Appl. No. 11/005,860, "Restriction Req. mailed Sep. 12, 2007".
2005/056687, "PCT International Search Report", Aug. 18, 2005.
Abramo, K. H. et al., "Spectroscopic Studies of Single-Standard DNA Ligands and Oxazole Yellow Dyes", Biospectroscopy; 4(1) 1998, 27-35.
Allmann, et al., "Konformationsanalyse von Polymethinen I, Erstmaliger Nachweis von di-, tri- und all-cis-Konformationen bei sterisch gehinderten Trimethincyaninen (Carbocyaninen) der Indolin- und Benzothiazolreihe", (German Version) Anbew. Chem. Suppl. 1983, 1147-1175.
Ausubel, Frederick M. et al., "Short Protocols in Molecular Biology", 2002, 359.
Barlin, Gordon B. et al., "Purine Analogues as Amplifiers of Phleomycin. IX* Some 2- and 6-Substituted Thiazolo [4,5,-b] Pyrazines, 2-Substituted Thiazolo[4,5,-c]- and Thiazolo[5,4,-b]-Pyridines and Related Compunds", Aust. J. Chem. vol. 37 1984, 1729-1737.
Barlin, Gordon B. et al., "Purine Analogues as Amplifiers of Phleomyein. Some Thiazolo[4,5-g] pyrazines and Related Compounds", Aust. J. Chem. vol. 36 1983 983-985.
Berge, et al., "Pharmaceutical Salts", Journal of Pharmaceutical Science 66 1977, 1-19.
Brinkley, Michael, "Ch 4: A Brief Survey of Methods for Preparing Protein Conjugates with Dyes, Haptens, and Cross-Linking Reagents", Bioconjugate Chem. vol. 3, No. 1 1992, 2-13.
Brooker, L G. et al., "Color and consitution. V. The absorption of unsymmetrical cyanines. Resonance as a basis for a classification of dyes", Journal of the American Chemical Society vol. 64, Communication No. 833 From the Kodak Research Laboratories Feb. 1942, 199-210.
Bunkenborg, Jakob et al., "Concerted intercalation and minor groove recognition of DNA by a homodimeric thiazole orange dye", Bioconjugate Chemistry vol. 11, No. 6 Nov. 2000, 861-867.
Celio, M. R. et al., "Guidebook to Calcium-Binding Proteins", Oxford University Press 1996.
Chu-Moyer, Margaret V. et al., "Preparation of the Four Regioisomeric 2-(Methylthio)oxazolopyridines: Useful Synthons for Elaboration to 2-(Amino substituted)oxazolopyridines", Journal of Organic Chemistry vol. 60, No. 17 1995, 5721-5725.
Couture, Axel et al., "2-ARYL-OXazolo- and Thiazolopyrdines. Synthesis via Cyclization of N-(2 Chloro-3-Pyridinyl) Arylamides and Thiomides", Heterocycles vol. 22, No. 6 1984,1383-1385.
Couture, Axel et al., "Nouvelle Methode De Synthese De Thiazolopyridines", (French Version) J. Heterocyclin Chem. vol. 24 1987, 1765-1769.
Dos Remedios, Cristobal G. et al., "Fluorescence Resonance Energy Transfer Spectroscopy is a Reliable "Ruler" for Measuring Structural Changes in Proteins. Dispelling the Problem with the Unknown Orientation Factor", Journal of Structural Biology vol. 115 1995, 175-185.
Ficken, et al., "Diazaines and Their Quarternary Salts Part 2", CA 55:70677, abstract only of J of Chem Soc 1961, 584-588.

Ficken, G E. et al., "Diazaindenes and Their Quaternary Salts Part 1: The preparation of 2,3,3-Trimethyl-3H-1,7-diazaindene, and its Methiodides and Derived Cyanine Dyes", Journal of Chemical Society 1959, 3202-3212.
Foye, William O. et al., "Antiradiation compounds XV: Condensations of carbon disulfide with amino, chloro, cyanomethyl, and sulfonamido heterocycles", Journal of Pharmaceutical Science vol. 64, No. 8 Aug. 1975, 1371-1374.
Gadjev, "Dyes and Pigments", vol. 57(2) 2003, pp. 161-164.
Gadjev, N. I. et al., "Preparation of monomethine cyanine dyes as noncovalent labels for nucleic acids", Dyes and Pigments vol. 40 1999, 181-186.
Gaugain, Bernard et al., "DNA bifunctional intercalators. 1. Synthesis and conformational properties of an ethidium homodimer and of an acridine ethidium heterodimer", Biochemistry vol. 17, No. 24 1978, 5071-5078.
Gaugain, Bernard, "DNA Bifunctional Intercalators 2. Fluorescence Properties and DNA Binding Interaction of an Ethidium Homodimer and an Acridine Ethidium Heterodimer", Biochemistry vol. 17 No. 24 1978, 5078-5088.
Georgi, Ann et al., "Detection of Individual Fluorescently Labeled Reovirions in Living Cells", Proceedings of the National Academy of Sciences (PNAS) vol. 87 1990, 6579-6583.
Heller, A., "Electrical Wiring of Redox Enzymes", Acc. Chem. Res. vol. 23, No. 5 1990, 128-134.
Heravi, M M. et al., "Heterocyclic monoazo dyes derived from 2-(paminophenyhoxazolo-[4,5-b]pyridine and 7-(p-aminophenyl)-4H-[1,3,4]thiadiazolo-[2,3-c][1,2,4]triazin-4-one", Indian J. Chem. 36B 1997, 1025-1029.
Hickman, David T. et al., "Kinetically selective binding of single stranded RNA over DNA by a pyrrolidine-amide oligonucleotide minic (POM)", Nucleosides Nucleotides & Nucleic Acids vol. 20, No. 4-7 2001, 1169-1172.
Holskin, B. P. et al., "A continuous fluorescence-based assay of human cytomegalovirus protease using a peptide substrate", Analytical Biochemistry vol. 226 1995, 148-55.
Jensen, O. N. et al., "Mass Spectrometric Identification and Microcharacterization of Proteins from Electrophoretic Gels: Strategies and Applications.", Proteins Suppl 2 1998, 74-89.
Joshi, S. et al., "ATP Synthase complex from Bovine Heart Mitochondria. Subunit Arrangements as Revealed by Nearest Analysis and Susceptibility to Trypsin", The Journal of Biological Chemistry vol. 256, No. 24 1990, 14518-14525.
Jung, S. M. et al., "Crosslinking of Platelet Glycoprotein lb by N-Succinimidyl (4-azidophenyldithio) Propionate and 3, 3'-dithiobis (Sulfosuccinimidyl Promionate)", Biochimica et Biophysica Acta 761 1983, 152-162.
Kaufmann, Hitto et al., "Use of Antibodies for Detection of Phosphorylated Proteins Separated by Two-Dimensional Gel Electrophoresis", Proteomics vol. 1, No. 2 2001, 194-199.
Khanna, Ish K. et al., "Facile, Regioselective Synthesis of N-Alkylated 2,3-Diaminopyridines and Imidazo[4,5-b]pyridines", J. Orq. Chem. vol. 60 1995, 960-965.
Malone, James P. et al., "Practical aspects of fluorescent staining for proteomic applications.", Electrophoresis vol. 22 No. 5 2001, 919-32.
Markovits, et al., "Ethidium Dimer: A New Reagent for the Fluorimetric Determination of Nucleic Acids", Analytical Biochemistry vol. 94 1979, 259-269.
Markovits, J et al., "Dynamic Structure of DNA Complexes. Fluorometric Measurement of Hydrogen-Deuterium Exchange Kinetics of DNA-bound Ethidium Dimer and Acridine-Ethidium Dimer", Biochemistry vol. 22, No. 13 1983, 3231-3237.
Markovits, Judith et al., "Effect of B-Z transition and nucleic add structure on the conformational dynamics of bound ethidium dimer measured by hydrogen deuterium exchange kinetics", Nucl. Acids Res. 13 1985, 3773-3788.
Matayoshi, Edmund D. et al., "Novel Fluorogenic Substrates for Assaying Retroviral Proteases by Resonance Energy Transfer", Science vol. 247 1990, 954-958.
Morrison, Larry E., "Detection of Energy Transfer and Fluorescence Quenching", Nonisotopic DNA Probe Techniques L. Kricka, ed. 1992, 311-352.

Park, Linda S. et al., "Characterization of the Cell Surface Receptor for a Multi-Lineage Colony-Stimulating Factor (CSF-2alpha)*", *The Journal of Biological Chemistry* vol. 261, No. 1 1986, 205-210.

Pennington, M. W. et al., "Synthesis of fluorogenic interleukin-1 beta converting enzyme substrate based on resonance energy transfer", *Pep. Res.* vol. 7, No. 2 1994, 72-76.

Petric, A et al., "Azido-Tetrazolo Isomerizations of Some Thiazolopyridines (1)", *J. Heterocyclin Chem.* vol. 14 Oct. 1977, 1045-1047.

Przhiyalgovskaya, N. M. et al., "Carbocyanine Dyes with an O-hydroxyaryl Substituent in the Meso Position of the Polymethine Chain", *Translated from Khimiya Geterotsiklicheskikh Soedinenii* No. 1, pp. 100-103 1988, 83-86.

Raju, B. et al., "A fluorescent indicator for measuring cytosolic free magnesium", *Am. J. Physiol.* vol. 256 1989, C540-0548.

Rye, Hays S. et al., "High-sensitivity two-color detection of double-stranded DNA with a confocal fluorescence gel scanner using ethidium homodimer and thiazole orange", *Nucleic Acids Res* vol. 19 No. 2 1990, 327-333.

Saikachi, Haruo et al., "Studies on Compounds Related to Pyrazine. III. Synthesis of 2-Substituted Thiazolo[b]quinozaline.", *Chem. & Pharm. Bull.* vol. 9, No. 12 Dec. 1961, 941-944.

Sandler, Stanley R. et al., *Organic Functional Group Preparations* vol. 3, New York: Academic Press 1972, 5-7.

Schobel, Uwe et al., "New Donor-Acceptor Pair for Fluorescent Immunoassays by Energy Transfer", *Bioconjugate Chem.* vol. 10 Oct. 9, 1999, 1107-1114.

Selvin, Paul R., "Fluorescence Resonance Energy Transfer", *Methods in Enzymology* vol. 246, Academic Press Inc. 1995, 300-334.

Shevchenko, A. et al., "Mass Spectrometric Sequencing of Proteins Silver-Stained Polyacrylamide Gels", *Anal Chem* 68(5) 1996, 850-8.

Singh, Tara et al., "AntimalarialsDistal Hydrazine derivatives of 7-chloroquinoline", *Journal of medicinal chemistry* vol. 14, No. 6 1971, 532-5.

Smith, Keith et al., "Convenient synthesis of 4-aminopyridine-3-thiol and several thiazolo[5,4-c]pyridines via direct ligation", *Chemistry and Industry* vol. 9 May 2, 1988, 302-303.

Smith, Keith et al., "The synthesis of 2-substituted thiazolo[5,4-c]pyridines via directed methalation", *Sulfur Letters* vol. 17, No. 4 1994, 197-216.

Spatola, Arno F., "Ch 5: Peptide Backbone Modifications: A Structure - Activity Analysis of Peptides Containing Amide Bond Surrogates, Conformational Constraints, and Rela", *Chemistry and Biochemistry of Amino Acids, Peptides And Proteins*, vol. 7 1983, 267-357.

Staerk, Dan et al., "Bisintercalation of homodimeric thiazole orange dyes in DNA: Effect of modifying the linker", *Bioconjugate Chemistry* vol. 8, No. 6 Nov. 1997, 869-877.

Steinberg, Thomas H. et al., "Rapid and Simple Single Nanogram Detection of Glycoproteins in Polycralamide Gels and on Electroblots", *Proteomics* vol. 1, No. 72001, 841-855.

Steinberg, Thomas H. et al., "Global Quantitative Phosphoprotein Analysis Using Multiplexed Proteomics Technology", *Proteomics* vol. 3 Jul. 2003, 1128-1144.

STN International, "Accession No. 1959:5447", *CAPLUS Database Reg.* Nos. 108519-76-2 and 109724-08-5 2006.

Stratagene Catalog, "Gene Characterization Kits", 1988, 39.

Timtcheva, I. et al., "Homodimeric monomethine cyanine dyes as fluorescent probes of biopolymers", *Journal of Photochemistry and Photobiology B Biology* vol. 58, No. 2-3 Nov. 2000, 130-135.

Turner, James A., "Regiospecific electrophilic substitution of aminopyridines: ortho lithiation of 2-, 3-, and 4-(pivaloylamino)pyridines", *Journal of Organic Chemistry* vol. 48 1983, 3401-3408.

Tyagi, Sanjay et al., "Molecular Beacons : Probes that fluoresce upon Hybridization", *Nature Biotechnology* vol. 14 1996, 303-308.

Tyagi, Sanjay et al., "Multicolor molecular beacons for allele discrimination", *Nature Biotechnology* vol. 16, No. 1 1998, 49-53.

Vambutas, Vida et al., "Chloride-driven 3,3'-dipropylthiodicarbocyanine (DiSC3-(5)) and tetraphenylphosphonium cation (TPP+) uptake by thylakoids: inhibition of uptake by antibodies raised to the major polypeptides of the chloride efflux active particle(s)", *Biochimica et Biophysica Acta* vol. 893 1987, 69-74.

Wang, Q. M. et al., "Development of a conscious fluorescence assay for rhinovirus 14 3C protease using synthetic peptides", *Antiviral Chemistry & Chemotherapy* vol. 8, No. 4 1997, 303-310.

Wu, Pengguang et al., "Resonance Energy Transfer: Methods and Applications", *Analytical Biochemistry* vol. 218, No. 11994, 1-13.

Yamana, Kazushige et al., "Bis-pyrene-labeled oligonucleotide: sequence specificity of excimer and monomer fluorescence changes upon hybridization with DNA", *Bioconjug Chem* vol. 13, No. 62002, 1266-73.

Yamana, Kazushige et al., "Fluorescence Detection of Specific RNA Sequence Using 2'-Pyrene-Modified Oligoribonucleotides", *Angewandte Chemie International Edition in English* vol. 40 No. 6 2001, 1104-1106.

Yan, J. X. et al., "Protein Phosphorylation: Technologies for the Identification of Phosphoamino Acids", *J Chromatogr A* 808(1-2) 1998, 23-41.

CYANINE DYE COMPOUNDS

CROSS-REFERENCE TO RELATED APPLICATIONS

This application is a divisional of U.S. Ser. No. 11/005,860, filed Dec. 6, 2004, which claims priority to U.S. Ser. No. 60/527,234, filed Dec. 5, 2003; and U.S. Ser. No. 60/554,472 filed Mar. 18, 2004, which disclosures are herein incorporated by reference.

FIELD OF THE INVENTION

The present invention relates to cyanine compounds useful for staining nucleic acids, including DNA. The invention has applications in the fields of molecular biology, particularly with respect to fluorescence-based assays.

BACKGROUND OF THE INVENTION

In selected fields of life sciences research, including for example biological, biomedical, genetic, fermentation, aquaculture, agricultural, forensic and environmental research, there may often occur the need to identify nucleic acids, qualitatively and quantitatively, in pure solutions and in biological samples. Such applications may benefit from fast, sensitive, and selective methodologies for detecting and/or quantifying nucleic acids of interest.

In particular, it may be helpful in some research venues to provide molecular species that at least somewhat selectively stain DNA even in the presence of RNA. That is, the probe or reagent may permit the researcher to distinguish DNA present in a sample from RNA in the same sample.

SUMMARY

Embodiments of the present invention provide nucleic acid reporter compounds having at least one negatively charged substituent at a physiological pH. These reporter compounds find use as nucleic acid stains, particularly for the fluorescent detection/quantitation of DNA.

In one embodiment, the nucleic acid reporter molecules have the formula:

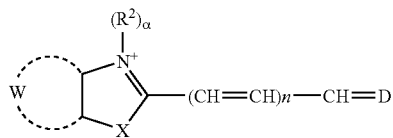

wherein W represents the atoms necessary to form one or two fused substituted 5- or 6-membered aromatic rings or one or two unsubstituted 5- or 6-membered aromatic rings. In one aspect W comprises —C, —$CR^1$, or —$N(R^2)_\beta$; wherein $\beta$ is 0 or 1, provided that $\alpha+\beta=1$; and each $R^1$ is independently hydrogen, a reactive group, a carrier molecule, a solid support, carboxy, sulfo, phosphate, phosphonate, amino, hydroxy, substituted aryl, unsubstituted aryl, substituted heteroaryl, unsubstituted heteroaryl, trifluoromethyl, halogen, substituted alkyl, unsubstituted alkyl, alkoxy, substituted alkylamino, unsubstituted alkylamino, substituted dialkylamino, or unsubstituted dialkylamino.

$R^2$ is a substituted alkyl, unsubstituted alkyl, substituted arylalkyl, unsubstituted arylalkyl, substituted heteroalkyl, unsubstituted heteroalkyl, alkoxy, carboxy, carboxyalkyl, hydroxy, hydroxyalkyl, sulfo, sulfoalkyl, amino, aminoalkyl, alkylamino, dialkylamino, or trialkylammonium.

In one aspect at least one of $R^1$ and $R^2$ is a negatively charged moiety, which are selected from the group consisting of sulfo, carboxy, phosphate, phosphonate, an alkyl group substituted by sulfo, an alkyl group substituted by a carboxy, an alkyl group substituted by phosphate, or an alkyl group substituted by phosphonate.

$\alpha$ is 0 or 1; n is 0 or 1; X is O, S, or Se; and

D is a substituted pyridinium, unsubstituted pyridinium, substituted quinolinium, or unsubstituted quinolinium moiety.

In an exemplary embodiment D has the formula:

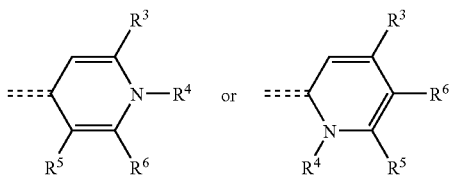

wherein $R^3$, $R^4$, $R^5$, and $R^6$ are independently hydrogen, substituted alkyl, unsubstituted alkyl, substituted heteroalkyl, unsubstituted heteroalkyl, substituted aryl, unsubstituted aryl, substituted arylalkyl, unsubstituted arylalkyl, substituted heteroarylalkyl; unsubstituted heteroarylalkyl, substituted heteroaryl, unsubstituted heteroaryl, substituted cycloalkyl, unsubstituted cycloalkyl, substituted heterocycloalkyl, unsubstituted heterocycloalkyl, halogen, alkoxy, substituted alkylamino, unsubstituted alkylamino, substituted alkylthio, unsubstituted alkylthio, reactive group, solid support, or carrier molecule. Alternatively, a member selected from $R^5$ in combination with $R^6$; $R^4$ in combination with $R^5$; $R^4$ in combination with $R^3$; $R^4$ in combination with $R^6$; $R^3$ in combination with $R^6$, together with the atoms to which they are joined, form a ring which is a 5-, 6- or 7-membered heterocycloalkyl, a substituted 5-, 6- or 7-membered heterocycloalkyl, a 5-, 6- or 7-membered cycloalkyl, a substituted 5-, 6- or 7-membered cycloalkyl, a 5-, 6- or 7-membered heteroaryl, a substituted 5-, 6- or 7-membered heteroaryl, a 5-, 6- or 7-membered aryl or a substituted 5-, 6- or 7-membered aryl.

In an exemplary embodiment, the present reporter molecules have the formula:

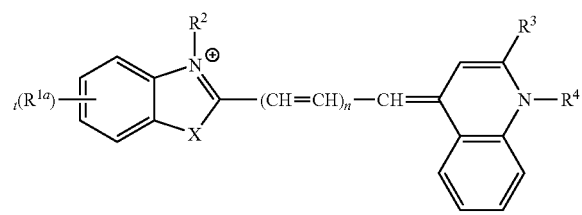

or the formula

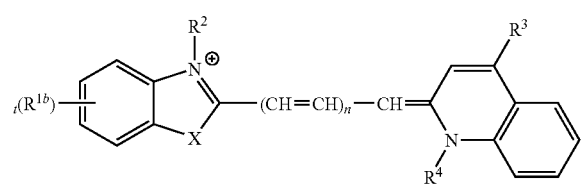

wherein each $R^{1a}R^{1b}$ are independently hydrogen, carboxy, sulfo, phosphate, phosphonate, amino, hydroxyl, trifluoromethyl, halogen, alkyl, substituted alkyl, alkoxy, alkylamino, substituted alkylamino, dialkylamino, substituted dialkylamino, fused benzene, substituted fused benzene, trifluomethyl, halogen, reactive group, solid support or carrier molecule.

Additional embodiments of the present invention provide methods of detecting the presence or absence of nucleic acid, including method for detecting the presence or absence of DNA in the presence of RNA. The present methods comprise:
a. combining a present nucleic acid reporter molecule with the sample to prepare a labeling mixture;
b. incubating the labeling mixture for a sufficient amount of time for the nucleic acid reporter molecule to associate with nucleic acid in the sample to form an incubated mixture;
c. illuminating the incubated sample with an appropriate wavelength to form an illuminated mixture; and,
d. observing the illuminated mixture whereby the presence or absence of the nucleic acid in a sample is detected.

Also provided is a staining solution comprising a present nucleic acid reporter molecule and a detergent. The detergent is typically present in an aqueous solution at a concentration from about 0.01% to about 0.5%. Detergents include CHAPTS, Triton-X, SDS and Tween 20.

Further embodiments provide complexes of the present compounds non-covalently associated with nucleic acid and compositions comprising a present compound and a sample. In one aspect the sample comprises biological fluids, buffer solutions, live cells, fixed cells, eukaryotic cells, prokaryotic cells, nucleic acid polymers, nucleotides, nucleosides, a polymeric gel or tissue sections. In a further aspect the sample is present in an aqueous solution, in or on a microarray or a microwell plate.

Additional embodiments of the present invention provide kits for the detection of nucleic acid, wherein the kit comprises any compound of the present invention. In a further embodiment, the kits comprise instructions for the detection of nucleic acid, particularly instructions for the detection of DNA in the presence of RNA. In yet another further embodiment, the kits comprises at least one component that is a sample preparation reagent, a buffering agent, an organic solvent, an aqueous nucleic acid reporter molecule dilution buffer, nucleic acid control, or an additional detection reagent.

BRIEF DESCRIPTION OF THE FIGURES

FIG. 3 indicates that in solution Compound 25 either does not bind RNA or binds RNA with little to no fluorescent signal intensity which is confirmed by the same fluorescence intensity signal for the RNA+DNA as for the corresponding DNA concentration, as described in Example 33.

DETAILED DESCRIPTION OF THE INVENTION

Definitions

Figure 1:
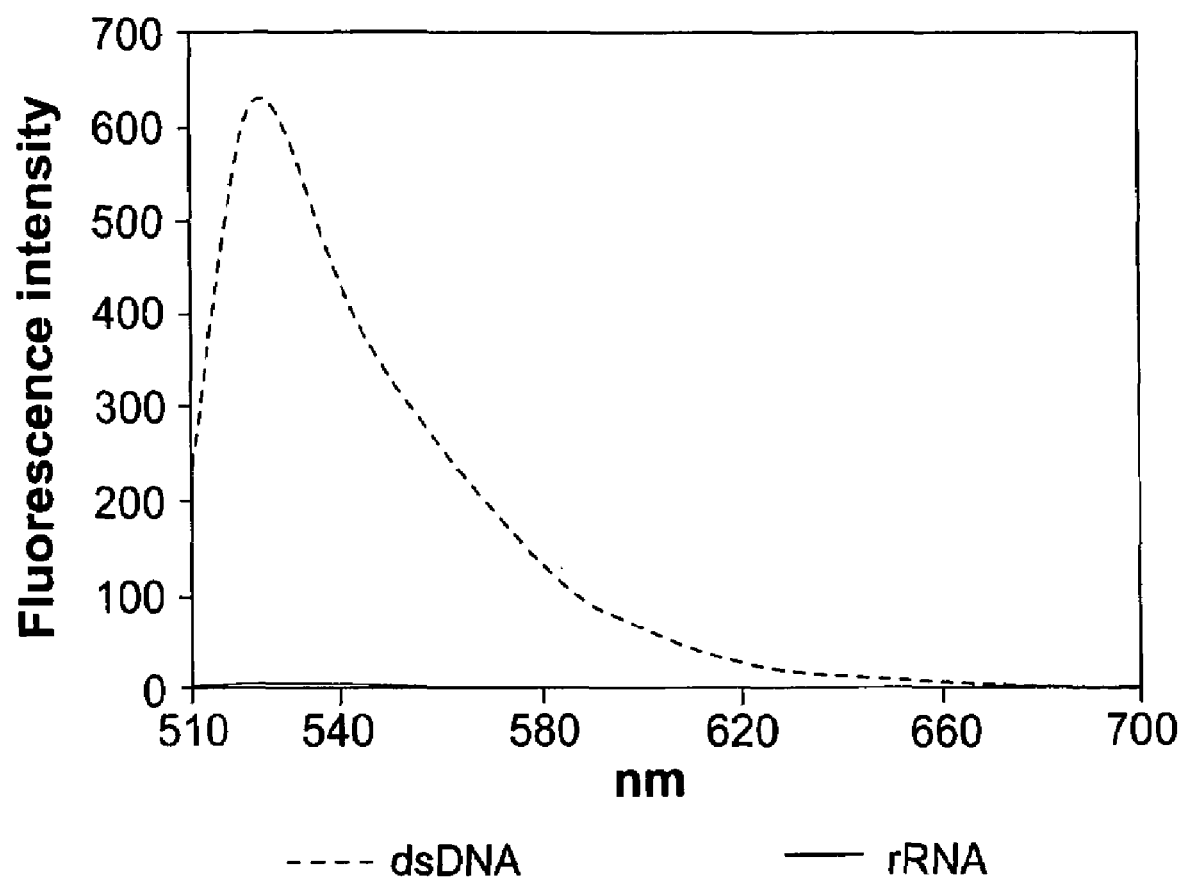
FIG. 1: A plot showing the fluorescence emission intensity of Compound 25 bound to rRNA and DNA (calf thymus), respectively, with excitation at 500 nm, as described in Example 31.

Before describing the present invention in detail, it is to be understood that this invention is not limited to specific compositions or process steps, as such may vary. It must be noted that, as used in this specification and the appended claims, the singular form "a", "an" and "the" include plural referents unless the context clearly dictates otherwise. Thus, for example, reference to "a compound" includes a plurality of compounds and reference to "a nucleic acid" includes a plurality of nucleic acids and the like.

Unless defined otherwise, all technical and scientific terms used herein have the same meaning as commonly understood by one of ordinary skill in the art to which this invention is related. The following terms are defined for the purposes of understanding the present disclosure.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds described herein may be prepared as a single isomer (e.g., enantiomer, cis-trans, positional, diastereomer) or as a mixture of isomers. In a preferred embodiment, the compounds are prepared as substantially a single isomer. Methods of preparing substantially isomerically pure compounds are known in the art. For example, enantiomerically enriched mixtures and pure enantiomeric compounds can be prepared by using synthetic intermediates that are enantiomerically pure in combination with reactions that either leave the stereochemistry at a chiral center unchanged or result in its complete inversion. Alternatively, the final product or intermediates along the synthetic route can be resolved into a single stereoisomer. Techniques for inverting or leaving unchanged a particular stereocenter, and those for resolving mixtures of stereoisomers are well known in the art and it is well within the ability of one of skill in the art to choose and appropriate method for a particular situation. See, generally, Furniss et al. (eds.), VOGEL'S ENCYCLOPEDIA OF PRACTICAL ORGANIC CHEMISTRY $5^{TH}$ ED., Longman Scientific and Technical Ltd., Essex, 1991, pp. 809-816; and Heller, Acc. Chem. Res. 23:128 (1990).

The compounds disclosed herein may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention.

Where a disclosed compound includes a conjugated ring system, resonance stabilization may permit a formal electronic charge to be distributed over the entire molecule. While a particular charge may be depicted as localized on a particular ring system, or a particular heteroatom, it is commonly understood that a comparable resonance structure can be drawn in which the charge may be formally localized on an alternative portion of the compound.

Selected compounds having a formal electronic charge may be shown without an appropriate biologically compatible counterion. Such a counterion serves to balance the positive or negative charge present on the compound. As used herein, a substance that is biologically compatible is not toxic as used, and does not have a substantially deleterious effect on biomolecules. Examples of negatively charged counterions include, among others, chloride, bromide, iodide, sulfate, alkanesulfonate, arylsulfonate, phosphate, perchlorate, tetrafluoroborate, tetraarylboride, nitrate and anions of aromatic or aliphatic carboxylic acids. Preferred counterions may include chloride, iodide, perchlorate and various sulfonates. Examples of positively charged counterions include, among others, alkali metal, or alkaline earth metal ions, ammonium, or alkylammonium ions.

Where substituent groups are specified by their conventional chemical formulae, written from left to right, they equally encompass the chemically identical substituents, which would result from writing the structure from right to left, e.g., —CH$_2$O— is intended to also recite —OCH$_2$—.

The term "acyl" or "alkanoyl" by itself or in combination with another term, means, unless otherwise stated, a stable straight or branched chain, or cyclic hydrocarbon radical, or combinations thereof, consisting of the stated number of carbon atoms and an acyl radical on at least one terminus of the alkane radical. The "acyl radical" is the group derived from a carboxylic acid by removing the —OH moiety therefrom.

The term "affinity" as used herein refers to the strength of the binding interaction of two molecules, such as a nucleic acid polymer and an intercalating agent or a positively charged moiety and a negatively charged moiety.

The term "alkyl," by itself or as part of another substituent means, unless otherwise stated, a straight or branched chain, or cyclic hydrocarbon radical, or combination thereof, which may be fully saturated, mono- or polyunsaturated and can include divalent ("alkylene") and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl".

Exemplary alkyl groups of use in the present invention contain between about one and about twenty five carbon atoms (e.g. methyl, ethyl and the like). Straight, branched or cyclic hydrocarbon chains having eight or fewer carbon atoms will also be referred to herein as "lower alkyl". In addition, the term "alkyl" as used herein further includes one or more substitutions at one or more carbon atoms of the hydrocarbon chain fragment. The term "amino" or "amine group" refers to the group —NR'R" (or NRR'R") where R, R' and R" are independently selected from the group consisting of hydrogen, alkyl, substituted alkyl, aryl, substituted aryl, aryl alkyl, substituted aryl alkyl, heteroaryl, and substituted heteroaryl. A substituted amine being an amine group wherein R' or R" is other than hydrogen. In a primary amino group, both R' and R" are hydrogen, whereas in a secondary amino group, either, but not both, R' or R" is hydrogen. In addition, the terms "amine" and "amino" can include protonated and quaternized versions of nitrogen, comprising the group —NRR'R" and its biologically compatible anionic counterions.

The term "aryl" as used herein refers to cyclic aromatic carbon chain having twenty or fewer carbon atoms, e.g., phenyl, naphthyl, biphenyl, and anthracenyl. One or more carbon atoms of the aryl group may also be substituted with, e.g., alkyl; aryl; heteroaryl; a halogen; nitro; cyano; hydroxyl, alkoxyl or aryloxyl; thio or mercapto, alkyl-, or arylthio; amino, alkylamino, arylamino, dialkyl-, diaryl-, or arylalkylamino; aminocarbonyl, alkylaminocarbonyl, arylaminocarbonyl, dialkylaminocarbonyl, diarylaminocarbonyl, or arylalkylaminocarbonyl; carboxyl, or alkyl- or aryloxycarbonyl; aldehyde; aryl- or alkylcarbonyl; iminyl, or aryl- or alkyliminyl; sulfo; alkyl- or alkylcarbonyl; iminyl, or aryl- or alkyliminyl; sulfo; alkyl- or arylsulfonyl; hydroximinyl, or aryl- or alkoximinyl. In addition, two or more alkyl or heteroalkyl substituents of an aryl group may be combined to form fused aryl-alkyl or aryl-heteroalkyl ring systems (e.g., tetrahydronaphthyl). Substituents including heterocyclic groups (e.g., heteroaryloxy, and heteroaralkylthio) are defined by analogy to the above-described terms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a straight or branched chain, or cyclic carbon-containing radical, or combinations thereof, consisting of the stated number of carbon atoms and at least one heteroatom selected from the group consisting of O, N, Si, P, S, and Se and wherein the nitrogen, phosphorous, sulfur, and selenium atoms are optionally oxidized, and the nitrogen heteroatom is optionally be quaternized. The heteroatom(s) O, N, P, S, Si, and Se may be placed at any interior position of the heteroalkyl group or at the position at which the alkyl group is attached to the remainder of the molecule. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$,—S(O)—CH$_3$,—CH$_2$—CH$_2$—S(O)$_2$—CH$_3$, —CH═CH—O—CH$_3$, —Si(CH$_3$)$_3$, —CH$_2$—CH═N—OCH$_3$, and —CH═CH—N(CH$_3$)—CH$_3$. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "aryl" means, unless otherwise stated, a polyunsaturated, aromatic moiety that can be a single ring or multiple rings (preferably from 1 to 3 rings), which are fused together or linked covalently. The term "heteroaryl" refers to aryl groups (or rings) that contain from one to four heteroatoms selected from N, O, S, and Se, wherein the nitrogen, sulfur, and selenium atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, tetrazolyl, benzo[b]furanyl, benzo[b]thienyl, 2,3-dihydrobenzo[1,4]dioxin-6-yl, benzo[1,3]dioxol-5-yl and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —OR', ═O, ═NR', ═N—OR', —NR'R", —SR', -halogen, —SiR'R"R'", —OC(O)R', —C(O) R', —CO$_2$R', —CONR'R", —OC(O)NR'R", —NR"C(O)R', —NR'—C(O)NR"R'", —NR"C(O)$_2$R', —NR—C(NR'R"R'")═NR'"', —NR—C(NR'R")═NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R'"' each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound includes more than one R group, for example, each of the R groups is independently selected as are each R', R", R'" and R'"' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O) CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: halogen, —OR', ═O, ═NR', ═N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")═NR'"', —NR—C(NR'R")═NR'", —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'" and R'"' are preferably independently selected from hydrogen, substituted or unsubstituted alkyl, substituted or unsubstituted heteroalkyl, substituted or unsubstituted aryl and substituted or unsubstituted heteroaryl. When a compound includes more than one R group, for example, each of the R groups is independently selected as are each R', R", R'" and R'"' groups when more than one of these groups is present. In the schemes that follow, the symbol X represents "R" as described above.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R''')$_d$—, where s and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted (C$_1$-C$_6$)alkyl.

As used herein, the term "heteroatom" includes oxygen (O), nitrogen (N), sulfur (S), phosphorus (P), silicon (Si), and selenium (Se).

The term "amino" or "amine group" refers to the group —NR'R" (or N$^+$RR'R") where R, R' and R" are independently selected from the group consisting of hydrogen, alkyl, substituted alkyl, aryl, substituted aryl, aryl alkyl, substituted aryl alkyl, heteroaryl, and substituted heteroaryl. A substituted amine being an amine group wherein R' or R" is other than hydrogen. In a primary amino group, both R' and R" are hydrogen, whereas in a secondary amino group, either, but not both, R' or R" is hydrogen. In addition, the terms "amine" and "amino" can include protonated and quaternized versions of nitrogen, comprising the group —N$^+$RR'R" and its biologically compatible anionic counterions.

The term "aqueous solution" as used herein refers to a solution that is predominantly water and retains the solution characteristics of water. Where the aqueous solution contains solvents in addition to water, water is typically the predominant solvent.

The term "Carboxyalkyl" as used herein refers to a group having the general formula —(CH$_2$)$_n$COOH wherein n is 1-18.

The term "carrier molecule" as used herein refers to a biological or a non-biological component that is covalently bonded to a compound of the present invention. Such components include, but are not limited to, an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell, a virus and combinations thereof.

The term "complex" as used herein refers to the association of two or more molecules, usually by non-covalent bonding.

The term "cyanine dye" as used herein refers to a fluorogenic compound that comprises 1) a substituted or unsubstituted benzazolium moiety, 2) a polymethine bridge and 3) a substituted or unsubstituted pyridinium or quinolinium moiety. These monomer or dye moieties are capable of forming a non-covalent complex with nucleic acid and demonstrating an increased fluorescent signal after formation of the nucleic acid-dye complex.

The term "detectable response" as used herein refers to a change in or an occurrence of, a signal that is directly or indirectly detectable either by observation or by instrumentation. Typically, the detectable response is an optical response resulting in a change in the wavelength distribution patterns or intensity of absorbance or fluorescence or a change in light scatter, fluorescence lifetime, fluorescence polarization, or a combination of the above parameters.

The term "kit" as used refers to a packaged set of related components, typically one or more compounds or compositions.

The term "Linker" or "L", as used herein, refers to a single covalent bond or a series of stable covalent bonds incorporating 1-20 nonhydrogen atoms selected from the group consisting of C, N, O, S and P that covalently attach the fluorogenic or fluorescent compounds to another moiety such as a chemically reactive group or a biological and non-biological component.

Exemplary linking members include a moiety that includes —C(O)NH—, —C(O)O—, —NH—, —S—, —O—, and the like. A "cleavable linker" is a linker that has one or more cleavable groups that may be broken by the result of a reaction or condition. The term "cleavable group" refers to a moiety that allows for release of a portion, e.g., a fluorogenic or fluorescent moiety, of a conjugate from the remainder of the conjugate by cleaving a bond linking the released moiety to the remainder of the conjugate. Such cleavage is either chemical in nature, or enzymatically mediated. Exemplary enzymatically cleavable groups include natural amino acids or peptide sequences that end with a natural amino acid.

In addition to enzymatically cleavable groups, it is within the scope of the present invention to include one or more sites that are cleaved by the action of an agent other than an enzyme. Exemplary non-enzymatic cleavage agents include, but are not limited to, acids, bases, light (e.g., nitrobenzyl derivatives, phenacyl groups, benzoin esters), and heat. Many cleaveable groups are known in the art. See, for example, Jung et al., *Biochem. Biophys. Acta*, 761: 152-162 (1983); Joshi et al., *J. Biol. Chem.*, 265: 14518-14525 (1990); Zarling et al., *J. Immunol.*, 124: 913-920 (1980); Bouizar et al., *Eur. J. Biochem.*, 155: 141-147 (1986); Park et al., *J. Biol. Chem.*, 261: 205-210 (1986); Browning et al., *J. Immunol.*, 143: 1859-1867 (1989). Moreover a broad range of cleavable, bifunctional (both homo- and hetero-bifunctional) spacer arms are commercially available.

An exemplary cleavable group, an ester, is cleavable group that may be cleaved by a reagent, e.g. sodium hydroxide, resulting in a carboxylate-containing fragment and a hydroxyl-containing product.

The linker can be used to attach the compound to another component of a conjugate, such as a targeting moiety (e.g., antibody, ligand, non-covalent protein-binding group, etc.), an analyte, a biomolecule, a drug and the like.

The term "negatively charged substituent", as used herein, refers to a functional group present on the nucleic acid reporter compound that exhibits a negative charge at physiological pH.

The term "nucleic acid" or "nucleic acid polymer" as used herein means DNA, RNA, single-stranded, double-stranded, or more highly aggregated hybridization motifs, and any chemical modifications thereof. Modifications include, but are not limited to, those providing chemical groups that incorporate additional charge, polarizability, hydrogen bonding, electrostatic interaction, and fluxionality to the nucleic acid ligand bases or to the nucleic acid ligand as a whole. Such modifications include, but are not limited to, peptide nucleic acids (PNAs), phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases, isocytidine and isoguanidine and the like. Nucleic acids can also include non-natural bases, such as, for example, nitroindole. Modifications can also include 3' and 5' modifications such as capping with a quencher, a fluorophore or another moiety.

The term "nucleic acid reporter molecule" as used herein refers to the present cyanine compounds that contain at least one group that is negatively charged at a physiological pH.

The term "reactive group" as used herein refers to a group that is capable of reacting with another chemical group to form a covalent bond, i.e. is covalently reactive under suitable reaction conditions, and generally represents a point of attachment for another substance. The reactive group is a moiety, such as carboxylic acid or succinimidyl ester, on the compounds of the present invention that is capable of chemically reacting with a functional group on a different compound to form a covalent linkage. Reactive groups generally include nucleophiles, electrophiles and photoactivatable groups.

Exemplary reactive groups include, but are not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides and the like. Methods to prepare each of these functional groups are well known in the art and their application to or modification for a particular purpose is within the ability of one of skill in the art (see, for example, Sandler and Karo, eds. ORGANIC FUNCTIONAL GROUP PREPARATIONS, Academic Press, San Diego, 1989).

The term "reporter molecule" as used herein refers to any luminescent molecule that is capable of associating with a nucleic acid polymer and producing a detectable signal. Typically, reporter molecules include unsymmetrical cyanine dyes, dimmers of cyanine dyes, ethidium bromide, DAPI, Hoechst, acridine and styryl dyes that are capable of producing a detectable signal upon appropriate wavelength excitation.

The term "salt thereof," as used herein includes salts of the agents of the invention and their conjugates, which are preferably prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of base addition salts include sodium, potassium, calcium, ammonium, organic amino, or magnesium, or a similar salt. When compounds of the present invention contain relatively basic functionalities, acid addition salts can be obtained by contacting the neutral form of such compounds with a sufficient amount of the desired acid, either neat or in a suitable inert solvent. Examples of addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

The term "sample" as used herein refers to any material that may contain nucleic acid. The sample may also include diluents, buffers, detergents, and contaminating species, debris and the like that are found mixed with the target. Illustrative examples include urine, sera, blood plasma, total blood, saliva, tear fluid, cerebrospinal fluid, secretory fluids and the like. Also included are solid, gel or substances such as mucus, body tissues, cells and the like suspended or dissolved in liquid materials such as buffers, extractants, solvents and the like. Typically, the sample is a live cell, a biological fluid that comprises endogenous host cell proteins, nucleic acid polymers, nucleotides, nucleosides, oligonucleotides, peptides and buffer solutions. The sample may be in an aqueous solution, a viable cell culture or immobilized on a solid or semi solid surface such as a polyacrylamide gel, membrane blot or on a microarray.

The term "solid support," as used herein, refers to a material that is substantially insoluble in a selected solvent system, or which can be readily separated (e.g., by precipitation) from a selected solvent system in which it is soluble. Solid supports useful in practicing the present invention can include groups that are activated or capable of activation to allow selected species to be bound to the solid support. Solid supports may be present in a variety of forms, including a chip, wafer or well, onto which an individual, or more than one compound, of the invention is bound such as a polymeric bead or particle.

The term "sulfoalkyl," as used herein, refers to a group having the general formula —$(CH_2)_nSO_3$ wherein n is 1-18.

The Compounds

In general, for ease of understanding the present invention, the nucleic acid reporter molecules and corresponding substituents will first be described in detail, followed by the many and varied methods in which the compounds find uses, which is followed by exemplified methods of use and synthesis of novel compounds that are particularly advantageous for use with the methods of the present invention.

The reporter compounds of the present disclosure typically exhibit a fluorescence enhancement when non-covalently associated with a nucleic acid. For selected compounds, the fluorescence enhancement is greater when the nucleic acid is DNA than when the nucleic acid is RNA.

In one embodiment the present invention provides nucleic acid complexing compounds that comprise at least one negatively charged moiety at physiological pH. Without wishing to be bound by a theory, it appears that typically the nucleic acid complexing compounds, when substituted by a negatively charged moiety, become groove binders instead of intercalating agents. Thus, negatively charged nucleic acid complexing compounds, while they appear to associate with both single and double stranded nucleic acid (RNA and/or DNA) they demonstrate an increased fluorescent enhancement when associated with double stranded nucleic acid, which is most prevalent as DNA. The nucleic acid complexing compounds include, without limitation, any compound known to one skilled in the art and novel compounds yet to be discovered, such as cyanine dyes, styryl dyes, ethidium bromide, DAPI, Hoechst and acridine. There is no intended limitation on the nucleic acid complexing compound.

A "negatively charged substituent", as used herein, refers to a functional group present on the reporter compound that exhibits a negative charge at physiological pH. Although physiological pH is about 7.4, it is understood that various organisms and biological components may be evaluated at higher or lower pH values, and that any pH that is compatible with the organism or biological component of interest may be considered a physiological pH. Similarly, any substituent that exhibits a negative charge at a pH level of interest is an appropriate negatively charged substituent for the purposes of this disclosure.

Any negatively charged substituent of the reporter compound may confer the desired nucleic acid selectivity on the reporter compound. In particular, preferred negatively charged substituents include, for example, sulfo, carboxy, phosphate, phosphonate, and hydroxy. The negatively charged substituent may be bound directly to the reporter compound, or may be bound via another substituent of the reporter compound. For example, the negatively charged substituent may be bound to the reporter compound via an alkyl group. Typically, the negatively charged substituent is a sulfo, carboxy, sulfoalkyl, or carboxyalkyl substituent.

Typically, the nucleic acid complexing compounds are unsymmetrical cyanine dyes including, but not limited to, any compound disclosed in U.S. Pat. Nos. 4,957,870; 4,883,867; 5,436,134; 5,658,751; 5,534,416 and 5,863,753, when substituted with a negatively charged moiety.

1. Cyanine Nucleic Acid Reporter Molecules

In one embodiment, the cyanine dye reporter compounds of the present disclosure may be described by the formula:

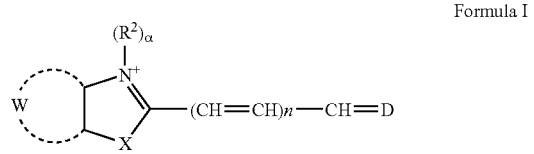

Formula I with the proviso that the compound is substituted by at least one negatively charged moiety at a physiological pH.

W represents the atoms necessary to form one to two fused 5- or 6-membered aromatic rings. The aromatic ring system represented by W is optionally substituted by any appropriate aryl group substituent, as described above, including reactive functional groups, solid supports, carrier molecules or covalent linkages.

Typically, the W ring system incorporates moieties selected from the group consisting of —C, —CR$^1$, and —N(R$^2$). Each of α and β is 0 or 1. Typically where β is 0, α is 1, and vice versa, so that α+β=1.

In one embodiment, W may incorporates four —CR$^1$ moieties to form a benzazolium ring system having the formula

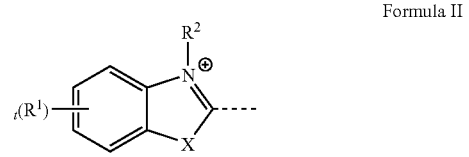

Formula II

The R$^1$ substituents may include any aryl group substituent, including additional fused 5- or 6-membered rings. Where each R$^1$ is independently hydrogen, carboxy, sulfo, phosphate, phosphonate, amino, hydroxyl, trifluoromethyl, halogen, alkyl, substituted alkyl, alkoxy, alkylamino, substituted alkylamino, dialkylamino, substituted dialkylamino, fused benzene, substituted fused benzene, trifluomethyl, halogen, reactive group, solid support or carrier molecule, wherein each alkyl portion of which is optionally substituted by alkyl group substituents, as described above. In particular, the alkyl groups substituents may be selected from the group consisting of carboxy, sulfo, phosphate, phosphonate, amino, and hydroxy. t is an integer from 1 to 4.

The R$^2$ substituent may include any aryl group substituent. R$^2$ may particularly be a substituted alkyl, unsubstituted alkyl, substituted arylalkyl, unsubstituted arylalkyl, substituted heteroalkyl, unsubstituted heteroalkyl, alkoxy, carboxy, carboxyalkyl, hydroxy, hydroxyalkyl, sulfo, sulfoalkyl, amino, aminoalkyl, alkylamino, dialkylamino, or trialkylammonium. The alkyl portion of which optionally incorporates up to six hetero atoms, selected from the group consisting of N, O and S; and which is optionally substituted one or more times by substituents selected from the group consisting of F, Cl, Br, I, hydroxy, carboxy, sulfo, phosphate, amino, sulfate, phosphonate, cyano, nitro, azido, $C_1$-$C_6$ alkoxy, $C_1$-$C_6$ alkylamino, $C_2$-$C_{12}$ dialkylamino, and $C_3$-$C_{18}$ trialkylammonium.

The value of n may be 0 or 1. Where n is 0, the reporter compound is a monomethine dye. Where n is 1, the reporter compound is a trimethine dye. Typically, n is 0.

The X moiety is selected from S, O, or Se, forming a benzothiazole, benzoxazole, or benzoselenazole heterocyclic ring system, respectively. Typically, X is S or O, and more typically, X is S.

The D moiety is a substituted or unsubstituted ring system, including pyridinium and quinolinium ring systems. For example, the D moiety may include the following ring systems (additional substituents omitted for clarity):

Formula III

Formula IV

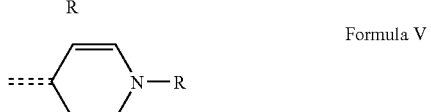

Formula V

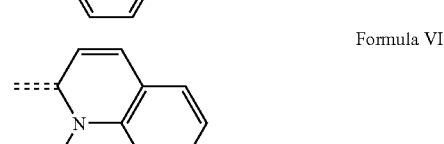

Formula VI

The D ring system is optionally further substituted by any aryl group substituent, as described above.

Typically, D will include a pyridinium or quinolinium ring system according to the formula

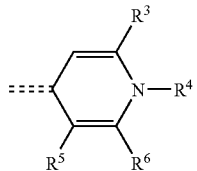

Formula VII or the formula

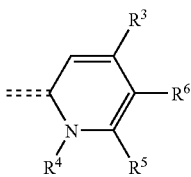

Formula VIII where $R^3$-$R^6$ may be selected from among aryl group substituents, or $R^5$ and $R^6$ taken in combination form a fused 6-membered aromatic ring to complete a quinolinium ring system. Alternatively a member selected from $R^5$ in combination with $R^6$; $R^4$ in combination with $R^5$; $R^4$ in combination with $R^3$; $R^4$ in combination with $R^6$; and $R^3$ in combination with $R^6$ together with the atoms to which they are joined, form a ring which is a 5-, 6- or 7-membered heterocycloalkyl, a substituted 5-, 6- or 7-membered heterocycloalkyl, a 5-, 6- or 7-membered cycloalkyl, a substituted 5-, 6- or 7-membered cycloalkyl, a 5-, 6- or 7-membered heteroaryl, a substituted 5-, 6- or 7-membered heteroaryl, a 5-, 6- or 7-membered aryl or a substituted 5-, 6- or 7-membered aryl.

More particularly, each of $R^3$-$R^6$ may be hydrogen, substituted alkyl, unsubstituted alkyl, substituted heteroalkyl, unsubstituted heteroalkyl, substituted aryl, unsubstituted aryl, substituted arylalkyl, unsubstituted arylalkyl, substituted heteroarylalkyl; unsubstituted heteroarylalkyl, substituted heteroaryl, unsubstituted heteroaryl, substituted cycloalkyl, unsubstituted cycloalkyl, substituted heterocycloalkyl, unsubstituted heterocycloalkyl, halogen, alkoxy, substituted alkylamino, unsubstituted alkylamino, substituted alkylthio, unsubstituted alkylthio, reactive group, solid support, or carrier molecule. Where $R^5$ and $R^6$ complete a quinolinium ring system, the additional ring substituents may also be H, alkyl, heteroalkyl, aryl, arylalkyl, heteroarylalkyl; heteroaryl, cycloalkyl, heterocycloalkyl, halogen, alkoxy, alkylamino, alkylthio, or a reactive group.

Selected reporter compounds may include compounds where at least one of $R^3$ and $R^4$ is selected from the group consisting of alkyl, heteroalkyl, alkoxy, alkylthio, aryl, arylalkyl, heteroaryl, and heteroarylalkyl that is itself then optionally further substituted. More particularly, each of $R^3$ and $R^4$ may be selected from the group consisting of alkyl, phenyl, benzyl, alkylthio, indolyl, imidazolyl, and thiazolyl that is then optionally further substituted one or more times. In a particular example, each of $R^3$ and $R^4$ may be selected from the group consisting of H, alkyl, —$(CH_2)_a$-aryl, and —$(CH_2)_a$-heteroaryl, where a is 0-6 and the alkyl, aryl, and heteroaryl portions are optionally further substituted one or more times by alkyl or aryl group substituents, respectively.

In an exemplary embodiment, the present compounds have the formula

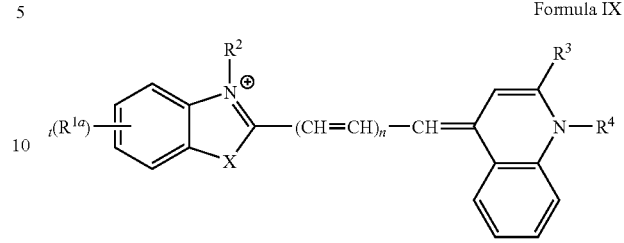

Formula IX or the formula

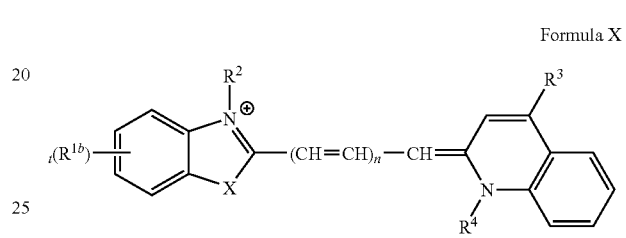

Formula X

Wherein each $R^{1a}$ and $R^{1b}$ are independently hydrogen, carboxy, sulfo, phosphate, phosphonate, amino, hydroxyl, trifluoromethyl, halogen, alkyl, substituted alkyl, alkoxy, alkylamino, substituted alkylamino, dialkylamino, substituted dialkylamino, fused benzene, substituted fused benzene, trifluomethyl, halogen, reactive group, solid support or carrier molecule and t is integer from 1 to 4

$R^2$ is a substituted alkyl, unsubstituted alkyl, substituted arylalkyl, unsubstituted arylalkyl, substituted heteroalkyl, unsubstituted heteroalkyl, alkoxy, carboxy, carboxyalkyl, hydroxy, hydroxyalkyl, sulfo, sulfoalkyl, amino, aminoalkyl, alkylamino, dialkylamino, or trialkylammonium.

$R^3$ and $R^4$ are independently hydrogen, substituted alkyl, unsubstituted alkyl, substituted heteroalkyl, unsubstituted heteroalkyl, substituted aryl, unsubstituted aryl, substituted arylalkyl, unsubstituted arylalkyl, substituted heteroarylalkyl; unsubstituted heteroarylalkyl, substituted heteroaryl, unsubstituted heteroaryl, substituted cycloalkyl, unsubstituted cycloalkyl, substituted heterocycloalkyl, unsubstituted heterocycloalkyl, halogen, alkoxy, substituted alkylamino, unsubstituted alkylamino, substituted alkylthio, unsubstituted alkylthio, reactive group, solid support, or carrier molecule.

In a further aspect, $R^4$ is hydrogen, alkyl, —$(CH_2)_a$-aryl, or —$(CH_2)_a$-heteroaryl, wherein a is an integer from 0 to about 6. In yet another aspect, $R^4$ is an alkyl, phenyl, benzyl, alkylthio, indolyl, imidazolyl, or thiazolyl.

Although the negatively charged substituent may be present at any position of the reporter molecule, in one aspect of the invention at least one of $R^1$ or $R^2$ comprises a negatively charged substituent, typically a sulfo, carboxy, phosphate, or phosphonate, or alkyl substituted by sulfo, carboxy, phosphate, or phosphonate.

Thus, in an exemplary embodiment, $R^1$ and $R^2$ of Formula IX or X, comprises a negatively charged substituent. Typically at least one of $R^1$ and $R^2$ is sulfo, carboxy, phosphate, phosphonate, an alkyl group substituted by sulfo, an alkyl group substituted by a carboxy, an alkyl group substituted by phosphate, or an alkyl group substituted by phosphonate.

Typically, the negatively charged substituent is a sulfo, carboxy, sulfoalkyl, or carboxyalkyl substituent.

Without wishing to be bound by theory, it is believed that the presence of one or more negatively charged substituents on the cyanine reporter compound may permit the tuning of selectivity and affinity of the resulting compound for particular nucleic acids. In particular, the presence of at least one negatively charged substituent may increase the selectivity and affinity of the resulting compound for DNA, when compared to the same compound when binding to RNA. The fluorescence enhancement of the resulting DNA complex may be greater than that of the corresponding RNA complex (see Example 31, Table 5).

Alternatively, the presence of at least one negatively charged substituent may increase the selectivity and affinity of the resulting compound for RNA, when compared to the same compound when binding to DNA. The fluorescence enhancement of the resulting RNA complex may be greater than that of the corresponding DNA complex (see Example 31, Table 6).

The selectivity of a given reporter compound for a particular nucleic acid type may be evaluated using screening methods for observing and quantifying such selectivity, such as are described in Examples 31-37.

The effect of particular negatively charged substituents, or substitution at particular positions, may be observed by comparing selected reporter compounds having a negatively charged substituent to corresponding compounds that do not have the negatively charged substituent. For example, as shown in Table 4, comparison of Compound 27 and Compound 30 shows that the addition of a sulfo group as an $R^1$ substituent may create a more than four-fold enhancement of fluorescence on DNA with respect to RNA. Similarly, a comparison of Compound 25 to Compound 29 shows that the addition of the same $R^1$ sulfo substituent creates a 26-fold enhancement of fluorescence on DNA with respect to RNA.

Selected compounds exhibiting selectivity for either DNA or RNA, as well as screening methods for identifying such selectivity, are described in Examples 1-36.

The compounds disclosed herein are readily modified to permit selectable alteration of the permeability, affinity, absorption, and emission properties (for specific examples, see U.S. Pat. No. 5,658,751, hereby incorporated by reference). The resulting compounds may be tailored to cover most of the visible and near-infrared spectrum.

Synthesis

The reporter compounds disclosed herein may be prepared by the treatment of an appropriately substituted benzazolium precursor with an appropriately substituted pyridinium or quinolinium precursor, and (where n=1) a source for the methine spacer.

Typically each precursor is selected so as to incorporate the desired and/or appropriate chemical substituents, or functional groups that may be converted to the desired and/or appropriate chemical substituents. The synthetic strategies and procedures that may be used to prepare and combine these precursors so as to yield the disclosed compounds is generally well understood by one skilled in the art, including a variety of post-synthetic modifications and variations thereof.

A wide variety of benzazolium derivatives suitable for use as a precursor compound have been described previously. If X is O, the precursor compound is a benzoxazolium; if X is S it is a benzothiazolium; and if X is Se it is a benzoselenazolium. The commercial availability of suitable starting materials and relative ease of synthesis may make compounds with X=O or S the preferred precursors.

The desired $R^1$ substituents are typically incorporated in the parent benzazole molecule prior to quaternization with an alkylating agent. $R^2$ is typically obtained by alkylation of the parent heterocycle with an alkylating agent. The alkylating reagent may be an alkyl halide such as ethyl iodide, an alkylsulfonate such as methyl p-toluenesulfonate or a cyclic sulfonate such as propanesultone or butanesultone.

In the synthesis of the reporter compounds, the second heterocyclic precursor is usually a pyridinium or quinolinium salt that is already appropriately substituted. Alternatively, substituents can be incorporated into the heterocyclic ring structure subsequent to attachment of the benzazolium portion of the dye.

The pyridine and quinoline precursors may be bound adjacent to the ring nitrogen (as for 2-pyridines and 2-quinolines) or may be bound at a point of attachment para to the ring nitrogen atom (as for 4-pyridines and 4-quinolines).

When n=0, the synthesis of monomethine dyes commonly utilizes precursors having a methyl substituent on one precursor, and a reactive "leaving group" that is typically methylthio or chloro, on the other substituent. Typically, the precursors include a methylthio and methyl substituent, respectively. The condensing reagent in the case of monomethine dyes is typically a base such as triethylamine or diisopropylethylamine.

Specific examples of benzazolium, pyridinium, and quinolinium intermediates that may be useful in completing the synthesis described above may be found in, for example, U.S. Pat. Nos. 5,436,134 and 5,658,751, each hereby incorporated by reference. Each pyridinium, quinolinium or benzazolium ring system may be fused to additional rings, resulting in dyes that absorb and emit at longer wavelengths (for example, see U.S. Pat. No. 6,027,709, hereby incorporated by reference).

Examples 1-30 describe the synthesis of selected reporter compounds. It will be appreciated that numerous changes and modifications in the described synthetic schemes may be adopted in order to prepare a particular desired reporter compound, without deviating from the general synthetic strategies described herein.

Reactive Groups, Carrier Molecules and Solid Supports

The present compounds, in certain embodiments, are chemically reactive wherein the compounds comprise a reactive group. In a further embodiment, the compounds comprise a carrier molecule or solid support. These substituents, reactive groups, carrier molecules, and solid supports, comprise a linker that is used to covalently attach the substituents to any of the moieties of the present compounds. The solid support, carrier molecule or reactive group may be directly attached (where linker is a single bond) to the moieties or attached through a series of stable bonds, as disclosed above.

Any combination of linkers may be used to attach the carrier molecule, solid support or reactive group and the present compounds together. The linker may also be substituted to alter the physical properties of the reporter moiety or chelating moiety, such as spectral properties of the dye. Examples of L include substituted or unsubstituted polyalkylene, arylene, alkylarylene, arylenealkyl, or arylthio moieties.

The linker typically incorporates 1-30 nonhydrogen atoms selected from the group consisting of C, N, O, S and P. The linker may be any combination of stable chemical bonds, optionally including, single, double, triple or aromatic carbon-carbon bonds, as well as carbon-nitrogen bonds, nitrogen-nitrogen bonds, carbon-oxygen bonds, sulfur-sulfur bonds, carbon-sulfur bonds, phosphorus-oxygen bonds, phosphorus-nitrogen bonds, and nitrogen-platinum bonds. Typically the linker incorporates less than 15 nonhydrogen atoms and are composed of any combination of ether, thioether, thiourea, amine, ester, carboxamide, sulfonamide, hydrazide bonds and aromatic or heteroaromatic bonds. Typically the linker is a combination of single carbon-carbon bonds and carboxamide, sulfonamide or thioether bonds. The bonds of the linker typically result in the following moieties that can be found in the linker: ether, thioether, carboxamide, thiourea, sulfonamide, urea, urethane, hydrazine, alkyl, aryl, heteroaryl, alkoxy, cycloalkyl and amine moieties. Examples of a linker include substituted or unsubstituted polymethylene, arylene, alkylarylene, arylenealkyl, and arylthio.

In one embodiment, the linker contains 1-6 carbon atoms; in another, the linker comprises a thioether linkage. Exemplary linking members include a moiety that includes —C(O)NH—, —C(O)O—, —NH—, —S—, —O—, and the like. In another embodiment, the linker is or incorporates the formula —$(CH_2)_d(CONH(CH_2)_e)_z$— or where d is an integer from 0-5, e is an integer from 1-5 and z is 0 or 1. In a further embodiment, the linker is or incorporates the formula —O—$(CH_2)$—. In yet another embodiment, the linker is or incorporates a phenylene or a 2-carboxy-substituted phenylene.

An important feature of the linker is to provide an adequate space between the carrier molecule, reactive group or solid support and the dye so as to prevent steric hinderance. Therefore, the linker of the present compound is important for (1) attaching the carrier molecule, reactive group or solid support to the compound, (2) providing an adequate space between the carrier molecule, reactive group or solid support and the compound so as not to sterically hinder the action of the compound and (3) for altering the physical properties of the present compounds.

In another exemplary embodiment of the invention, the present compounds are chemically reactive, and are substituted by at least one reactive group. The reactive group functions as the site of attachment for another moiety, such as a carrier molecule or a solid support, wherein the reactive group chemically reacts with an appropriate reactive or functional group on the carrier molecule or solid support.

Reactive groups or reactive group precursors may be positioned during the formation of the present compounds. Thus, compounds incorporating a reactive group can be reacted with and attached to a wide variety of biomolecules or non-biomolecules that contain or are modified to contain functional groups with suitable reactivity. When a labeled component includes a compound as disclosed herein, then this conjugate typically possesses the nucleic acid staining abilities of the parent compound, particularly DNA staining. However, the present fluorescent compounds can also function as reporter molecules for the labeled components wherein the nucleic acid binding properties of the reagents may not employed.

Preferred reactive groups for incorporation into the disclosed compounds may be selected to react with an amine, a thiol or an alcohol. In an exemplary embodiment, the compounds of the invention further comprise a reactive group that is an acrylamide, an activated ester of a carboxylic acid, a carboxylic ester, an acyl azide, an acyl nitrile, an aldehyde, an alkyl halide, an anhydride, an aniline, an amine, an aryl halide, an azide, an aziridine, a boronate, a diazoalkane, a haloacetamide, a haloalkyl, a halotriazine, a hydrazine, an imido ester, an isocyanate, an isothiocyanate, a maleimide, a phosphoramidite, a photoactivatable group, a reactive platinum complex, a silyl halide, a sulfonyl halide, and a thiol. In a particular embodiment the reactive group is selected from the group consisting of carboxylic acid, succinimidyl ester of a carboxylic acid, hydrazide, amine and a maleimide. In exemplary embodiment, at least one member selected from $R^1, R^{1a}, R^{1b}, R^2, R^3, R^4, R^5$, or $R^6$ comprises a reactive group. Preferably, at least one of $R^1$, $R^{1a}$, $R^{1b}$, or $R^2$ comprises a reactive group or is attached to a reactive group. Alternatively, if the present compound comprises a carrier molecule or solid support a reactive group may be covalently attached independently to those substituents, allowing for further conjugation to a another dye, carrier molecule or solid support.

In one aspect, the compound comprises at least one reactive group that selectively reacts with an amine group. This amine-reactive group is selected from the group consisting of succinimidyl ester, sulfonyl halide, tetrafluorophenyl ester and iosothiocyanates. Thus, in one aspect, the present compounds form a covalent bond with an amine-containing molecule in a sample. In another aspect, the compound comprises at least one reactive group that selectively reacts with a thiol group. This thiol-reactive group is selected from the group consisting of maleimide, haloalkyl and haloacetamide (including any reactive groups disclosed in U.S. Pat. Nos. 5,362,628; 5,352,803 and 5,573,904).

The pro-reactive groups are synthesized during the formation of the monomer moieties and carrier molecule and solid support containing compounds to provide chemically reactive compounds. In this way, compounds incorporating a reactive group can be covalently attached to a wide variety of carrier molecules or solid supports that contain or are modified to contain functional groups with suitable reactivity, resulting in chemical attachment of the components. In an exemplary embodiment, the reactive group of the compounds of the invention and the functional group of the carrier molecule or solid support comprise electrophiles and nucleophiles that can generate a covalent linkage between them. Alternatively, the reactive group comprises a photoactivatable group, which becomes chemically reactive only after illumination with light of an appropriate wavelength. Typically, the conjugation reaction between the reactive group and the carrier molecule or solid support results in one or more atoms of the reactive group being incorporated into a new linkage attaching the present compound of the invention to the carrier molecule or solid support. Selected examples of functional groups and linkages are shown in Table 1, where the reaction of an electrophilic group and a nucleophilic group yields a covalent linkage.

TABLE 1

Examples of some routes to useful covalent linkages

| Electrophilic Group | Nucleophilic Group | Resulting Covalent Linkage |
|---|---|---|
| activated esters* | amines/anilines | carboxamides |
| acrylamides | thiols | thioethers |
| acyl azides** | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |

TABLE 1-continued

Examples of some routes to useful covalent linkages

| Electrophilic Group | Nucleophilic Group | Resulting Covalent Linkage |
|---|---|---|
| anhydrides | amines/anilines | carboxamides |
| aryl halides | thiols | thiophenols |
| aryl halides | amines | aryl amines |
| aziridines | thiols | thioethers |
| boronates | glycols | boronate esters |
| carbodiimides | carboxylic acids | N-acylureas or anhydrides |
| diazoalkanes | carboxylic acids | esters |
| epoxides | thiols | thioethers |
| haloacetamides | thiols | thioethers |
| haloplatinate | amino | platinum complex |
| haloplatinate | heterocycle | platinum complex |
| haloplatinate | thiol | platinum complex |
| halotriazines | amines/anilines | aminotriazines |
| halotriazines | alcohols/phenols | triazinyl ethers |
| halotriazines | thiols | triazinyl thioethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

*Activated esters, as understood in the art, generally have the formula —COΩ, where Ω is a good leaving group (e.g., succinimidyloxy (—OC$_4$H$_4$O$_2$) sulfosuccinimidyloxy (—OC$_4$H$_3$O$_2$—SO$_3$H), -1-oxybenzotriazolyl (—OC$_6$H$_4$N$_3$); or an aryloxy group or aryloxy substituted one or more times by electron withdrawing substituents such as nitro, fluoro, chloro, cyano, or trifluoromethyl, or combinations thereof, used to form activated aryl esters; or a carboxylic acid activated by a carbodiimide to form an anhydride or mixed anhydride —OCOR$^a$ or —OCNR$^a$NHR$^b$, where R$^a$ and R$^b$, which may be the same or different, are C$_1$-C$_6$ alkyl, C$_1$-C$_6$ perfluoroalkyl, or C$_1$-C$_6$ alkoxy; or cyclohexyl, 3-dimethylaminopropyl, or N-morpholinoethyl).
**Acyl azides can also rearrange to isocyanates Choice of the reactive group used to attach the compound of the invention to the substance to be conjugated typically depends on the reactive or functional group on the substance to be conjugated and the type or length of covalent linkage desired. The types of functional groups typically present on the organic or inorganic substances (biomolecule or non-biomolecule) include, but are not limited to, amines, amides, thiols, alcohols, phenols, aldehydes, ketones, phosphates, imidazoles, hydrazines, hydroxylamines, disubstituted amines, halides, epoxides, silyl halides, carboxylate esters, sulfonate esters, purines, pyrimidines, carboxylic acids, olefinic bonds, or a combination of these groups. A single type of reactive site may be available on the substance (typical for polysaccharides or silica), or a variety of sites may occur (e.g., amines, thiols, alcohols, phenols), as is typical for proteins.

Typically, the reactive group will react with an amine, a thiol, an alcohol, an aldehyde, a ketone, or with silica. Preferably, reactive groups react with an amine or a thiol functional group, or with silica. In one embodiment, the reactive group is an acrylamide, an activated ester of a carboxylic acid, an acyl azide, an acyl nitrile, an aldehyde, an alkyl halide, a silyl halide, an anhydride, an aniline, an aryl halide, an azide, an aziridine, a boronate, a diazoalkane, a haloacetamide, a halotriazine, a hydrazine (including hydrazides), an imido ester, an isocyanate, an isothiocyanate, a maleimide, a phosphoramidite, a reactive platinum complex, a sulfonyl halide, or a thiol group. By "reactive platinum complex" is particularly meant chemically reactive platinum complexes such as described in U.S. Pat. No. 5,714,327.

Where the reactive group is an activated ester of a carboxylic acid, such as a succinimidyl ester of a carboxylic acid, a sulfonyl halide, a tetrafluorophenyl ester or an isothiocyanates, the resulting compound is particularly useful for preparing conjugates of carrier molecules such as proteins, nucleotides, oligonucleotides, or haptens. Where the reactive group is a maleimide, haloalkyl or haloacetamide (including any reactive groups disclosed in U.S. Pat. Nos. 5,362,628; 5,352,803 and 5,573,904 (supra)) the resulting compound is particularly useful for conjugation to thiol-containing substances. Where the reactive group is a hydrazide, the resulting compound is particularly useful for conjugation to periodate-oxidized carbohydrates and glycoproteins, and in addition is an aldehyde-fixable polar tracer for cell microinjection. Where the reactive group is a silyl halide, the resulting compound is particularly useful for conjugation to silica surfaces, particularly where the silica surface is incorporated into a fiber optic probe subsequently used for remote ion detection or quantitation.

In a particular aspect, the reactive group is a photoactivatable group such that the group is only converted to a reactive species after illumination with an appropriate wavelength. An appropriate wavelength is generally a UV wavelength that is less than 400 nm. This method provides for specific attachment to only the target molecules, either in solution or immobilized on a solid or semi-solid matrix. Photoactivatable reactive groups include, without limitation, benzophenones, aryl azides and diazirines.

Preferably, the reactive group is a photoactivatable group, succinimidyl ester of a carboxylic acid, a haloacetamide, haloalkyl, a hydrazine, an isothiocyanate, a maleimide group, an aliphatic amine, a silyl halide, a cadaverine or a psoralen. More preferably, the reactive group is a succinimidyl ester of a carboxylic acid, a maleimide, an iodoacetamide, or a silyl halide. In a particular embodiment the reactive group is a succinimidyl ester of a carboxylic acid, a sulfonyl halide, a tetrafluorophenyl ester, an iosothiocyanates or a maleimide.

The selection of a covalent linkage to attach the reporter molecule to the carrier molecule or solid support typically depends on the chemically reactive group on the component to be conjugated. The discussion regarding reactive groups in the section immediately preceding is relevant here as well. Exemplary reactive groups typically present on the biological or non-biological components include, but are not limited to, amines, thiols, alcohols, phenols, aldehydes, ketones, phosphates, imidazoles, hydrazines, hydroxylamines, disubstituted amines, halides, epoxides, sulfonate esters, purines, pyrimidines, carboxylic acids, or a combination of these groups. A single type of reactive site may be available on the component (typical for polysaccharides), or a variety of sites may occur (e.g. amines, thiols, alcohols, phenols), as is typical for proteins. A carrier molecule or solid support may be conjugated to more than one reporter molecule, which may be the same or different, or to a substance that is additionally modified by a hapten. Although some selectivity can be obtained by careful control of the reaction conditions, selectivity of labeling is best obtained by selection of an appropriate reactive compound.

In another exemplary embodiment, the present compound is covalently bound to a carrier molecule. If the compound has a reactive group, then the carrier molecule can alternatively be linked to the compound through the reactive group. The reactive group may contain both a reactive functional moiety and a linker, or only the reactive functional moiety.

A variety of carrier molecules are useful in the present invention. Exemplary carrier molecules include antigens, steroids, vitamins, drugs, haptens, metabolites, toxins, environmental pollutants, amino acids, peptides, proteins, nucleic acids, nucleic acid polymers, carbohydrates, lipids, and polymers. In exemplary embodiment, at least one member selected from $R^1$, $R^{1a}$, $R^{1b}$, $R^2$, $R^3$, $R^4$, $R^5$, or $R^6$ comprises a carrier molecule. Preferably, at least one of $R^1$, $R^{1a}$, $R^{1b}$, or $R^2$ comprises a carrier molecule or is attached to a carrier molecule. Alternatively, if the present compound comprises a reactive group or solid support a reactive group may be covalently attached independently to those substituents, allowing for further conjugation to a reactive group, carrier molecule or solid support.

In an exemplary embodiment, the carrier molecule comprises an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell, a virus and combinations thereof. In another exemplary embodiment, the carrier molecule is selected from a hapten, a nucleotide, an oligonucleotide, a nucleic acid polymer, a protein, a peptide or a polysaccharide. In a preferred embodiment the carrier molecule is amino acid, a peptide, a protein, a polysaccharide, a nucleoside, a nucleotide, an oligonucleotide, a nucleic acid, a hapten, a psoralen, a drug, a hormone, a lipid, a lipid assembly, a tyramine, a synthetic polymer, a polymeric microparticle, a biological cell, cellular components, an ion chelating moiety, an enzymatic substrate or a virus. In another preferred embodiment, the carrier molecule is an antibody or fragment thereof, an antigen, an avidin or streptavidin, a biotin, a dextran, an antibody binding protein, a fluorescent protein, agarose, and a non-biological microparticle. Typically, the carrier molecule is an antibody, an antibody fragment, antibody-binding proteins, avidin, streptavidin, a toxin, a lectin, or a growth factor. Preferred haptens include biotin, digoxigenin and fluorophores.

Antibody binding proteins include, but are not limited to, protein A, protein G, soluble Fc receptor, protein L, lectins, anti-IgG, anti-IgA, anti-IgM, anti-IgD, anti-IgE or a fragment thereof.

In an exemplary embodiment, the enzymatic substrate is selected from an amino acid, peptide, sugar, alcohol, alkanoic acid, 4-guanidinobenzoic acid, nucleic acid, lipid, sulfate, phosphate, —CH$_2$OCOalkyl and combinations thereof. Thus, the enzyme substrates can be cleave by enzymes selected from the group consisting of peptidase, phosphatase, glycosidase, dealkylase, esterase, guanidinobenzotase, sulfatase, lipase, peroxidase, histone deacetylase, endoglycoceramidase, exonuclease, reductase and endonuclease.

In another exemplary embodiment, the carrier molecule is an amino acid (including those that are protected or are substituted by phosphates, carbohydrates, or $C_1$ to $C_{22}$ carboxylic acids), or a polymer of amino acids such as a peptide or protein. In a related embodiment, the carrier molecule contains at least five amino acids, more preferably 5 to 36 amino acids. Exemplary peptides include, but are not limited to, neuropeptides, cytokines, toxins, protease substrates, and protein kinase substrates. Other exemplary peptides may function as organelle localization peptides, that is, peptides that serve to target the conjugated compound for localization within a particular cellular substructure by cellular transport mechanisms. Preferred protein carrier molecules include enzymes, antibodies, lectins, glycoproteins, histones, albumins, lipoproteins, avidin, streptavidin, protein A, protein G, phycobiliproteins and other fluorescent proteins, hormones, toxins and growth factors. Typically, the protein carrier molecule is an antibody, an antibody fragment, avidin, streptavidin, a toxin, a lectin, or a growth factor. Exemplary haptens include biotin, digoxigenin and fluorophores.

In another exemplary embodiment, the carrier molecule comprises a nucleic acid base, nucleoside, nucleotide or a nucleic acid polymer, optionally containing an additional linker or spacer for attachment of a fluorophore or other ligand, such as an alkynyl linkage (U.S. Pat. No. 5,047,519), an aminoallyl linkage (U.S. Pat. No. 4,711,955) or other linkage. In another exemplary embodiment, the nucleotide carrier molecule is a nucleoside or a deoxynucleoside or a dideoxynucleoside.

Exemplary nucleic acid polymer carrier molecules are single- or multi-stranded, natural or synthetic DNA or RNA oligonucleotides, or DNA/RNA hybrids, or incorporating an unusual linker such as morpholine derivatized phosphates (AntiVirals, Inc., Corvallis Oreg.), or peptide nucleic acids such as N-(2-aminoethyl)glycine units, where the nucleic acid contains fewer than 50 nucleotides, more typically fewer than 25 nucleotides.

In another exemplary embodiment, the carrier molecule comprises a carbohydrate or polyol that is typically a polysaccharide, such as dextran, FICOLL, heparin, glycogen, amylopectin, mannan, inulin, starch, agarose and cellulose, or is a polymer such as a poly(ethylene glycol). In a related embodiment, the polysaccharide carrier molecule includes dextran, agarose or FICOLL.

In another exemplary embodiment, the carrier molecule comprises a lipid (typically having 6-25 carbons), including glycolipids, phospholipids, and sphingolipids. Alternatively, the carrier molecule comprises a lipid vesicle, such as a liposome, or is a lipoprotein (see below). Some lipophilic substituents are useful for facilitating transport of the conjugated dye into cells or cellular organelles.

Alternatively, the carrier molecule is cells, cellular systems, cellular fragments, or subcellular particles. Examples of this type of conjugated material include virus particles, bacterial particles, virus components, biological cells (such as animal cells, plant cells, bacteria, or yeast), or cellular components. Examples of cellular components that can be labeled, or whose constituent molecules can be labeled, include but are not limited to lysosomes, endosomes, cytoplasm, nuclei, histones, mitochondria, Golgi apparatus, endoplasmic reticulum and vacuoles.

In another embodiment the carrier molecule is a metal chelating moiety. While any chelator that binds a metal ion of interest and gives a change in its fluorescence properties is a suitable conjugate, preferred metal chelating moieties are crown ethers, including diaryldiaza crown ethers, as described in U.S. Pat. No. 5,405,975 to Kuhn et al. (1995); derivatives of 1,2-bis-(2-aminophenoxyethane)-N,N,N',N'-tetraacetic acid (BAPTA), as described in U.S. Pat. No. 5,453,517 to Kuhn et al. (1995) (incorporated by reference) and U.S. Pat. No. 5,049,673 to Tsien et al. (1991); derivatives of 2-carboxymethoxy-aniline-N,N-diacetic acid (APTRA), as described by Ragu et al., *Am. J. Physiol.*, 256: C540 (1989); and pyridyl-based and phenanthroline metal ion chelators, as described in U.S. Pat. No. 5,648,270 to Kuhn et al. (1997).

Fluorescent conjugates of metal chelating moieties possess utility as indicators for the presence of a desired metal ion. While fluorescent ion-indicators are known in the art, the incorporation of the fluorinated fluorogenic and fluorescent compounds of the present invention imparts the highly advantageous properties of the instant fluorophores onto the resulting ion indicator.

The ion-sensing conjugates of the invention are optionally prepared in chemically reactive forms and further conjugated to polymers such as dextrans to improve their utility as sensors as described in U.S. Pat. Nos. 5,405,975 and 5,453,517.

In another exemplary embodiment, the carrier molecule non-covalently associates with organic or inorganic materials. Exemplary embodiments of the carrier molecule that possess a lipophilic substituent can be used to target lipid assemblies such as biological membranes or liposomes by non-covalent incorporation of the dye compound within the membrane, e.g., for use as probes for membrane structure or for incorporation in liposomes, lipoproteins, films, plastics, lipophilic microspheres or similar materials.

In an exemplary embodiment, the carrier molecule comprises a specific binding pair member wherein the present compounds are conjugated to a specific binding pair member and are used to detect an analyte in a sample. Alternatively, the presence of the labeled specific binding pair member indicates the location of the complementary member of that specific binding pair; each specific binding pair member having an area on the surface or in a cavity which specifically binds to, and is complementary with, a particular spatial and polar organization of the other. Exemplary binding pairs are set forth in Table 2.

TABLE 2

Representative Specific Binding Pairs

| | |
|---|---|
| antigen | antibody |
| biotin | avidin (or streptavidin or anti-biotin) |
| IgG* | protein A or protein G |
| drug | drug receptor |
| folate | folate binding protein |
| toxin | toxin receptor |
| carbohydrate | lectin or carbohydrate receptor |
| peptide | peptide receptor |
| protein | protein receptor |
| enzyme substrate | enzyme |
| DNA (RNA) | cDNA (cRNA)† |
| hormone | hormone receptor |
| ion | chelator |
| antibody | antibody-binding proteins |

*IgG is an immunoglobulin
†cDNA and cRNA are the complementary strands used for hybridization In an exemplary embodiment, the present compounds of the invention are covalently bonded to a solid support. The solid support may be attached to the compound or through a reactive group, if present, or through a carrier molecule, if present. In exemplary embodiment, at least one member selected from $R^1$, $R^{1a}$, $R^{1b}$, $R^2$, $R^3$, $R^4$, $R^5$, or $R^6$ comprises a solid support. Preferably, at least one of $R^1$, $R^{1a}$, $R^{1b}$, or $R^2$ comprises a solid support or is attached to a solid support. Alternatively, if the present compound comprises a carrier molecule or reactive group a solid support may be covalently attached independently to those substituents, allowing for further conjugation to a another dye, carrier molecule or solid support.

A solid support suitable for use in the present invention is typically substantially insoluble in liquid phases. Solid supports of the current invention are not limited to a specific type of support. Rather, a large number of supports are available and are known to one of ordinary skill in the art. Thus, useful solid supports include solid and semi-solid matrixes, such as aerogels and hydrogels, resins, beads, biochips (including thin film coated biochips), microfluidic chip, a silicon chip, multi-well plates (also referred to as microtitre plates or microplates), membranes, conducting and nonconducting metals, glass (including microscope slides) and magnetic supports. More specific examples of useful solid supports include silica gels, polymeric membranes, particles, derivatized plastic films, glass beads, cotton, plastic beads, alumina gels, polysaccharides such as Sepharose, poly(acrylate), polystyrene, poly(acrylamide), polyol, agarose, agar, cellulose, dextran, starch, FICOLL, heparin, glycogen, amylopectin, mannan, inulin, nitrocellulose, diazocellulose, polyvinylchloride, polypropylene, polyethylene (including poly (ethylene glycol)), nylon, latex bead, magnetic bead, paramagnetic bead, superparamagnetic bead, starch and the like.

In some embodiments, the solid support may include a solid support reactive functional group, including, but not limited to, hydroxyl, carboxyl, amino, thiol, aldehyde, halogen, nitro, cyano, amido, urea, carbonate, carbamate, isocyanate, sulfone, sulfonate, sulfonamide, sulfoxide, etc., for attaching the compounds of the invention. Useful reactive groups are disclosed above and are equally applicable to the solid support reactive functional groups herein.

A suitable solid phase support can be selected on the basis of desired end use and suitability for various synthetic protocols. For example, where amide bond formation is desirable to attach the compounds of the invention to the solid support, resins generally useful in peptide synthesis may be employed, such as polystyrene (e.g., PAM-resin obtained from Bachem Inc., Peninsula Laboratories, etc.), POLYHIPE™ resin (obtained from Aminotech, Canada), polyamide resin (obtained from Peninsula Laboratories), polystyrene resin grafted with polyethylene glycol (TentaGel™, Rapp Polymere, Tubingen, Germany), polydimethyl-acrylamide resin (available from Milligen/Biosearch, California), or PEGA beads (obtained from Polymer Laboratories).

Preparation of Conjugates

Conjugates of components (carrier molecules or solid supports), e.g., drugs, peptides, toxins, nucleotides, phospholipids and other organic molecules are prepared by organic synthesis methods using the reactive dyes, are generally prepared by means well recognized in the art (Haugland, MOLECULAR PROBES HANDBOOK, supra, 2002). Conjugation to form a covalent bond may consist of simply mixing the reactive dyes of the present invention in a suitable solvent in which both the reactive compound and the substance to be conjugated are soluble. The reaction preferably proceeds spontaneously without added reagents at room temperature or below. For those reactive dyes that are photoactivated, conjugation is facilitated by illumination of the reaction mixture to activate the reactive dye. Chemical modification of water-insoluble substances, so that a desired dye-conjugate may be prepared, is preferably performed in an aprotic solvent such as dimethylformamide (DMF), dimethylsulfoxide (DMSO), acetone, ethyl acetate, toluene, or chloroform.

Preparation of Peptide or Protein Conjugates Typically Comprises First Dissolving the Protein to be conjugated in aqueous buffer at about 1-10 mg/mL at room temperature or below. Bicarbonate buffers (pH about 8.3) are especially suitable for reaction with succinimidyl esters, phosphate buffers (pH about 7.2-8) for reaction with thiol-reactive functional groups and carbonate or borate buffers (pH about 9) for reaction with isothiocyanates and dichlorotriazines. The appropriate reactive dye is then dissolved in a nonhydroxylic solvent (usually DMSO or DMF) in an amount sufficient to give a suitable degree of conjugation when added to a solution of the protein to be conjugated. The appropriate amount of compound for any protein or other component is conveniently predetermined by experimentation in which variable amounts of the dye are added to the protein, the conjugate is chromatographically purified to separate unconjugated compound and the compound-protein conjugate is tested in its desired application.

Following addition of the reactive compound to the component solution, the mixture may be incubated for a suitable period (typically about 1 hour at room temperature to several hours on ice), the excess unreacted compound is removed by gel filtration, dialysis, HPLC, adsorption on an ion exchange or hydrophobic polymer or other suitable means. The conjugate is used in solution or lyophilized. In this way, suitable conjugates can be prepared from antibodies, antibody fragments, avidins, lectins, enzymes, proteins A and G, cellular proteins, albumins, histones, growth factors, hormones, and other proteins. The approximate degree of substitution is determined from the long wavelength absorption of the compound-protein conjugate by using the extinction coefficient of the un-reacted compound at its long wavelength absorption peak, the unmodified protein's absorption peak in the ultraviolet and by correcting the UV absorption of the conjugate for absorption by the compound in the UV.

Conjugates of polymers, including biopolymers and other higher molecular weight polymers are typically prepared by means well recognized in the art (for example, Brinkley et al., *Bioconjugate Chem.*, 3: 2 (1992)). In these embodiments, a single type of reactive site may be available, as is typical for polysaccharides or multiple types of reactive sites (e.g. amines, thiols, alcohols, phenols) may be available, as is typical for proteins. Selectivity of labeling is best obtained by selection of an appropriate reactive dye. For example, modification of thiols with a thiol-selective reagent such as a haloacetamide or maleimide, or modification of amines with an amine-reactive reagent such as an activated ester, acyl azide, isothiocyanate or 3,5-dichloro-2,4,6-triazine. Partial selectivity can also be obtained by careful control of the reaction conditions.

When modifying polymers with the compounds, an excess of the compound is typically used, relative to the expected degree of dye substitution. Any residual, un-reacted compound or hydrolysis product is typically removed by dialysis, chromatography or precipitation. Presence of residual, unconjugated compound can be detected by thin layer chromatography using a solvent that elutes the compound away from its conjugate. In all cases it is usually preferred that the reagents be kept as concentrated as practical so as to obtain adequate rates of conjugation.

In an exemplary embodiment, the conjugate is associated with an additional substance that binds either to the compound or the labeled component through noncovalent interaction. In another exemplary embodiment, the additional substance is an antibody, an enzyme, a hapten, a lectin, a receptor, an oligonucleotide, a nucleic acid, a liposome, or a polymer. The additional substance is optionally used to probe for the location of the conjugate, for example, as a means of enhancing the signal of the conjugate.

Method of Use

The present nucleic acid reporter molecules may be utilized without limit for the fluorescent detection of nucleic acid polymers in a test sample. The methods for the detection of single, double, triple or quadruple stranded DNA and RNA or a combination thereof comprises contacting a sample with a present nucleic acid reporter molecule to prepare a labeling mixture, incubating the sample with the staining solution for a sufficient amount of time for the present reporter molecules to complex with the nucleic acid, illuminating the sample with an appropriate wavelength and observing the illuminated labeling mixture whereby the nucleic acid polymer is detected.

The compound is typically combined with the sample as a staining solution. The staining solution is typically prepared by dissolving a present nucleic acid reporter molecule in an aqueous solvent such as water, a buffer solution or assay solution, such as phosphate buffered saline, or an organic solvent such as dimethylsulfoxide (DMSO), dimethylformamide (DMF), methanol, ethanol or acetonitrile. Typically, the present nucleic reporter molecules are first dissolved in an organic solvent such as DMSO as a stock solution. The stock solution is typically prepared about 300-100× more concentrated that the effective working concentration. Thus, the stock solution is diluted to an effective working concentration in an aqueous solution that optionally includes appropriate buffering components and a detergent. An effective working concentration of the present compounds is the amount sufficient to give a detectable optical response when complexed with nucleic acid polymers. Typically, the effective amount is about 100 nM to 100 µM. Most preferred is about 600 nM to 10 µM. For selected reporter compounds, staining is optimal when the staining solution has a concentration of about 2.0 µM (see Example 35). It is generally understood that the specific amount of the nucleic acid reporter molecules present in a staining solution is determined by the physical nature of the sample and the nature of the analysis being performed.

In an exemplary embodiment, the staining solution contains a detergent. This is particularly useful when the nucleic acid is present in an aqueous sample solution. Without wishing to be bound by a theory it appears that a low concentration of detergent stabilizes the present nucleic acid reporter molecule when present in solution. Thus the staining solution can be combined with an aqueous sample providing an optimized solution based detection assay. Detergents include, but are not limited to, CHAPS, Triton-X, SDS and Tween 20. The detergent is typically present in an aqueous solution at a concentration from about 0.01% to about 0.5% (w/v). More specifically the detergent is present from about 0.1% to about 0.3% (w/v). In an exemplary embodiment a staining solution comprises a present nucleic acid reporter molecule present at about 2.0 µM and a the detergent CHAPS present at about 0.2% (w/v)

The sample may be combined with the staining solution by any means that facilitates contact between the nucleic acid reporter molecules and the nucleic acid. The contact can occur through simple mixing, as in the case where the sample is a solution. The present reporter molecules may be added to the nucleic acid solution directly or may contact the solution on an inert matrix such as a blot or gel, a testing strip, a microarray, or any other solid or semi-solid surface, for example where only a simple and visible demonstration of the presence of nucleic acids is desired. Any inert matrix used to separate the sample can be used to detect the presence of nucleic acids by observing the fluorescent response on the inert matrix. Thus, in one embodiment is provided a composition comprising a sample and a present nucleic acid reporter molecule.

Alternatively, the sample may include cells and/or cell membranes. While selected examples of the compound disclosed herein may permeate cellular membranes rapidly and completely upon addition of the staining solution, any technique that is suitable for transporting the reporter molecules across cell membranes with minimal disruption of the viability of the cell and integrity of cell membranes is a valid method of combining the sample with the present reporter molecules for detection of intracellular nucleic acid.

Examples of suitable processes include action of chemical agents such as detergents, enzymes or adenosine triphosphate; receptor- or transport protein-mediated uptake; pore-forming proteins; microinjection; electroporation; hypoosmotic shock; or minimal physical disruption such as scrape loading or bombardment with solid particles coated with or in the presence of the present reporter molecules.

The sample is incubated in the presence of the nucleic acid reporter molecules for a time sufficient to form the fluorescent nucleic acid-reporter molecule complex. Detectable fluorescence in a solution of nucleic acids is essentially instantaneous. Detectable fluorescence within cell membranes requires the permeation of the dye into the cell. While most present nucleic acid reporter molecules are not cell permeant due to the presence of at least one negatively charged moiety, it is envisioned that the present compounds could be adequately substituted to provide cell permeant versions of the present compounds. In general, visibly detectable fluorescence can be obtained in a wide variety of cells with certain cell permeant embodiments of the present invention within about 10-30 minutes after combination with the sample, commonly within about 10-20 minutes. While permeation and fluorescence should be rapid for all reporter molecules comprising an aromatic substituent on the pyridinium or quinolinium moiety of the D moiety, it is readily apparent to one skilled in the art that the time necessary for sufficient permeation of the dye, or sufficient formation of the fluorescent nucleic acid complex, is dependent upon the physical and chemical nature of the individual sample and the sample medium.

In another embodiment, is provided a complex comprising a present nucleic acid reporter molecule and a nucleic acid polymer. To facilitate the detection of the nucleic acid-reporter molecule complex, the excitation or emission properties of the fluorescent complex are utilized. For example, the sample is excited by a light source capable of producing light at or near the wavelength of maximum absorption of the fluorescent complex, such as an ultraviolet or visible lamp, an arc lamp, a laser, or even sunlight. Preferably the fluorescent complex is excited at a wavelength equal to or greater than about 300 nm, more preferably equal to or greater than about 340 nm. The fluorescence of the complex is detected qualitatively or quantitatively by detection of the resultant light emission at a wavelength of greater than about 400 nm, more preferably greater than about 450 nm, most preferred greater than 480 nm. The emission is detected by means that include visible inspection, photographic film, or the use of current instrumentation such as fluorometers, quantum counters, plate readers, epifluorescence microscopes and flow cytometers or by means for amplifying the signal such as a photomultiplier.

In an exemplified embodiment, the present nucleic acid reporter compounds are used to detect DNA in the presence of RNA, wherein the method comprises the following steps:
a. combining a present nucleic acid reporter molecule with a sample to prepare a labeling mixture, wherein the nucleic acid reporter molecule has a DNA/RNA ratio of fluorescence enhancement greater than about one;
b. incubating the labeling mixture for a sufficient amount of time for the nucleic acid reporter molecule to associate with DNA in the sample to form an incubated mixture;
c. illuminating the incubated mixture with an appropriate wavelength to form an illuminated mixture; and,
d. observing the illuminated mixture whereby the DNA is detected in the presence of RNA.

Typically, the fluorescence of the DNA complex is distinguishable from the fluorescence of a RNA complex with the compound. This difference may be due to any detectable optical property, but in one embodiment, the fluorescence of the DNA complex is brighter than the fluorescence of a corresponding RNA complex with the compound. Therefore, in an exemplary embodiment, by comparing the fluorescence response of the DNA complex with a standard, the amount of DNA in the sample may be quantitated, even in the presence of RNA.

As discussed above, the DNA present in the sample may be present in a solution, or in or on a solid or semisolid support. In a preferred embodiment, the nucleic acid is present in a solution. The detection of DNA in solution may also be enhanced by the addition of a detergent to the staining solution. Exemplified detergents include, but are not limited to CHAPS, Triton-X, SDS and Tween 20. Particularly preferred is CHAPS, wherein the fluorescent single in an aqueous signal is stabilized for at least 6 hours.

The method may also be enhanced by the addition of an additional detection reagent that exhibits a greater fluorescence response when associated with RNA than when associated with DNA. A variety of nucleic acid stains that fluoresce brightly when complexed with RNA are known in the art.

The present nucleic acid reporter molecules that are capable of producing a fluorescent intensity signal that is greater on DNA than on RNA are determined empirically. The relative selectivity of the present compounds for differentiating DNA and RNA may be readily evaluated as set out in Examples 31-36.

The foregoing methods having been described it is understood that the many and varied compounds of the present invention can be utilized with the many methods. The compounds not being limited to just those that are specifically disclosed.

In an exemplary embodiment the present methods employ a nucleic acid reporter molecule that comprises the formula

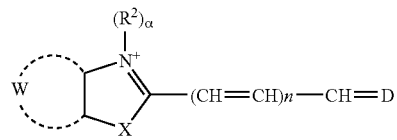

wherein the compound comprises at lest one negatively charged moiety at a physiological pH. Negatively charged moieties include, sulfo, carboxy, phosphate, phosphonate, an alkyl group substituted by sulfo, an alkyl group substituted by a carboxy, an alkyl group substituted by phosphate, or an alkyl group substituted by phosphonate.

These nucleic acid reporter molecules exhibit a fluorescence enhancement when non-covalently associated with a nucleic acid molecule. In one aspect, the fluorescence enhancement is greater when the nucleic acid is DNA than when the nucleic acid is RNA. In another aspect, the fluorescence enhancement is greater when the nucleic acid is RNA than when the nucleic acid is DNA.

W represents the atoms necessary to form one or two fused substituted 5- or 6-membered aromatic rings or one or two unsubstituted 5- or 6-membered aromatic rings. In an exemplary embodiment W comprises —C, —CR$^1$, or —N(R$^2$)$_\beta$; wherein β is 0 or 1, provided that α+β=1.

Each R$^1$ is independently hydrogen, a reactive group, a carrier molecule, a solid support, carboxy, sulfo, phosphate, phosphonate, amino, hydroxy, substituted aryl, unsubstituted aryl, substituted heteroaryl, unsubstituted heteroaryl, trifluoromethyl, halogen, substituted alkyl, unsubstituted alkyl, alkoxy, substituted alkylamino, unsubstituted alkylamino, substituted dialkylamino, or unsubstituted dialkylamino. In one aspect, includes a fused 6-membered aromatic ring.

R$^2$ is a substituted alkyl, unsubstituted alkyl, substituted arylalkyl, unsubstituted arylalkyl, substituted heteroalkyl, unsubstituted heteroalkyl, alkoxy, carboxy, carboxyalkyl, hydroxy, hydroxyalkyl, sulfo, sulfoalkyl, amino, aminoalkyl, alkylamino, dialkylamino, or trialkylammonium. X is O, S, or Se.

n is 0 or 1. In one aspect, n is 0.

D is a substituted pyridinium, unsubstituted pyridinium, substituted quinolinium, or unsubstituted quinolinium moiety. In one aspect, D has the formula

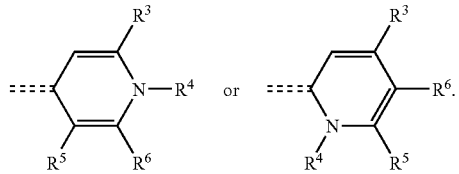

$R^3$, $R^4$, $R^5$ and $R^6$ are independently hydrogen, substituted alkyl, unsubstituted alkyl, substituted heteroalkyl, unsubstituted heteroalkyl, substituted aryl, unsubstituted aryl, substituted arylalkyl, unsubstituted arylalkyl, substituted heteroarylalkyl; unsubstituted heteroarylalkyl, substituted heteroaryl, unsubstituted heteroaryl, substituted cycloalkyl, unsubstituted cycloalkyl, substituted heterocycloalkyl, unsubstituted heterocycloalkyl, halogen, alkoxy, substituted alkylamino, unsubstituted alkylamino, substituted alkylthio, unsubstituted alkylthio, reactive group, solid support, or carrier molecule.

In one aspect, the D moiety forms a quinolinium moiety when $R^5$ and $R^6$, along with the atoms they are joined to, form a 6 membered aromatic ring. Alternatively, a member selected from $R^5$ in combination with $R^6$; $R^4$ in combination with $R^5$; $R^4$ in combination with $R^3$; $R^4$ in combination with $R^6$; and $R^3$ in combination with $R^6$; together with the atoms to which they are joined, form a ring which is a 5-, 6- or 7-membered heterocycloalkyl, a substituted 5-, 6- or 7-membered heterocycloalkyl, a 5-, 6- or 7-membered cycloalkyl, a substituted 5-, 6- or 7-membered cycloalkyl, a 5-, 6- or 7-membered heteroaryl, a substituted 5-, 6- or 7-membered heteroaryl, a 5-, 6- or 7-membered aryl or a substituted 5-6- or 7-membered aryl.

In one aspect at least one of $R^3$ and $R^4$ is alkyl, substituted alkyl, heteroalkyl, substituted heteroalkyl, alkoxy, alkylthio, aryl, substituted aryl, arylalkyl, substituted arylalkyl, heteroaryl, substituted heteroaryl, heteroarylalkyl or substituted heteroarylalkyl. In another aspect, $R^3$ and $R^4$ are independently alkyl, substituted alkyl, phenyl, substituted phenyl, benzyl, substituted benzyl, alkylthio, substituted alkylthio, indolyl, imidazolyl, or thiazolyl. In yet another aspect, $R^3$ is hydrogen, alkyl, substituted alkyl, —$(CH_2)_a$-aryl or —$(CH_2)_a$-heteroaryl; and, $R^4$ is hydrogen, alkyl, substituted alkyl, —$(CH_2)_a$-aryl or —$(CH_2)_a$-heteroaryl; wherein a is an integer from 0 to about 6.

In an exemplary embodiment, the nucleic aid reporter molecule of the present methods have the formula:

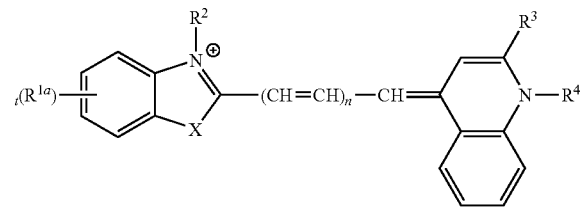

or the formula

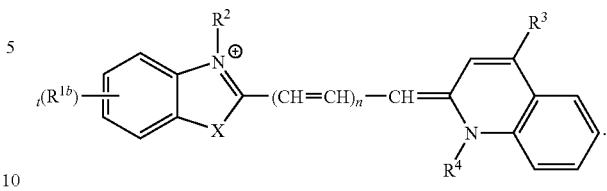

In this instance each $R^{1a}$ and $R^{1b}$ are independently hydrogen, carboxy, sulfo, phosphate, phosphonate, amino, hydroxyl, trifluoromethyl, halogen, alkyl, substituted alkyl, alkoxy, alkylamino, substituted alkylamino, dialkylamino, substituted dialkylamino, fused benzene, substituted fused benzene, trifluomethyl, halogen, reactive group, solid support or carrier molecule. t is an integer from 0 to about 4.

In one aspect $R^4$ is hydrogen, alkyl, —$(CH_2)_a$-aryl, or —$(CH_2)_a$-heteroaryl, wherein a is an integer from 0 to about 6. In a further aspect $R^4$ is an alkyl, phenyl, benzyl, alkylthio, indolyl, imidazolyl, or thiazolyl. Typically at least one of $R^1$ and $R^2$ comprises a negatively charged substituent. An exemplified nucleic acid reporter molecule is Compound 25.

In an exemplary embodiment, the nucleic aid reporter molecule of the present methods comprise a reactive group, solid support and carrier molecule wherein these substituents independently comprise a linker that is a single covalent bond, or a covalent linkage that is linear or branched, cyclic or heterocyclic, saturated or unsaturated, having 1-20 nonhydrogen atoms selected from the group consisting of C, N, P, O and S; and are composed of any combination of ether, thioether, amine, ester, carboxamide, sulfonamide, hydrazide bonds and aromatic or heteroaromatic bonds.

In an exemplary embodiment, the reactive group is an acrylamide, an activated ester of a carboxylic acid, a carboxylic ester, an acyl azide, an acyl nitrile, an aldehyde, an alkyl halide, an anhydride, an aniline, an amine, an aryl halide, an azide, an aziridine, a boronate, a diazoalkane, a haloacetamide, a haloalkyl, a halotriazine, a hydrazine, an imido ester, an isocyanate, an isothiocyanate, a maleimide, a phosphoramidite, a reactive platinum complex, a silyl halide, a sulfonyl halide, a thiol or a photoactivatable group. In a further aspect, the reactive group is carboxylic acid, succinimidyl ester of a carboxylic acid, hydrazide, amine or a maleimide.

In an exemplary embodiment the carrier molecule is an amino acid, a peptide, a protein, a polysaccharide, a nucleoside, a nucleotide, an oligonucleotide, a nucleic acid polymer, a hapten, a psoralen, a drug, a hormone, a lipid, a lipid assembly, a synthetic polymer, a polymeric microparticle, a biological cell or a virus. In a further aspect, the carrier molecule is an antibody or fragment thereof, an avidin or streptavidin, a biotin, a blood component protein, a dextran, an enzyme, an enzyme inhibitor, a hormone, an IgG binding protein, a fluorescent protein, a growth factor, a lectin, a lipopolysaccharide, a microorganism, a metal binding protein, a metal chelating moiety, a non-biological microparticle, a peptide toxin, a phosphotidylserine-binding protein, a structural protein, a small-molecule drug, or a tyramide.

In an exemplary embodiment, the solid support is a microfluidic chip, a silicon chip, a microscope slide, a microplate well, silica gels, polymeric membranes, particles, derivatized plastic films, glass beads, cotton, plastic beads, alumina gels, polysaccharides, polyvinylchloride, polypropylene, polyethylene, nylon, latex bead, magnetic bead, paramagnetic bead, or superparamagnetic bead. In a further aspect, the solid support is Sepharose, poly(acrylate), polystyrene, poly(acrylamide), polyol, agarose, agar, cellulose, dextran, starch, FICOLL, heparin, glycogen, amylopectin, mannan, inulin, nitrocellulose, diazocellulose or starch.

Sample Preparation

The sample may be prepared using methods well known in the art for isolating nucleic acid for in vitro and solution based assay detection or well known methods for live cell or fixed cells for intracellular and/or in vivo detection of nucleic acids. The sample includes, without limitation, any biological derived material that is thought to contain a nucleic acid polymer. Alternatively, samples also include material that nucleic acid polymers have been added to such as a PCR reaction mixture, a polymer gel such as agarose or polyacrylamide gels or a microfluidic assay system. In another aspect of the present disclosure, the sample can also include a buffer solution that contains nucleic acid polymers to determine the present reporter molecules that are ideal under different assay conditions or to determine the present reporter molecules that are preferential DNA reporters or RNA reporters.

The sample can be a biological fluid such as whole blood, plasma, serum, nasal secretions, sputum, saliva, urine, sweat, transdermal exudates, cerebrospinal fluid, or the like. Biological fluids also include tissue and cell culture medium wherein an analyte of interest has been secreted into the medium. Alternatively, the sample may be whole organs, tissue or cells from the animal. Examples of sources of such samples include muscle, eye, skin, gonads, lymph nodes, heart, brain, lung, liver, kidney, spleen, thymus, pancreas, solid tumors, macrophages, mammary glands, mesothelium, and the like. Cells include without limitation prokaryotic cells such as bacteria, yeast, fungi, mycobacteria and mycoplasma, and eukaryotic cells such as nucleated plant and animal cells that include primary cultures and immortalized cell lines. Typically prokaryotic cells include *E. coli* and *S. aureus*. Eukaryotic cells include without limitation ovary cells, epithelial cells, circulating immune cells, β cells, hepatocytes, and neurons.

In an exemplary embodiment, the sample comprises biological fluids, buffer solutions, live cells, fixed cells, eukaryotic cells, prokaryotic cells, nucleic acid polymers, nucleosides, nucleotides, a polymeric gel or tissue sections. In a further aspect, the sample comprises nucleic acid polymers in an aqueous buffer.

The nucleic acid may be either natural (biological in origin) or synthetic (prepared artificially). The nucleic acid may be present as nucleic acid fragments, oligonucleotides, or nucleic acid polymers. The nucleic acid may be present in a condensed phase, such as a chromosome. The presence of the nucleic acid in the sample may be due to a successful or unsuccessful experimental methodology, undesirable contamination, or a disease state. Nucleic acid may be present in all, or only part, of a sample, and the presence of nucleic acids may be used to distinguish between individual samples, or to differentiate a portion or region within a single sample.

The nucleic acid may be enclosed in a biological structure, for example contained within a viral particle, an organelle, or within a cell. The nucleic acids enclosed in biological structures may be obtained from a wide variety of environments, including cultured cells, organisms or tissues, unfiltered or separated biological fluids such as urine, cerebrospinal fluid, blood, lymph fluids, tissue homogenate, mucous, saliva, stool, or physiological secretions or environmental samples such as soil, water and air. The nucleic acid may be endogenous or introduced as foreign material, such as by infection or by transfection. The present nucleic acid reporter molecules can also be used for staining nucleic acids in a cell or cells that is fixed and treated with routine histochemical or cytochemical procedures.

Alternatively, the nucleic acid is not enclosed within a biological structure, but is present as a sample solution. The sample solution can vary from one of purified nucleic acids to crude mixtures such as cell extracts, biological fluids and environmental samples. In some cases it is desirable to separate the nucleic acids from a mixture of biomolecules or fluids in the solution prior to combination with the present reporter molecules. Numerous, well known, techniques exist for separation and purification of nucleic acids from generally crude mixtures with other proteins or other biological molecules. These include such means as electrophoretic techniques and chromatographic techniques using a variety of supports.

The sample may be incubated in the presence of the nucleic acid reporter molecules for a time sufficient to form a nucleic acid-reporter molecule complex. While permeation and complexation may be more or less rapid for the compounds disclosed herein, largely depending on the nature of the substituents present on the compound. It should be apparent to one skilled in the art that the time necessary for sufficient permeation of the dye, or sufficient formation of the resulting nucleic acid complex, is dependent upon the physical and chemical nature of the individual sample and the sample medium (see for example U.S. Pat. No. 5,658,751).

Illumination

The sample containing a nucleic acid-reporter molecule complex may be illuminated with a wavelength of light selected to give a detectable optical response, and observed with a means for detecting the optical response. By optical response is meant any detectable calorimetric or luminescent property of the complex. Typically, the optical response is related to the excitation or emission properties of the complex.

For example, the sample may be excited by a light source capable of producing light at or near the wavelength of maximum absorption of the fluorescent complex, such as an ultraviolet or visible lamp, an arc lamp, a laser, or even sunlight. The optical response is optionally detected by visual inspection, or by use of any of the following devices: CCD camera, video camera, photographic film, laser-scanning devices, fluorometers, photodiodes, quantum counters, epifluorescence microscopes, scanning microscopes, flow cytometers, fluorescence microplate readers, or by means for amplifying the signal such as photomultiplier tubes. Where the sample is examined using a flow cytometer, examination of the sample optionally includes sorting portions of the sample according to their fluorescence response.

The wavelengths of the excitation and emission bands of the nucleic acid reporter molecules vary with reporter molecule composition to encompass a wide range of illumination and detection bands. This allows the selection of individual reporter molecules for use with a specific excitation source or detection filter. In particular, present reporter molecules can be selected that possess excellent correspondence of their excitation band with the 488 nm band of the commonly used argon laser or emission bands which are coincident with preexisting filters.

The presence, location, and distribution of nucleic acid, particularly DNA, may be detected using the spectral properties of the compound-nucleic acid complex. Once the dye-nucleic acid complex is formed, its presence may be detected and used as an indicator of the presence, location, or type of nucleic acids in the sample, or as a basis for sorting cells, or as a key to characterizing the sample or cells in the sample. Such characterization may be enhanced by the use of additional reagents, including fluorescent reagents. The nucleic acid concentration in a sample can also be quantified by comparison with known relationships between the fluorescence of the nucleic acid-dye complex and concentration of nucleic acids in the sample. In particular, fluorescence intensity may be compared to a standard curve prepared from samples containing known nucleic acid concentrations, particularly DNA concentrations.

Kits

Suitable kits for forming a nucleic acid-reporter molecule complex and detecting the nucleic acid also form part of the present disclosure. Such kits can be prepared from readily available materials and reagents and can come in a variety of embodiments. The contents of the kit will depend on the design of the assay protocol or reagent for detection or measurement. All kits will contain instructions, appropriate reagents, and one or more of the presently disclosed nucleic acid reporter molecules. Typically, instructions include a tangible expression describing the reagent concentration or at least one assay method parameter such as the relative amounts of reagent and sample to be added together, maintenance time periods for reagent/sample admixtures, temperature, buffer conditions and the like to allow the user to carry out any one of the methods or preparations described above. In one aspect, the kit is formulated to facilitate the high-throughput screening of multiple samples, such as may be accomplished using automated methods.

Thus, a kit for detecting nucleic acid in a sample may comprise a compound as described above. The kit may further include instructions for performing one or more of the above disclosed methods, including the detection and/or quantitation of DNA in the presence of RNA.

The kit may optionally further include one or more of the following; sample preparation reagents, a buffering agent, nucleic acid standards, an aqueous nucleic acid reporter molecule dilution buffer, an organic solvent or an additional detection reagent, particularly where the additional detection reagent is an additional distinct nucleic acid reporter molecule. Where the additional nucleic acid reporter is a RNA-selective nucleic acid stain, the kit may be useful for detecting and/or quantitating DNA in the presence of RNA.

In an exemplified embodiment, the dilution buffer (for the nucleic acid reporter molecule) contains a detergent in a final concentration of about 0.01% to about 0.5% (w/v). The detergents are as disclosed about and include CHAPS, Triton-X, SDS and Tween 20.

In an exemplified embodiment, a present kit comprises a compound according to Formula IX or Formula X, a dilution buffer solution, DNA standards and instructions for detecting and/or quantitating DNA in the presence of RNA. In one aspect the nucleic acid compound is present as a concentrated stock solution, such as 200×.

The foregoing kits having been described it is understood that the many and varied compounds of the present invention can be utilized with the many kits. The compounds not being limited to just those that are specifically disclosed.

In an exemplary embodiment the present kits comprise a nucleic acid reporter molecule that comprises the formula

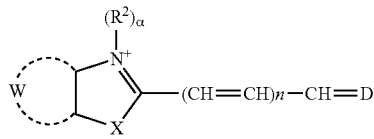

wherein the compound comprises at lest one negatively charged moiety at a physiological pH. Negatively charged moieties include, sulfo, carboxy, phosphate, phosphonate, an alkyl group substituted by sulfo, an alkyl group substituted by a carboxy, an alkyl group substituted by phosphate, or an alkyl group substituted by phosphonate.

These nucleic acid reporter molecules exhibit a fluorescence enhancement when non-covalently associated with a nucleic acid molecule. In one aspect, the fluorescence enhancement is greater when the nucleic acid is DNA than when the nucleic acid is RNA. In another aspect, the fluorescence enhancement is greater when the nucleic acid is RNA than when the nucleic acid is DNA.

W represents the atoms necessary to form one or two fused substituted 5- or 6-membered aromatic rings or one or two unsubstituted 5- or 6-membered aromatic rings. In an exemplary embodiment W comprises —C, —CR$^1$, or —N(R$^2$)$_\beta$; wherein $\beta$ is 0 or 1, provided that $\alpha+\beta=1$.

Each R$^1$ is independently hydrogen, a reactive group, a carrier molecule, a solid support, carboxy, sulfo, phosphate, phosphonate, amino, hydroxy, substituted aryl, unsubstituted aryl, substituted heteroaryl, unsubstituted heteroaryl, trifluoromethyl, halogen, substituted alkyl, unsubstituted alkyl, alkoxy, substituted alkylamino, unsubstituted alkylamino, substituted dialkylamino, or unsubstituted dialkylamino. In one aspect, includes a fused 6-membered aromatic ring.

R$^2$ is a substituted alkyl, unsubstituted alkyl, substituted arylalkyl, unsubstituted arylalkyl, substituted heteroalkyl, unsubstituted heteroalkyl, alkoxy, carboxy, carboxyalkyl, hydroxy, hydroxyalkyl, sulfo, sulfoalkyl, amino, aminoalkyl, alkylamino, dialkylamino, or trialkylammonium. X is O, S, or Se.

n is 0 or 1. In one aspect, n is 0.

D is a substituted pyridinium, unsubstituted pyridinium, substituted quinolinium, or unsubstituted quinolinium moiety. In one aspect, D has the formula

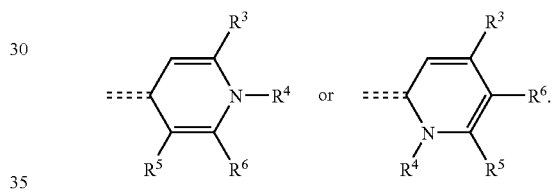

R$^3$, R$^4$, R$^5$ and R$^6$ are independently hydrogen, substituted alkyl, unsubstituted alkyl, substituted heteroalkyl, unsubstituted heteroalkyl, substituted aryl, unsubstituted aryl, substituted arylalkyl, unsubstituted arylalkyl, substituted heteroarylalkyl; unsubstituted heteroarylalkyl, substituted heteroaryl, unsubstituted heteroaryl, substituted cycloalkyl, unsubstituted cycloalkyl, substituted heterocycloalkyl, unsubstituted heterocycloalkyl, halogen, alkoxy, substituted alkylamino, unsubstituted alkylamino, substituted alkylthio, unsubstituted alkylthio, reactive group, solid support, or carrier molecule.

In one aspect, the D moiety forms a quinolinium moiety when R$^5$ and R$^6$, along with the atoms they are joined to, form a 6 membered aromatic ring. Alternatively, a member selected from R$^5$ in combination with R$^6$; R$^4$ in combination with R$^5$; R$^4$ in combination with R$^3$; R$^4$ in combination with R$^6$; and R$^3$ in combination with R$^6$; together with the atoms to which they are joined, form a ring which is a 5-, 6- or 7-membered heterocycloalkyl, a substituted 5-, 6- or 7-membered heterocycloalkyl, a 5-, 6- or 7-membered cycloalkyl, a substituted 5-, 6- or 7-membered cycloalkyl, a 5-, 6- or 7-membered heteroaryl, a substituted 5-, 6- or 7-membered heteroaryl, a 5-, 6- or 7-membered aryl or a substituted 5-, 6- or 7-membered aryl.

In one aspect at least one of R$^3$ and R$^4$ is alkyl, substituted alkyl, heteroalkyl, substituted heteroalkyl, alkoxy, alkylthio, aryl, substituted aryl, arylalkyl, substituted arylalkyl, heteroaryl, substituted heteroaryl, heteroarylalkyl or substituted heteroarylalkyl. In another aspect, R$^3$ and R$^4$ are independently alkyl, substituted alkyl, phenyl, substituted phenyl, benzyl, substituted benzyl, alkylthio, substituted alkylthio, indolyl, imidazolyl, or thiazolyl. In yet another aspect, $R^3$ is hydrogen, alkyl, substituted alkyl, —$(CH_2)_a$-aryl or —$(CH_2)_a$-heteroaryl; and, $R^4$ is hydrogen, alkyl, substituted alkyl, —$(CH_2)_a$-aryl or —$(CH_2)_a$-heteroaryl; wherein a is an integer from 0 to about 6.

In an exemplary embodiment, the nucleic aid reporter molecule of the present kits have the formula:

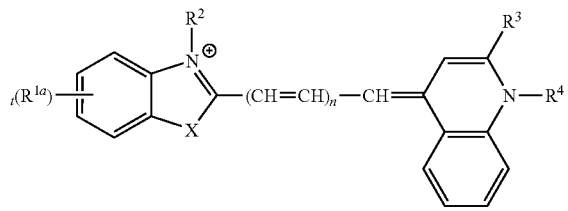

or the formula

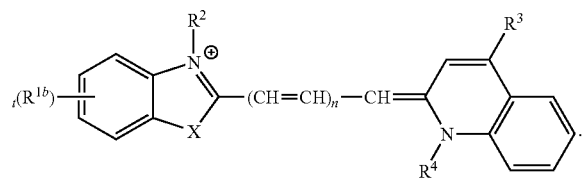

In this instance, each $R^{1a}$ and $R^{1b}$ are independently hydrogen, carboxy, sulfo, phosphate, phosphonate, amino, hydroxyl, trifluoromethyl, halogen, alkyl, substituted alkyl, alkoxy, alkylamino, substituted alkylamino, dialkylamino, substituted dialkylamino, fused benzene, substituted fused benzene, trifluomethyl, halogen, reactive group, solid support or carrier molecule. t is an integer from 0 to about 4.

In one aspect $R^4$ is hydrogen, alkyl, —$(CH_2)_a$-aryl, or —$(CH_2)_a$-heteroaryl, wherein a is an integer from 0 to about 6. In a further aspect $R^4$ is an alkyl, phenyl, benzyl, alkylthio, indolyl, imidazolyl, or thiazolyl. Typically at least one of $R^1$ and $R^2$ comprises a negatively charged substituent. An exemplified nucleic acid reporter molecule is Compound 25.

In an exemplary embodiment, the nucleic aid reporter molecule of the present kits comprise a reactive group, solid support and carrier molecule wherein these substituents independently comprise a linker that is a single covalent bond, or a covalent linkage that is linear or branched, cyclic or heterocyclic, saturated or unsaturated, having 1-20 nonhydrogen atoms selected from the group consisting of C, N, P, O and S; and are composed of any combination of ether, thioether, amine, ester, carboxamide, sulfonamide, hydrazide bonds and aromatic or heteroaromatic bonds.

In an exemplary embodiment, the reactive group is selected from the group consisting of an acrylamide, an activated ester of a carboxylic acid, a carboxylic ester, an acyl azide, an acyl nitrile, an aldehyde, an alkyl halide, an anhydride, an aniline, an amine, an aryl halide, an azide, an aziridine, a boronate, a diazoalkane, a haloacetamide, a haloalkyl, a halotriazine, a hydrazine, an imido ester, an isocyanate, an isothiocyanate, a maleimide, a phosphoramidite, a reactive platinum complex, a silyl halide, a sulfonyl halide, a thiol and a photoactivatable group. In a further aspect, the reactive group is selected from the group consisting of carboxylic acid, succinimidyl ester of a carboxylic acid, hydrazide, amine and a maleimide.

In an exemplary embodiment the carrier molecule is selected from the group consisting of an amino acid, a peptide, a protein, a polysaccharide, a nucleoside, a nucleotide, an oligonucleotide, a nucleic acid polymer, a hapten, a psoralen, a drug, a hormone, a lipid, a lipid assembly, a synthetic polymer, a polymeric microparticle, a biological cell or a virus. In a further aspect, the carrier molecule is selected from the group consisting of an antibody or fragment thereof, an avidin or streptavidin, a biotin, a blood component protein, a dextran, an enzyme, an enzyme inhibitor, a hormone, an IgG binding protein, a fluorescent protein, a growth factor, a lectin, a lipopolysaccharide, a microorganism, a metal binding protein, a metal chelating moiety, a non-biological microparticle, a peptide toxin, a phosphotidylserine-binding protein, a structural protein, a small-molecule drug, or a tyramide.

In an exemplary embodiment, the solid support is selected from the group consisting of a microfluidic chip, a silicon chip, a microscope slide, a microplate well, silica gels, polymeric membranes, particles, derivatized plastic films, glass beads, cotton, plastic beads, alumina gels, polysaccharides, polyvinylchloride, polypropylene, polyethylene, nylon, latex bead, magnetic bead, paramagnetic bead, and superparamagnetic bead. In a further aspect, the solid support is selected from the group consisting of Sepharose, poly(acrylate), polystyrene, poly(acrylamide), polyol, agarose, agar, cellulose, dextran, starch, FICOLL, heparin, glycogen, amylopectin, mannan, inulin, nitrocellulose, diazocellulose and starch.

A detailed description of the invention having been provided above, the following examples are given for the purpose of illustrating the invention and shall not be construed as being a limitation on the scope of the invention or claims.

EXAMPLES

Example 1

Preparation of Compound 1

A mixture of 12.4 g of 3-(2-benzothiazolylthio)-1-propanesulfonic acid, sodium salt and 14.6 g of propanesultone is heated in 40 mL of DMF at reflux for 6 hours. The crude mixture is added slowly to 40 mL of ethyl acetate and stirred for three days. The solid product is filtered, redissolved in 100 mL of water, and lyophilized to obtain Compound 1.

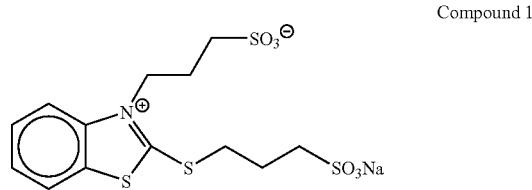

Compound 1

Example 2

Preparation of Compound 2

To 0.235 g of 4-methyl-1-phenyl-quinolin-2-one in 10 mL of THF at −78° C. under nitrogen, 1 mL of 2.5 M n-Butyl-lithium is introduced. After stirring for 30 minutes, 0.5 mL of acetic acid is added and the resulting mixture is further stirred at room temperature. All volatile components are then removed under reduced pressure to yield the crude 2-butyl-4-methyl-1-phenylquinolinium intermediate. This intermediate is then dissolved in 5 mL of methanol and added to a slurry of 0.82 g of Compound 1 in 15 mL of methanol, with the subsequent addition of 0.56 mL of triethylamine. The resulting mixture immediately turns red. After several hours of stirring at room temperature, the solvent is evaporated and the crude product is purified using silica gel column chromatography.

The following compounds (3-19) are prepared using methods analogous to those used above to prepare Compound 2. For example, excess 3-(3-sulfoproypyl)-2-(3-sulfopropylthio)-benzthiazolium, inner salt may be reacted with the corresponding appropriate quinolinium moiety in the presence of a base (e.g. triethylamine) to generate Compounds 3-19.

Compound 2

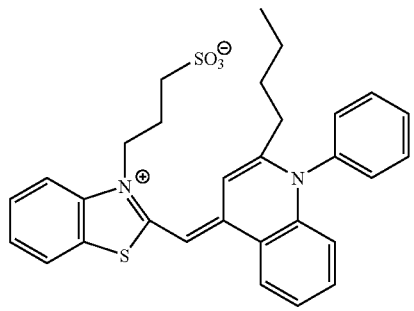

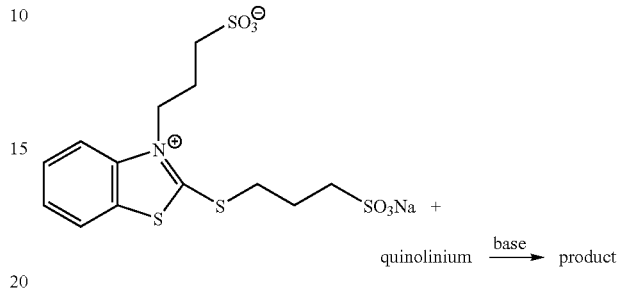

TABLE 3

| Compound | Ex/Em (nm)[1] | Fluorescence Enhancement Ratio (DNA/RNA)[2] |
|---|---|---|
| Compound 2 | 500/520 | 6.8 |
| Compound 3 | 507/550 | 6.1 |
| Compound 4 | 505/530 | 4.5 |

TABLE 3-continued
| Compound | Ex/Em (nm)[1] | Fluorescence Enhancement Ratio (DNA/RNA)[2] |
|---|---|---|
| 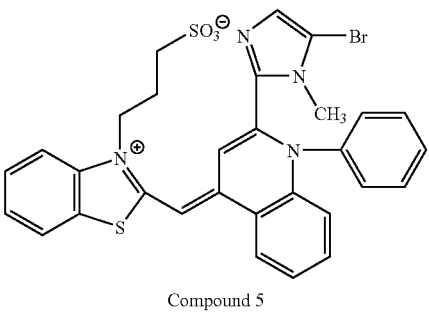 Compound 5 | 524/555 | 17 |
| 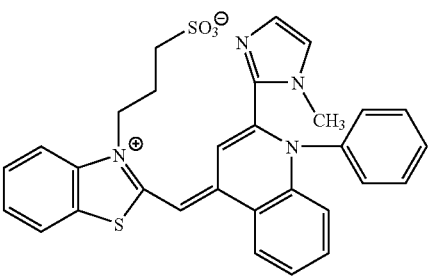 Compound 6 | 521/555 | 17 |
| 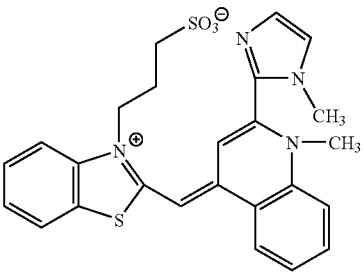 Compound 7 | 520/556 | 18.5 |
| 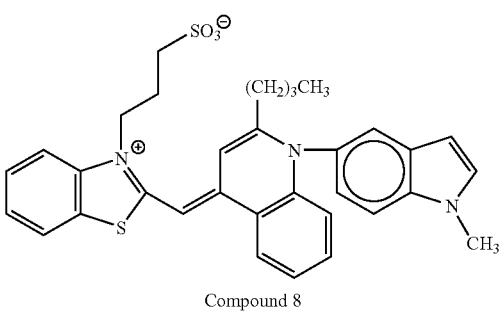 Compound 8 | 500/525 | 3.8 |

TABLE 3-continued
| Compound | Ex/Em (nm)[1] | Fluorescence Enhancement Ratio (DNA/RNA)[2] |
|---|---|---|
| 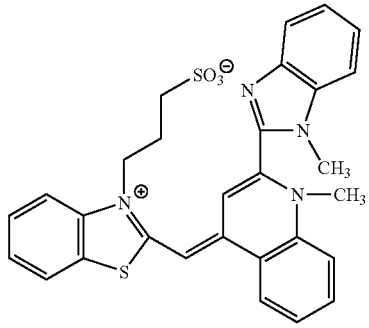Compound 9 | 522/570 | 5.9 |
| 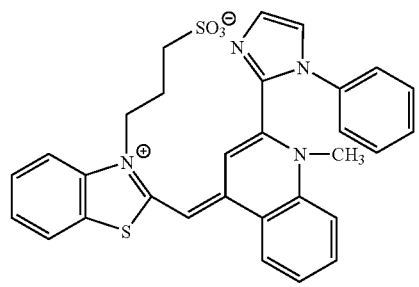Compound 10 | 527/560 | 4.3 |
| 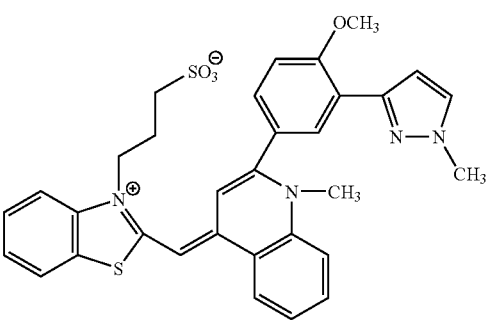Compound 11 | 507/545 | 3.2 |
| 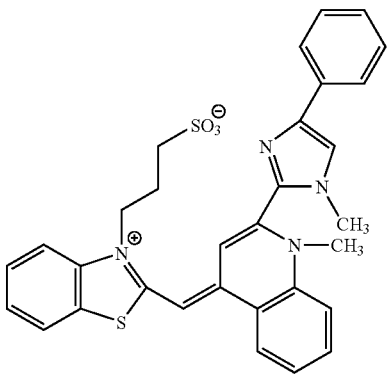Compound 12 | 523/566 | 3.6 |

TABLE 3-continued
| Compound | Ex/Em (nm)[1] | Fluorescence Enhancement Ratio (DNA/RNA)[2] |
|---|---|---|
| 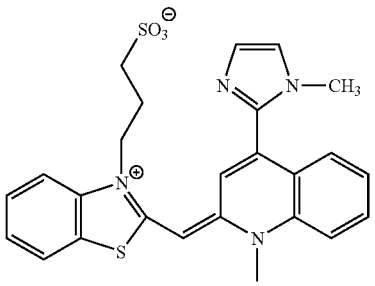\nCompound 13 | 520/556 | 5.8 |
| 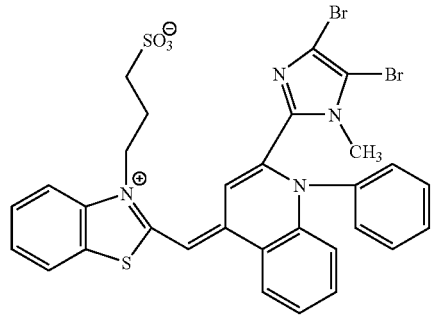\nCompound 14 | 525/565 | 12.6 |
| 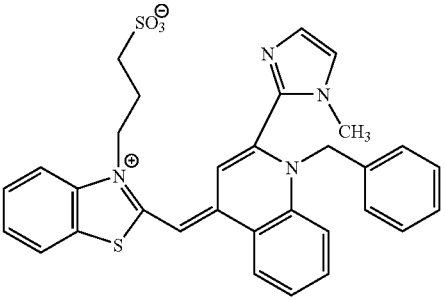\nCompound 15 | 524/557 | 38 |
| 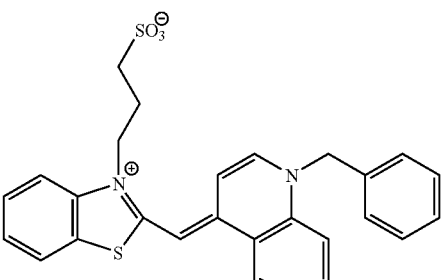\nCompound 16 | 505/531 | 6.2 |

TABLE 3-continued

| Compound | Ex/Em (nm)[1] | Fluorescence Enhancement Ratio (DNA/RNA)[2] |
|---|---|---|
| 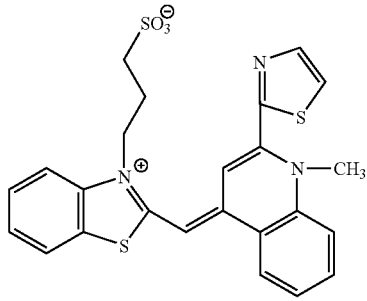 Compound 17 | 524/603 | 2.6 |
| 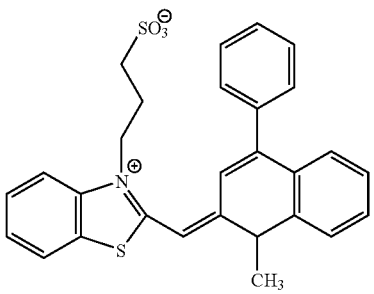 Compound 18 | 505/551 | 7.9 |
| 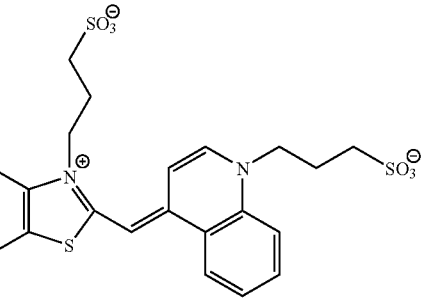 Compound 19 | 504/531 | 1.3 |

[1] Complex with nucleic acid
[2] The ratio of the fluorescence enhancement of the compound when associated with DNA to the fluorescence enhancement of the compound when associated with RNA

Example 3

Preparation of Compound 20

To 50 mL of chlorosulfonic acid at room temperature is added 10 g of 2-methylthio-benzothiazole in small portions. After the addition is complete, the reaction mixture is heated at 35° C. for several hours. The reaction mixture is then cooled to room temperature and added dropwise to 750 mL of an ice/water slurry with vigorous stirring. The resulting white solid product is collected by filtration, stirred in 200 mL of water for 30 minutes, and filtered again to recover 14.5 g of Compound 20.

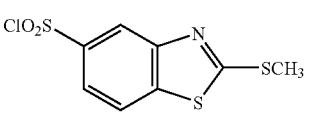

Compound 20

Example 4

Preparation of Compound 21

To about 8 g of the sulfonyl chloride Compound 20 in 80 mL of water is added 10 mL of a 10% NaOH solution. The resulting mixture is stirred at room temperature overnight. The resulting solid is filtered, stirred in 100 mL of methanol for 4 hours and 2.5 g of Compound 21 is recovered.

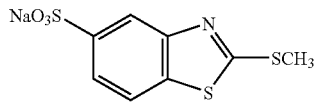

Compound 21

Example 5

Preparation of Compound 22

A mixture of 0.6 g of Compound 21 and 1.9 g of methyl toluenesulfonate is heated in 4 mL of DMF at 120° C. for 1 hour. Ethyl acetate (20 mL) is then added, and the resulting mixture heated at reflux for an additional 5 minutes. The product (1.67 g) Compound 22 is recovered by filtration as a white solid.

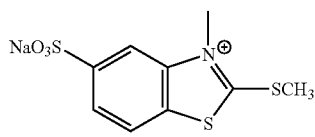

Compound 22

Example 6

Preparation of Compound 23

To a mixture of 0.92 mmole of Compound 22 and 1 mmole of 1,4-dimethyl-2-(2-(1-methylimidazolyl)-quinolinium acetate in 5 mL of methanol is added 0.6 mL of triethylamine. The reaction mixture is stirred for an hour, and the resulting dark red solid is collected by filtration. The product thus obtained is washed with methanol and dried to give Compound 23.

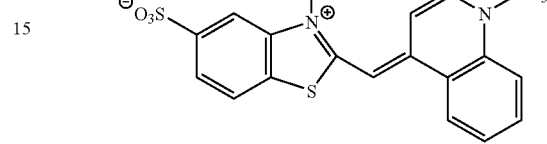

Compound 23

The following compounds (24-28) may be prepared in a method analogous to that of Compound 23, above. For example, excess Compound 22 may be reacted with the appropriate quinolinum/pyridinium moiety in the presence of a base (e.g. triethylamine) to generate the desired product.

Table 4 below shows the differential fluorescence enhancement of selected compounds when associated with DNA, when compared to their fluorescent enhancement when associated with RNA.

TABLE 4

| Compound | Ex/Em (nm)[1] | Fluorescence Enhancement Ratio (DNA/RNA)[2] |
|---|---|---|
| 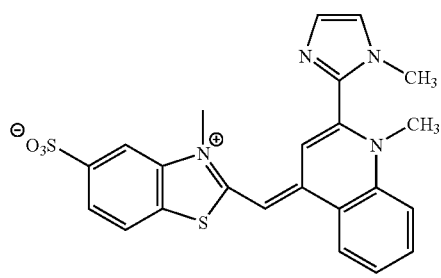<br>Compound 23 | 519/552 | 9 |
| 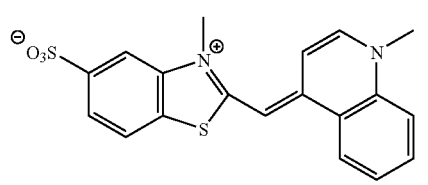<br>Compound 24 | 498/522 | 6.6 |

TABLE 4-continued

| Compound | Ex/Em (nm)[1] | Fluorescence Enhancement Ratio (DNA/RNA)[2] |
|---|---|---|
| Compound 25 | 504/522 | 26 |
| Compound 26 | 522/554 | 47 |
| Compound 27 | 447/483 | 4.1 |
| Compound 28 | 501/NA | NA |
| Compound 29[3] | 504/522 | 1 |
| Compound 30[3] | 447/483 | 1 |

[1]Complex with nucleic acid
[2]The ratio of the fluorescence enhancement of the compound when associated with DNA to the fluorescence enhancement of the compound when associated with RNA
[3]Included for comparison purposes

Example 7

Preparation of Compound 31

To a mixture of 0.28 g of 4-methyl-1-(4-sulfobutyl)-quinolinium, inner salt and 0.367 g of 3-methyl-2-methylthio-benzothiazolium tosylate in 15 mL of dichloromethane is added 0.16 mL of triethylamine. The reaction mixture is stirred at room temperature overnight. The crude product is recovered by filtration and stirred in 20 mL of 1:1 (v/v) mixture of DMF and acetonitrile for 30 minutes to obtain Compound 31.

Compound 31

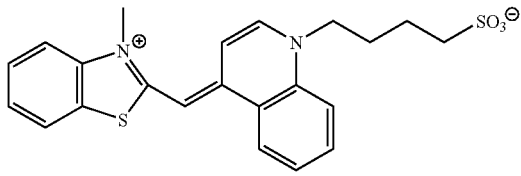

Example 8

Preparation of Compound 32

A mixture of 55 mg of 3-(3-sulfopropyl)-2-methylbenzothiazolium, inner salt and 78 mg of 4-chloro-1-methylquinolinium tosylate and 0.07 mL of triethylamine is stirred in 10 mL of dichloromethane at room temperature overnight. The resulting product is recovered from filtration to give Compound 32.

Compound 32

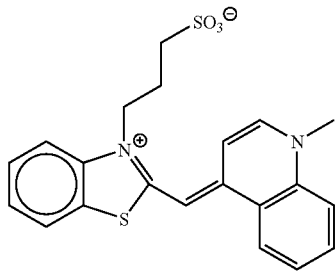

Example 9

Preparation of Compound 33

To a mixture of 0.1 g of Compound 41 and 1-benzyl-4-chloroquinolinium bromide in 10 mL of dichloroethane is added 0.22 mL of triethylamine and the reaction mixture is stirred for several hours. The reaction mixture is then diluted with chloroform and washed with brine, and the crude product thus obtained is purified using silica gel column chromatography to yield pure Compound 33.

Compound 33

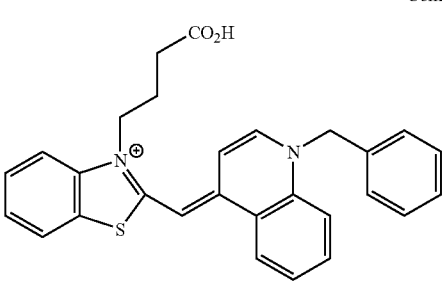

Example 10

Preparation of Compound 34

To a suspension of 0.5 g of the sulfonyl chloride Compound 20 in 10 mL of water, 0.47 g of 6-aminohexanoic acid and 2.5 mL of 10% NaOH are introduced and the mixture is stirred at room temperature overnight. The solvent is removed by evaporation, and the crude product is purified using silica gel column chromatography to give compound 34.

Compound 34

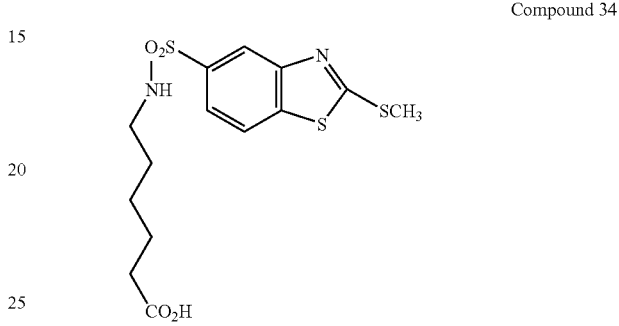

Example 11

Preparation of Compound 35

A mixture of 0.381 g of the carboxylic acid derivative Compound 34 and 0.23 g of methyl toluenesulfonate is heated at 120° C. for 1.5 hours. Ethyl acetate (about 30 mL) is added and the mixture briefly heated at reflux. The resulting product is obtained via filtration to give Compound 35.

Compound 35

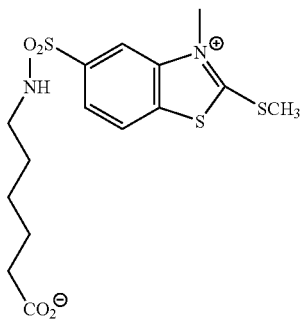

Example 12

Preparation of Compound 36

0.1 mL of triethylamine is added to a mixture of 0.13 g of Compound 35 and 80 mg of 1-benzyl-4-methylquinolinium bromide in a mixed solvent system of 10 mL dichloroethane and 3 mL of DMF. The resulting mixture is stirred at room temperature overnight. The resulting product is filtered and further purified by stirring in 2 mL of methanol for 30 minutes to give Compound 36.

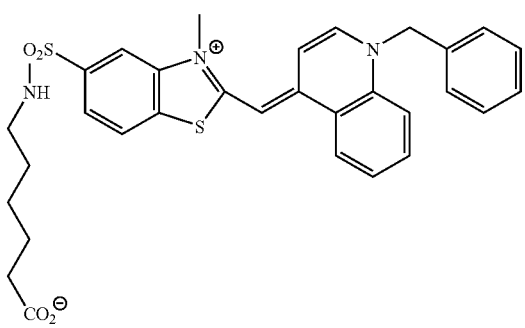

Compound 36

Example 13

Preparation of Compound 37

A mixture of 1.49 g of 2-methylbenzothiazole and 1.63 g of butanesultone is heated at 130° C. for 1.5 hours. Ethyl acetate (40 mL) is added and the resulting mixture heated at reflux for minutes. The resulting product is collected by filtration to give Compound 37.

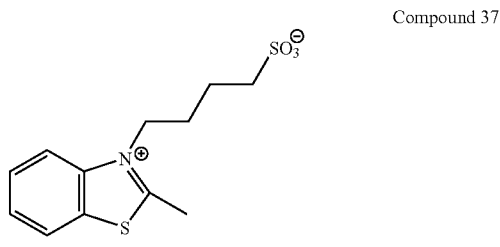

Compound 37

Example 14

Preparation of Compound 38

To 57 mg of Compound 37 and 84 mg of 4-chloro-1-methylquinolinium tosylate in 10 mL of dichloromethane is added 0.07 mL of triethylamine. The reaction mixture is stirred at room temperature overnight and Compound 38 is obtained via filtration.

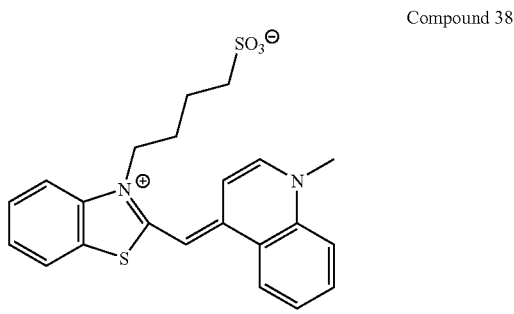

Compound 38

Example 15

Preparation of Compound 39

A mixture of 2.66 g of 2-methylbenzoxazole and 2.68 g of propanesultone is heated at 150° C. for 1 hour. Ethyl acetate (30 mL) is added and the resulting mixture is heated at reflux for 1 hour. Compound 39 is recovered via filtration.

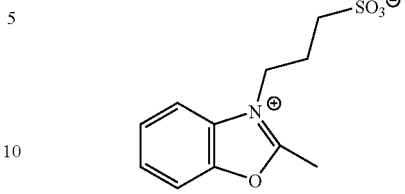

Compound 39

Example 16

Preparation of Compound 40

To a mixture of 0.1 g of Compound 39 and 0.15 g of 4-chloro-1-methylquinolinium tosylate in 10 mL of dichloromethane is added 0.1 mL of triethylamine and the resulting reaction mixture is stirred at room temperature overnight. The volatile components are removed by evaporation under reduced pressure and the resulting residue is stirred in 2 mL of methanol and filtered to obtain Compound 40.

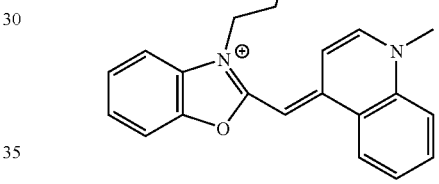

Compound 40

Example 17

Preparation of Compound 41

A mixture of 1.49 g of 2-methylbenzothiazole and 2 g of 4-bromobutyric acid is heated at 150° C. for 1 hour. Ethyl acetate (30 mL) is added and the mixture is heated at reflux for 30 minutes. Compound 41 is obtained via filtration.

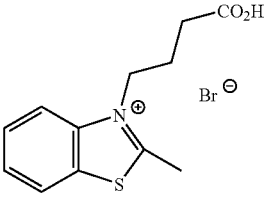

Compound 41

Example 18

Preparation of Compound 42

To a mixture of 0.12 g of Compound 41 and 0.146 g of 4-chloro-1-methylquinolinium tosylate in 10 mL of dichloromethane is added 0.1 mL of triethylamine, and the reaction mixture is stirred overnight. Compound 42 is obtained via filtration.

Compound 42

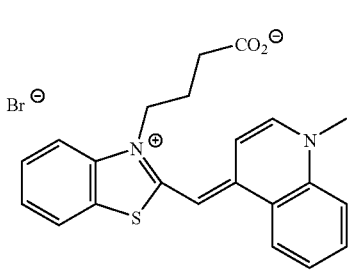

Example 19

Preparation of Compound 43

A mixture of 3 g of 2-methylbenzothiazole and 2.11 g of 2-bromoethanesulfonic acid, sodium salt is heated at 130-140° C. for 8 hours, after which 0.12 g of 4-chloro-1-methylquinolinium tosylate is added. The resulting mixture is stirred in 15 mL of methanol and 0.5 mL of triethylamine is added. The reaction mixture is stirred at room temperature overnight and Compound 43 is purified using silica gel chromatography.

Compound 43

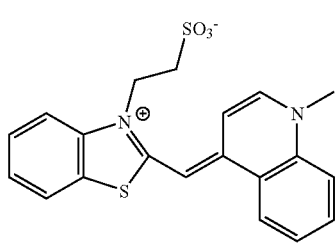

Example 20

Preparation of Compound 44

A mixture of 20 mg of 2-methyl-oxazolo[4,5-b]pyridine and 36 mg of propanesultone is heated in 0.1 mL of DMF at 140° C. for 20 minutes. After cooling to room temperature, 2 mL of ethyl acetate is added and the supernatant solution is decanted. To the crude intermediate 2-methyl-4-(3-sulfopropyl)-oxazolo[4,5-b]pyridinium inner salt is added 1.5 mL of DMF, followed by 33 mg of 4-chloro-1-methylquinolinium tosylate and 0.05 mL of triethylamine. The crude product is then purified using silica gel chromatography to give Compound 44.

Compound 44

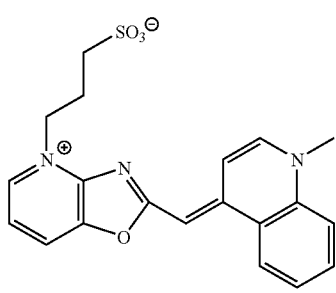

Example 21

Preparation of Compound 45

To a mixture of 0.38 g of the sulfonyl chloride derivative Compound 20 and 0.3 g of 5-((2-aminoethyl)amino)naphthalene-1-sulfonic acid, sodium salt in about 5 mL of DMF is added 0.31 mL of triethylamined and the resulting reaction mixture is stirred at room temperature for several hours. The solvent is removed by evaporation under reduced pressure and the crude product is purified using silica gel column chromatography to yield 0.16 g of Compound 45.

Compound 45

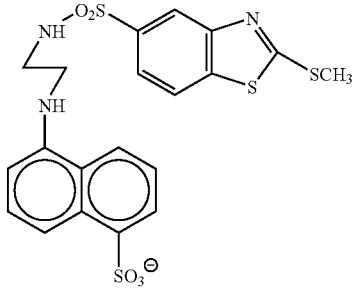

Example 22

Preparation of Compound 46

A mixture of 18 mg of the sulfonic acid sodium salt derivative Compound 45 and 200 mg of methyl toluenesulfonate is stirred at 130° C. for 15 minutes. After cooling down to room temperature, the crude product is washed with 4 mL of ethyl acetate, centrifuged and decanted. The resulting residue is dissolved in 0.5 mL of DMF and 20 mg of 1-benzyl-4-methylquinolinium bromide and 0.07 mL of triethylamine are introduced in that order. Compound 46 is then isolate using silica gel chromatography.

Compound 46

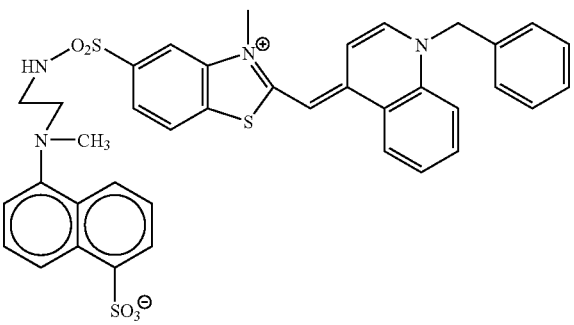

Example 23

Preparation of Compound 47

To a mixture of 0.25 g of the sulfonyl chloride Compound 20 and 0.25 g of 3-aminopropylphosphonic acid in 10 mL of water at room temperature, 1 mL of 10% NaOH is added and stirred at ambient temperature overnight. The water is evapo rated and the crude product is purified on silica gel column to give Compound 47.

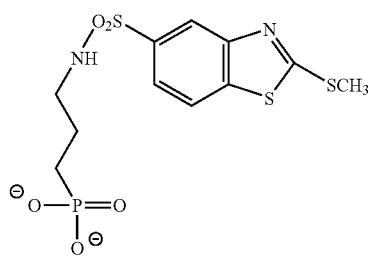
Compound 47

Example 24

Preparation of Compound 48

A mixture of about 5 mg of the phosphonic acid derivative Compound 47 and 4-5 equivalents of methyl toluenesulfonate is heated at 130° C. for 1 hour. Ethyl acetate (2 mL) is added and the suspension is centrifuged and decanted. The residue is then dissolved in about 0.5 mL of DMF and treated with about 25 mg of 1,4-dimethylquinolinium iodide and 0.1 mL of triethylamine and the resulting mixture is stirred for several hours. The solvent is evaporated under reduced pressure and Compound 48 is purified on silica gel.

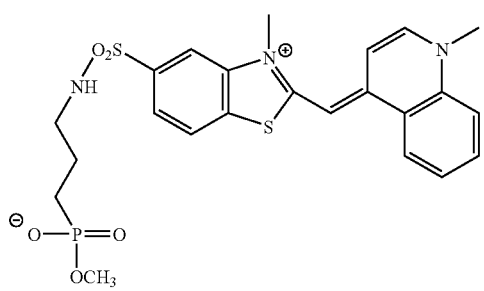
Compound 48

Example 25

Preparation of Compound 54

A mixture of 25 mg of 6-(methoxycarbonyl)-3-methyl-2-methylthio-benzothiazolium tosylate and 20 mg of 1-benzyl-4-methylquinolinium bromide and 0.03 mL of triethylamine is stirred in 1 mL of dichloroethane at room temperature for 2 hours. Several millilters of chloroform are introduced and partitioned with several milliliters of water. The intermediate methyl ester of the desired product is collected by filtration, and then hydrolyzed by aqueous sodium hydroxide in methanol to generate the product, Compound 54.

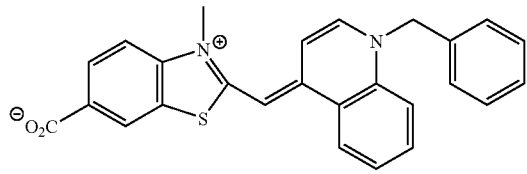
Compound 54

Example 26

Preparation of Compound 49

A mixture of 0.3 g of the bis-sulfonic acid derivative Compound 1, 94 mg of 1,4-dimethylpyridinium iodide and 0.14 mL of triethylamine in 10 mL of methanol is stirred at room temperature for one hour. The crude product is then purified on silica gel to give Compound 49.

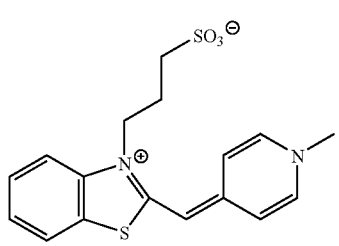
Compound 49

Example 27

Preparation of Compound 50

To a mixture of about 0.4 mmole of 2-(4-aminophenylthio)-4-methyl-1-phenylquinolinium chloride and 0.39 g of Compound 1 in 5 mL of methanol is added 0.21 mL of triethylamine, and the resulting mixture is stirred at room temperature for 2 hours. The crude product is then purified on a silica gel column to give Compound 50.

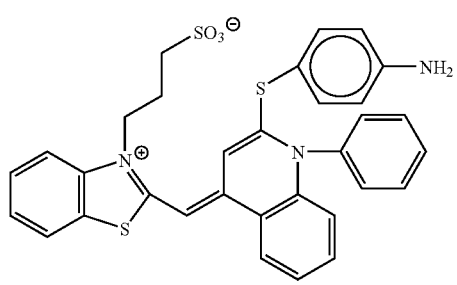
Compound 50

Example 28

Preparation of Compound 51

Compound 51 is made following a procedure similar to the preparation of Compound 50 (see Example 27) excepting that 2-(3,5-dimethylphenylthio)-4-methyl-1-phenylquinolinium chloride is used instead of 2-(4-aminophenylthio)-4-methyl-1-phenylquinolinium chloride. The crude product is purified on a silica gel column to give Compound 51.

Compound 51

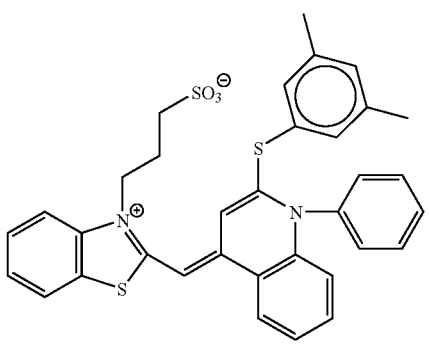

Example 29

Preparation of Compound 52

Compound 52 is made following a procedure similar to the preparation of Compound 50 (see Example 27) excepting that 2-(4,6-dimethylpyrimidinyl-2-thio)-4-methyl-1-phenylquinolinium chloride is used instead of 2-(4-aminophenylthio)-4-methyl-1-phenylquinolinium chloride. The crude product is purified on a silica gel column to give Compound 52.

Compound 52

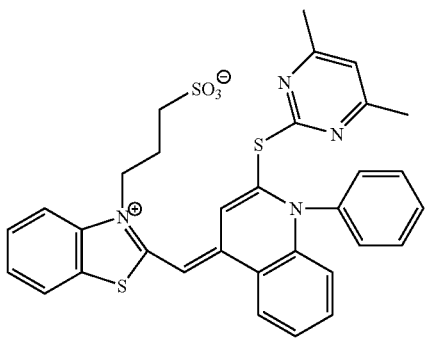

Example 30

Preparation of Compound 53

A mixture of 0.46 g of the bis-sulfonic acid derivative Compound 1, 0.165 g of 1,2-dimethylquinolinium tosylate and 0.14 mL of triethylamine in 10 mL of methanol is stirred at room temperature for two hours. The crude product is purified on silica gel to give Compound 53.

Compound 53

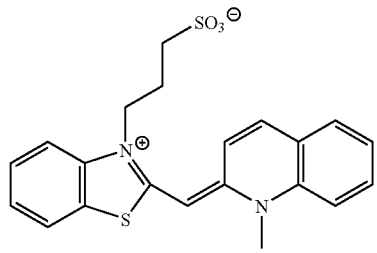

Example 31

Emission Spectra of Compound 25 in the Presence of DNA and RNA Demonstrating Brighter Fluorescent Signal from DNA A stock solution of Compound 25 is made by dissolving about 0.1 to about 0.3 mg of the reporter molecule in 1 mL of DMSO. The stock solution (40 µl) is then diluted in 3 ml 10 mM TRIS, 1 mM EDTA (pH 7.2). This dilute solution resulted in an optical density of approximately 0.058 and extinction coefficient of 45,000, yielding a working concentration of ~2.9-8.8 µM. Compound 25, at about 2.9-8.8 µM, is added to the test samples (1),RNA and 2) DNA calf thymus. The RNA is present at a final concentration of 65 µg/ml and the DNA is present at a final concentration of about 66 µg/mL. After addition of the dye and the nucleic acid, the samples are incubated at room temperature for about 30 minutes, then excited at 504 nm and the resulting emission detected at 522 nm. Compound 25 demonstrates a 600-fold increase in fluorescence signal when bound to DNA when compared to the corresponding RNA complex, as shown in FIG. 1.

This example provides a means for screening reporter compounds for their ability to fluoresce when complexed with DNA or RNA. In addition, this methodology provides a means for screening compounds wherein a particular intensity is desired or compounds that are selective for DNA and/or RNA.

Table 5 below shows the differential fluorescence enhancement of selected compounds when associated with DNA, when compared to their fluorescent enhancement when associated with RNA.

TABLE 5

| DNA-selective compounds | | |
|---|---|---|
| Compound | Ex/Em (nm)[1] | Fluorescence Enhancement Ratio (DNA/RNA)[2] |
| Compound 31 | 503/529 | 1.6 |
| Compound 32 | 509/526 | 4.3 |
| Compound 33 | 507/532 | 4.2 |
| Compound 36 | 502/524 | 9.2 |
| Compound 38 | 502/530 | 2.8 |
| Compound 40 | 475/503 | 2.3 |
| Compound 42 | 502/526 | 3.3 |
| Compound 43 | 499/525 | 2.7 |
| Compound 44 | 520/545 | 1.3 |
| Compound 46 | 501/525 | 3.2 |
| Compound 48 | 496/520 | 2.7 |
| Compound 54 | 508/532 | 7.4 |
| Thiazole Orange[3] | 510/530 | 1.0 |

[1]Complex with nucleic acid
[2]The ratio of the fluorescence enhancement of the compound when associated with DNA to the fluorescence enhancement of the compound when associated with RNA
[3]Included for comparison purposes Table 6 below shows the differential fluorescence enhancement of selected compounds when associated with RNA, when compared to their fluorescent enhancement when associated with DNA.

TABLE 6

RNA-selective compounds

| Compound | Ex/Em (nm)[1] | Fluorescence Enhancement Ratio (RNA/DNA)[2] |
|---|---|---|
| Compound 49 | 444/480 | 2.2 |
| Compound 50 | 508/540 | 3.3 |
| Compound 51 | 508/540 | 2.6 |
| Compound 52 | 517/555 | 1.2 |
| Compound 53 | 480/530 | 1.5 |
| Thiazole Orange[3] | 510/530 | 1.0 |

[1]Complex with nucleic acid
[2]The ratio of the fluorescence enhancement of the compound when associated with RNA to the fluorescence enhancement of the compound when associated with DNA
[3]Included for comparison purposes Example 32

Comparison of In-Solution Binding of Compound 25 with RNA or DNA

Figure 2:
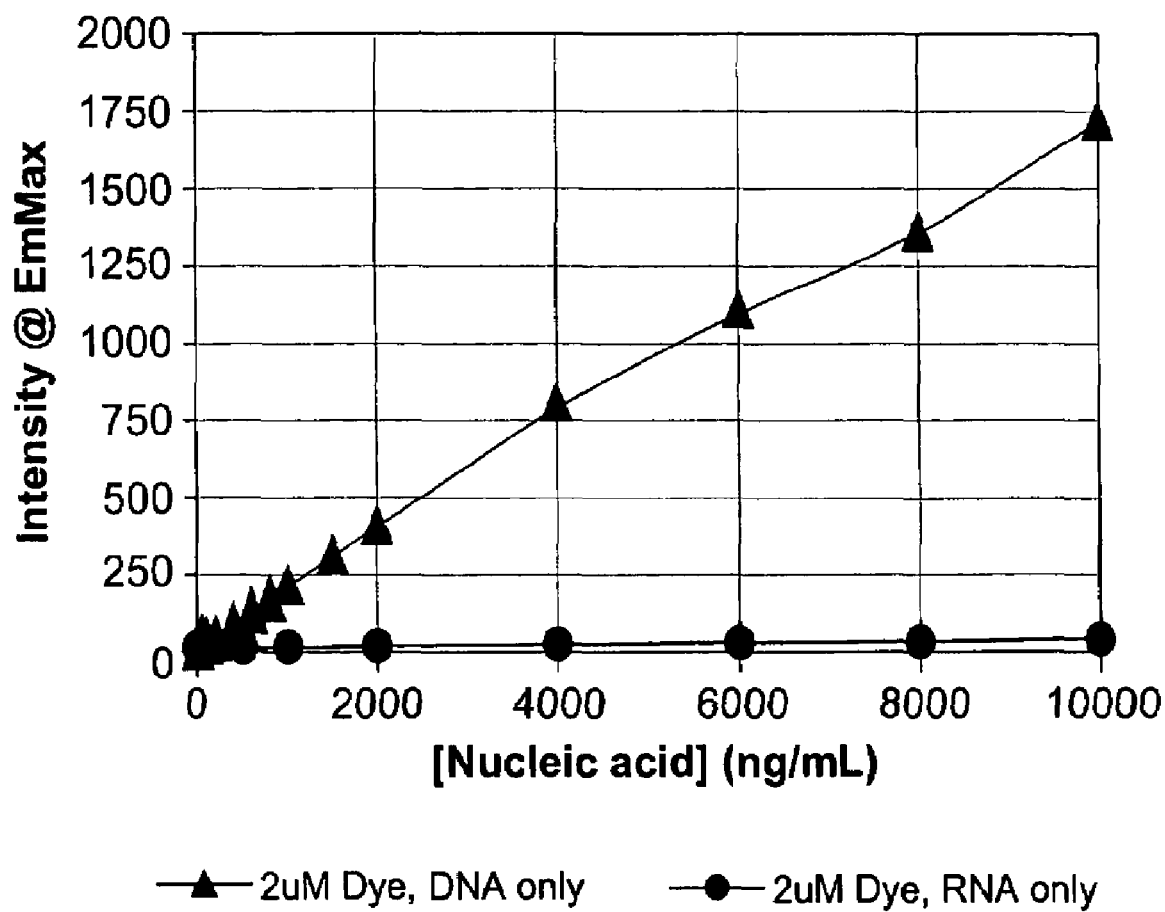
FIG. 2: A plot showing the intensity of the fluorescent signal from Compound 25 when bound to different concentrations of rRNA and DNA (calf thymus) in solution. Compound 25 exhibits little to no detectable fluorescent signal in the presence of RNA, even at a concentration of 10 mg/ml, as described in Example 32.

A buffer solution of 200 µl of 10 mM TRIS, 1 mM EDTA (pH7.2) is added to the wells of a 96-well microplate. RNA and DNA (calf thymus) dilutions in TE (pH 7.2) are added to the appropriate wells to yield the final concentrations of 0-10,000 ng/mL. Compound 25, prepared from a stock solution in DMSO, is added to the microplate wells to a final concentration of 2 µM. The well contents are excited at 504 nm and emission is recorded at 522 nm. Compound 25 demonstrated an increased fluorescence intensity signal with increasing concentrations of DNA, but exhibited little to no fluorescence signal when combined with RNA alone, as shown in FIG. 2. This experimental provides a means for screening potential reporter molecules that may selectively bind DNA or RNA.

Example 33

Comparison of In-Solution Binding of Compound 25 to DNA, RNA or a 1:1 Ratio of RNA and DNA A buffer solution of 200 µl of 10 mM TRIS, 1 mM EDTA (pH 7.2) is added to the wells of a 96-well microplate. RNA and DNA (calf thymus) dilutions in TE (pH 7.2) are added to the appropriate wells to yield final concentrations of 0-4000 ng/mL. In separate wells RNA and DNA are combined for a final concentration of 800, 1600, 2400, 3200 and 4000 ng/mL of nucleic acid. Compound 25, from a stock solution in DMSO, is added to the microplate wells at a final concentration of 2.0 µM. The well contents are excited at 504 nm and emission is recorded at 522 nm. Compound 25 demonstrates selectivity for DNA, as shown in FIG. 3.

Figure 3:
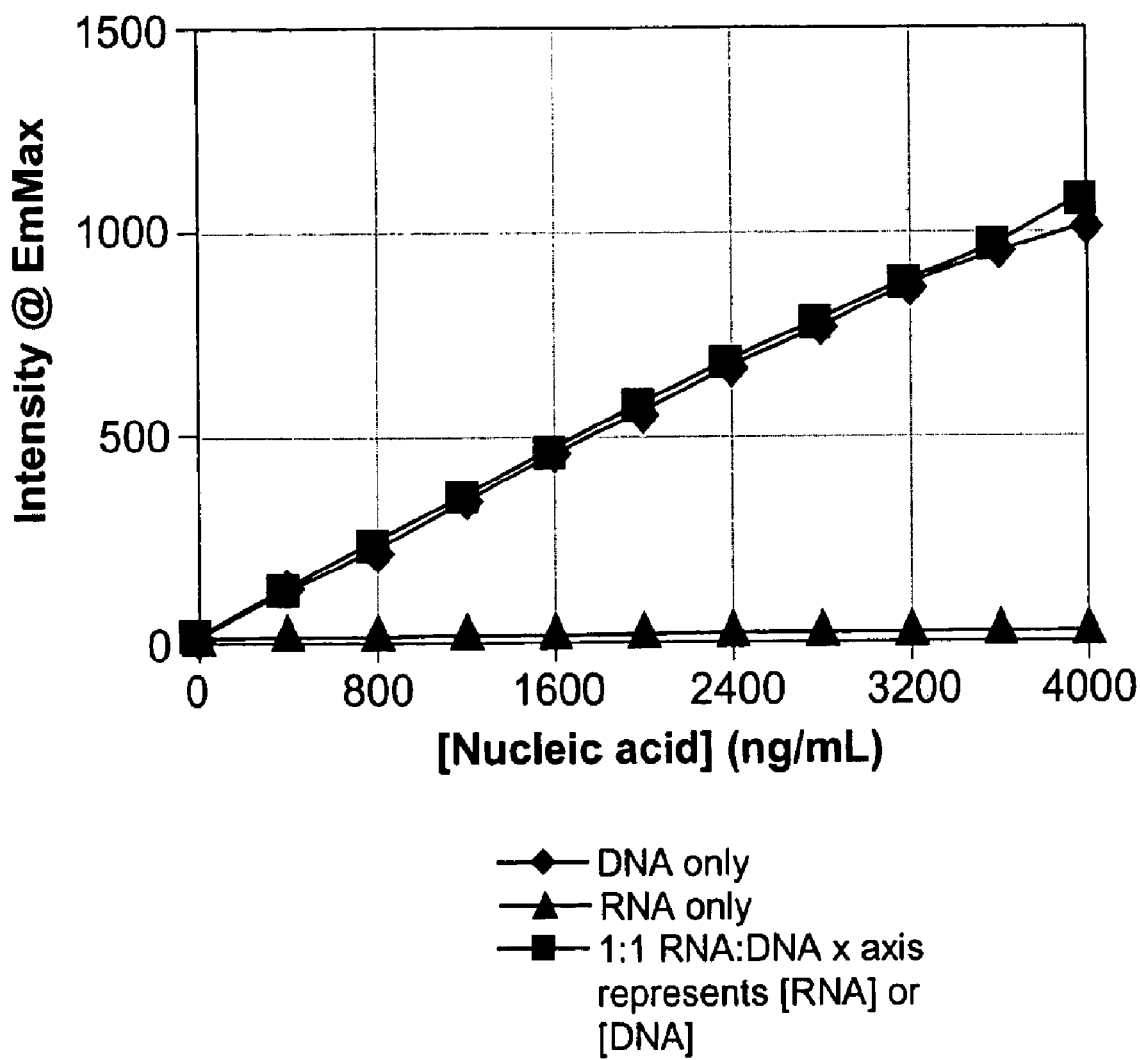
FIG. 3: A plot showing the intensity of the fluorescent signal from Compound 25 when bound to different concentrations of DNA, RNA or RNA+DNA in solution.

FIG. 3 represents an overlay of three graphs with concentration of DNA 0-4000 ng/mL, RNA 0-4000 ng/mL (along the same axis) and RNA+DNA. The combined concentration is always twice the concentration of nucleic acid indicated on the X-axis such that the individual concentration of RNA and DNA depends on the corresponding concentration indicated on the X-axis. In this way the concentrations were combined in the following format: RNA+DNA respectively, 0 ng/mL+0 ng/mL, 800 ng/mL+800 ng/mL, 1600 ng/mL+1600 ng/mL, 2400 ng/mL+2400 ng/mL, 3200 ng/mL+3200 ng/mL, and 4000 ng/mL+4000 ng/mL. Compound 25 either does not bind RNA, or binds RNA with little to no fluorescent signal intensity which is confirmed by the fluorescence response in the presence of RNA and DNA as is observed for the corresponding DNA concentration alone.

This experiment provides a means for screening present reporter molecules for their ability to detect RNA in the presence of DNA, or alternatively for their ability to detect DNA in the presence of RNA Example 34

Comparison of in Solution Binding of Compound 25 to DNA, RNA or a Mixture of DNA and RNA wherein the Concentration of DNA is constant.

A buffer solution of 200 µl of 10 mM TRIS, 1 mM EDTA (pH 7.2) is added to the wells of a 96-well microplate. RNA and DNA (calf thymus) dilutions in TE (pH 7.2) are added to the appropriate wells to yield the final concentrations of 0-4000 ng/mL. DNA (1 µg/ml) is added to varying amounts of RNA (0, 800, 1600, 2400, 3200 and 4000 ng/ml) in TE buffer and added to appropriate wells. Compound 25, from a stock solution in DMSO, is added to the microplate wells to a final concentration of 2.0 µM. The well contents are excited at 504 nm and emission is recorded at 522 nm. Compound 25 demonstrates selectivity for DNA, as shown in FIG. 4.

Figure 4:
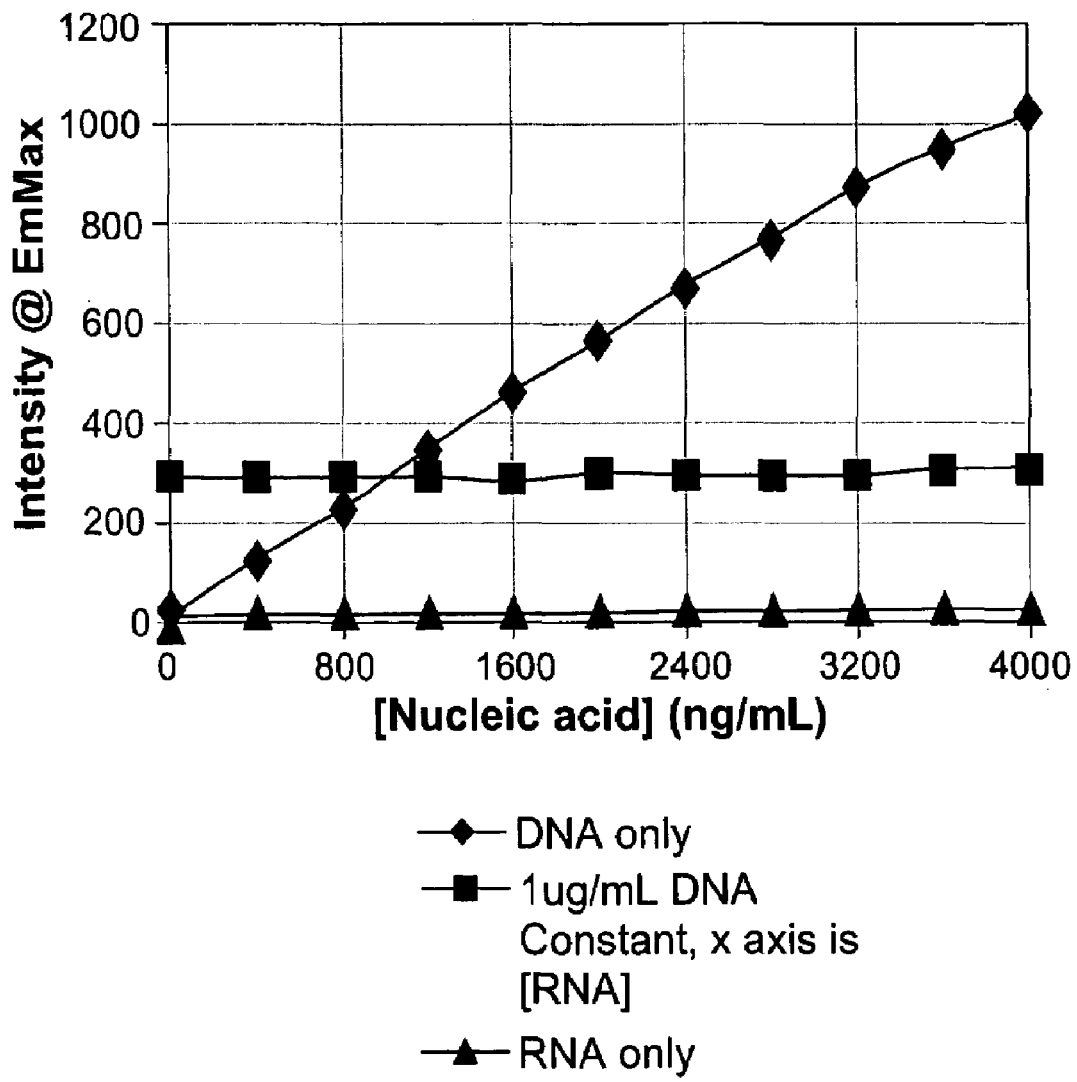
FIG. 4: A plot showing the intensity of the fluorescent signal from Compound 25 when bound to different concentrations of DNA and RNA+DNA, respectively, in solution. These results indicate that Compound 25, in solution, demonstrates an ability to selectively associate with DNA in the presence of varying concentrations of RNA, as described in Example 34.

FIG. 4 is an overlay of two graphs showing fluorescence response due to increasing concentrations of DNA only (0-4000 ng/ml), and fluorescence response due to increasing concentrations of RNA (0-4000 ng/ml) in the presence of a constant concentration of DNA (1000 ng/ml). The results indicate that Compound 25 demonstrates an ability to selectively associate with DNA in the presence of varying concentrations of RNA, that at equal concentrations of RNA and DNA, DNA may be effectively detected using Compound 25, and that Compound 25 may still effectively detect DNA when the concentration of RNA is four times the concentration of DNA.

Example 35

Titration of DNA and RNA in the Presence of Compound 25

Figure 5:
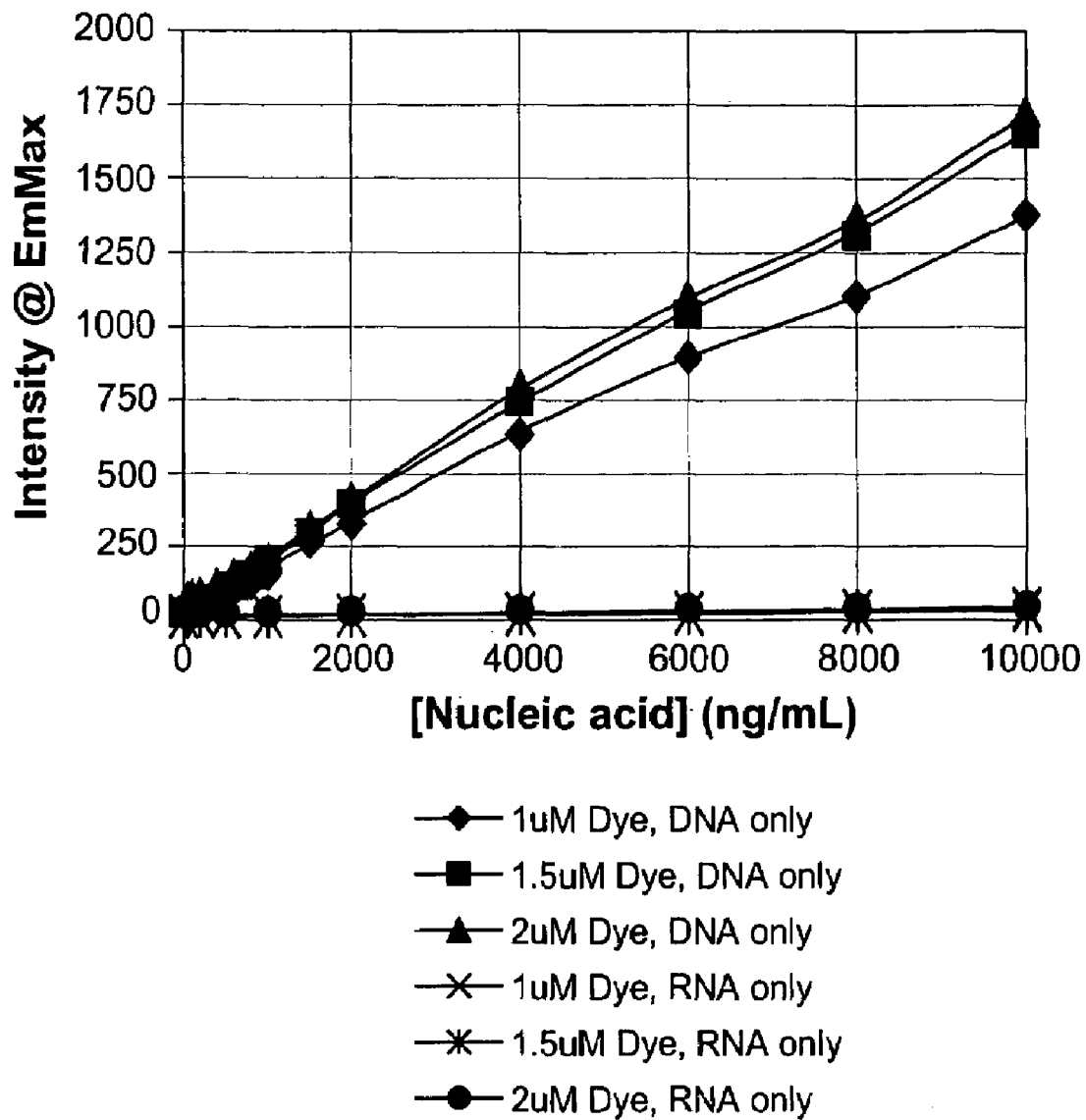
FIG. 5: A plot showing a titration of Compound 25 when bound to DNA or RNA in solution. These results show little to no fluorescent signal in the presence of RNA, and a detectable signal in the presence of DNA, as described in Example 35.

A buffer solution of 200 µl of 10 mM TRIS, 1 mM EDTA (pH 7.2) is added to the wells of a 96-well microplate. RNA and DNA (calf thymus) dilutions in TE (pH 7.2) are added to the appropriate wells to yield the final concentrations of 0-10,000 ng/mL. Compound 25, from a stock solution in DMSO, is added to the microplate wells to a final concentration of 1.0, 1.5 and 2.0 µM. The well contents are excited at 504 nm and emission is recorded at 522 nm. Compound 25 demonstrates a selectivity for DNA with optimal signal when Compound 25 is present at 2.0 µM, as shown in FIG. 5.

Example 36

Detection of dsDNA and ssDNA Spotted on a Microarray

Selectivity for dsDNA

A microarray including a dilution series of plasmid DNA is printed in quadruplicate using a microarray spotter. The dilution series includes spots of about 200 pg to about 1 pg of plasmid DNA printed from either 50% DMSO/50% $H_2O$ (in order to denature the DNA and render it predominantly single stranded) or 3× SSC (in order to retain double-strandedness).

Figure 6:
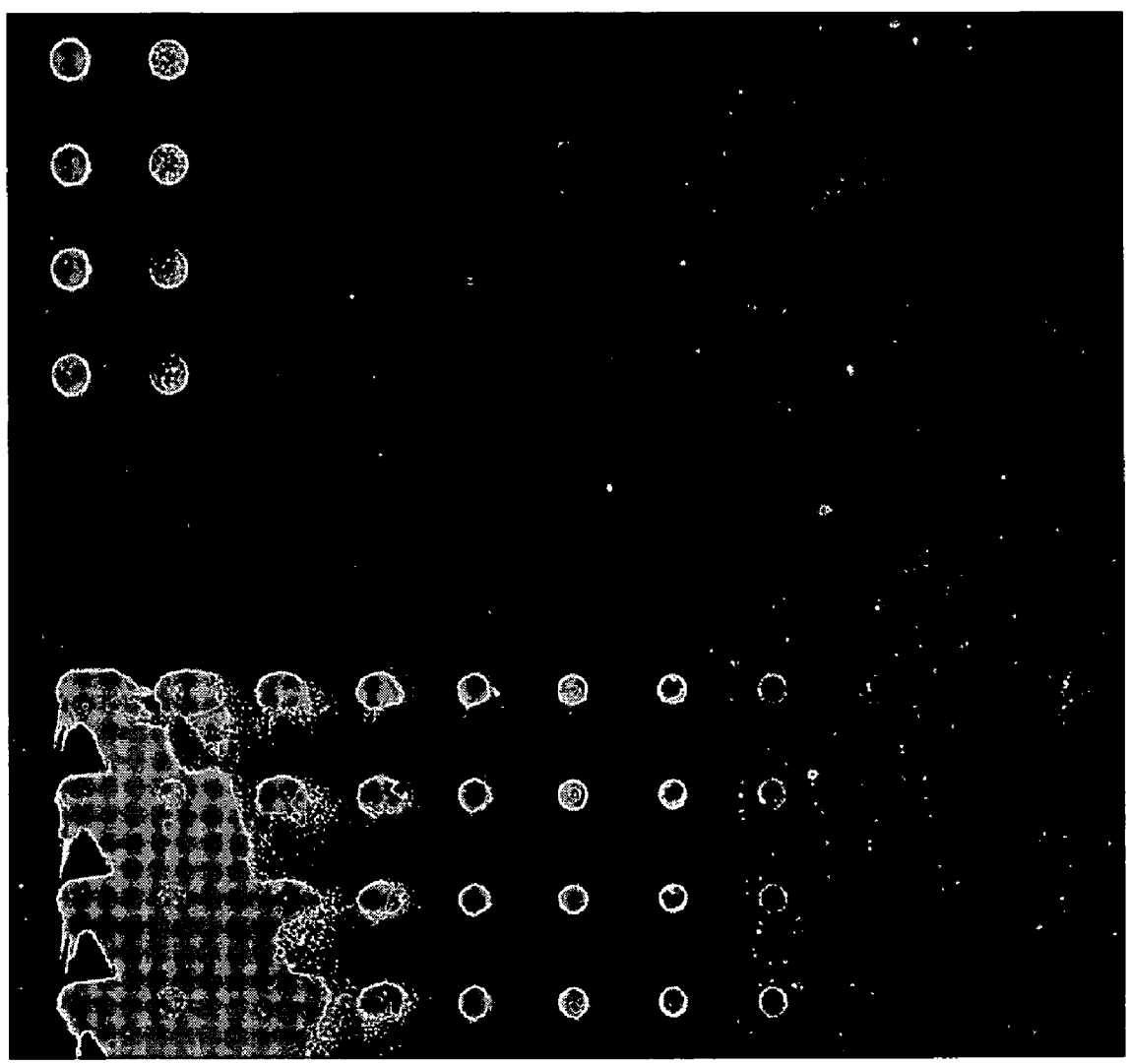
FIG. 6: A black and white image showing the detection of single and double stranded DNA immobilized in a microarray, using Compound 5. These results indicate that Compound 5 is more selective for double stranded DNA compared to single stranded DNA when the nucleic acid is immobilized on solid support. See Example 36.

The slide including the printed microarray is equilibrated in a salt buffer to remove any excess printing buffer, and then soaked in a 1 μM solution of Compound 5 in a salt buffer for 5 minutes, followed by a 5 minute wash in a salt buffer to remove any excess stain. The slide is then imaged by a microarray scanner using 633 nm laser excitation. The resulting false color image clearly indicates that the top row of single-stranded DNA is stained to a lesser degree when compared to the corresponding dilution series of double-stranded DNA, as shown in FIG. 6. This suggests that Compound 5 exhibits higher affinity for double-stranded nucleic acids than for single-stranded nucleic acids when immobilized on solid supports.

Example 37

Detection of Hybridized and dsDNA and ssDNA Spotted on a Microarray

Selectivity for Hybridized DNA

Dilution series of plasmid DNA One (rows 1 and 2, about 100 pg to about 10 fg), plasmid DNA Two (rows 3 and 4, about 10 pg to about 1 fg), and plasmid DNA Three (rows 5 and 6, about 30 pg to about 3 fg), respectively, are printed from 50% DMSO/50% H2O onto a slide using a microarray spotter. The solvent is selected so as to denature the DNA and render it predominantly single-stranded on the slide.

The slide is then hybridized with a fluorescent-labeled (ALEXA FLUOR 488 dye) probe following standard hybridization conditions. The slide is soaked in a staining solution of Compound 5 (about 1 μM) in a salt buffer for 5 minutes, followed by a 1-minute wash in a salt buffer to remove any excess stain. The slide is then imaged with a microarray scanner using 488 nm laser excitation (as shown in FIG. 7), and 633 nm laser excitation (as shown in FIG. 8).

Figure 7:
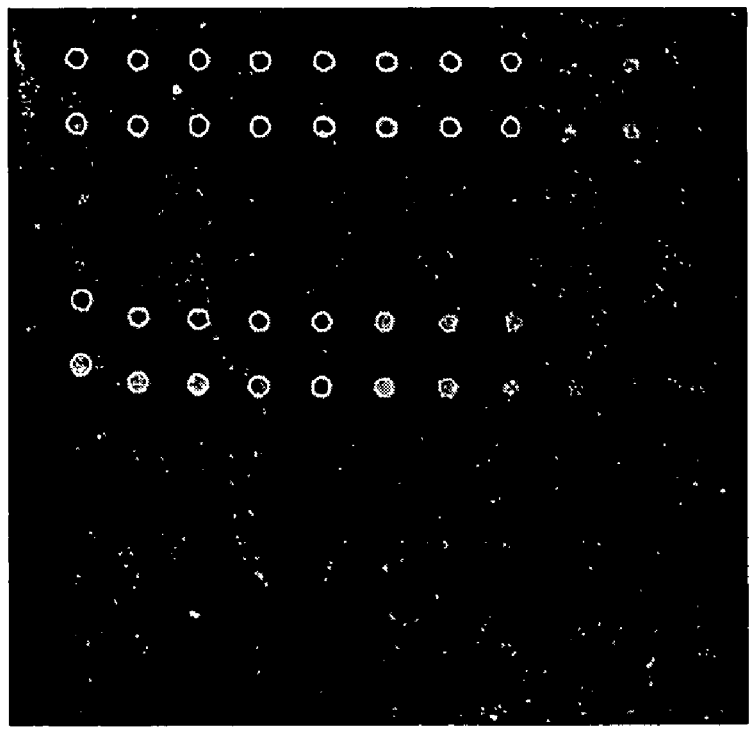
FIG. 7: A black and white image showing the detection of hybridized DNA immobilized in a microarray, by illumination of a fluorescent-labeled hybridization probe. These results show hybridization of the probe to DNA that is 100% complementary (middle rows 3 and 4) and partially complimentary (top rows 1 and 2), but no hybridization to non-complementary DNA (bottom rows 5 and 6), as described in Example 37.
Figure 8:
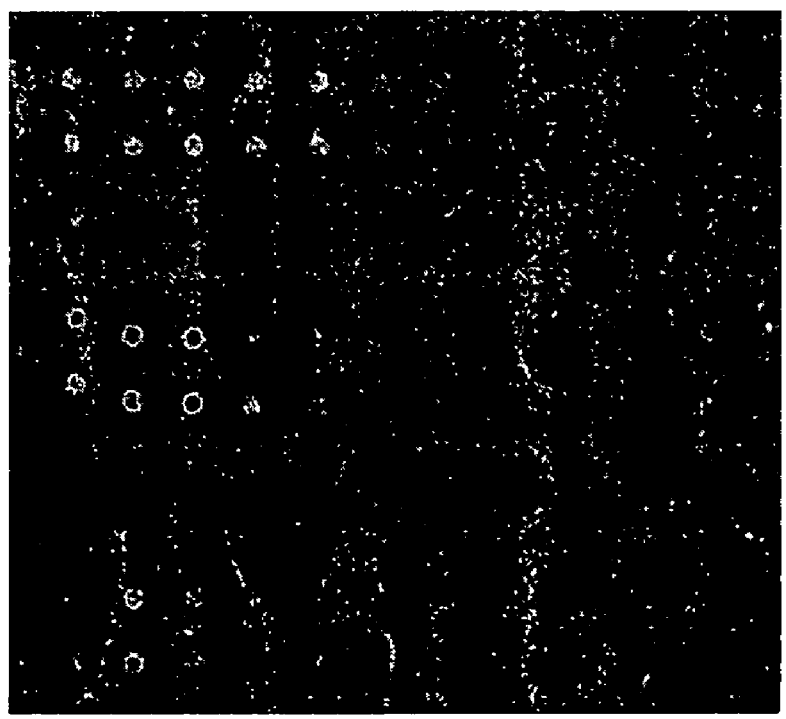
FIG. 8: A black and white image showing the relative fluorescence intensity of single-stranded and hybridized DNA immobilized in a microarray and stained using Compound 5. Hybridized (double-stranded) DNA (in rows 1-4) exhibits brighter fluorescence than single-stranded DNA (in bottom rows 5 and 6), as described in Example 37.

Illumination at 488 nm reveals the presence of the fluorescent-labeled probe, and indicates that the probe hybridizes to DNA that is 100% complementary (middle rows 3 and 4) and partially complimentary (top rows 1 and 2), but does not hybridize to the non-complimentary bottom two rows 5 and 6, as shown in FIG. 7. Illumination at 633 nm reveals DNA stained by Compound 5, and as shown in FIG. 8, staining reveals similar pattern as is generated by the hybridization probe. That is, Compound 5 has a higher affinity for staining hybridized DNA, when compared to unhybridized single-stranded DNA.

The preceding examples can be repeated with similar success by substituting the specifically described nucleic acid reporter molecules of the preceding examples with those generically and specifically described in the forgoing description. One skilled in the art can easily ascertain the essential characteristics of the present invention, and without departing from the spirit and scope thereof, can make various changes and modifications of the invention to adapt to various usages and conditions.

All patents and patent applications mentioned in this specification are herein incorporated by reference to the same extent as if each individual patent or patent application was specifically and individually indicated to be incorporated by reference.

What is claimed is:

1. A method for detecting DNA in the presence of RNA, wherein the method comprises the steps:
   a. combining a nucleic acid reporter molecule with a sample to prepare a labeling mixture, wherein the nucleic acid reporter molecule has a DNA/RNA ratio of fluorescence enhancement greater than about one wherein the nucleic acid reporter molecule is according to the formula

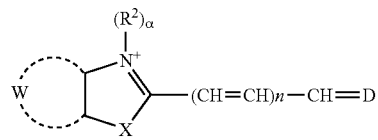

wherein W represents the atoms necessary to form one or two fused substituted 5- or 6-membered aromatic rings or one or two unsubstituted 5- or 6-membered aromatic rings;
   $R^2$ is a substituted alkyl, unsubstituted alkyl, substituted arylalkyl, unsubstituted arylalkyl, substituted heteroalkyl, unsubstituted heteroalkyl, alkoxy, carboxy, carboxyalkyl, hydroxy, hydroxyalkyl, sulfo, sulfoalkyl, amino, aminoalkyl, alkylamino, dialkylamino, or trialkylammonium;
   α is 0 or 1;
   n is 0 or 1;
   X is O, S, or Se;
   D is a substituted pyridinium, unsubstituted pyridinium, substituted quinolinium, or unsubstituted quinolinium moiety;
   with the proviso that the compound is substituted by at least one negatively charged moiety at a physiological pH;
   b. incubating the labeling mixture for a sufficient amount of time for the nucleic acid reporter molecule to associate with DNA in the sample to form an incubated mixture;
   c. illuminating the incubated mixture with an appropriate wavelength to form an illuminated mixture; and,
   d. observing the illuminated mixture whereby the DNA is detected in the presence of RNA.

2. The method according to claim 1, further comprising quantifying the DNA present in the sample.

3. The method according to claim 1, wherein the sample comprises biological fluids, buffer solutions, live cells, fixed cells, eukaryotic cells, prokaryotic cells, nucleic acid polymers, nucleotides, nucleosides, a polymeric gel or tissue sections.

4. The method according to claim 1, wherein the sample comprises cells, tissue, or biological fluids.

5. The method according to claim 1, wherein the sample is present in or on a microarray or a microwell plate.

* * * * *